US010428358B2

(12) United States Patent
Mimitsuka et al.

(10) Patent No.: US 10,428,358 B2
(45) Date of Patent: Oct. 1, 2019

(54) METHOD OF PRODUCING A CHEMICAL PRODUCT

(71) Applicant: Toray Industries, Inc., Tokyo (JP)

(72) Inventors: Takashi Mimitsuka, Kamakura (JP); Kentaro Ishii, Kamakura (JP); Ken Morita, Kamakura (JP); Masashi Higasa, Kamakura (JP); Kenji Sawai, Kamakura (JP); Hideki Sawai, Kamakura (JP); Katsushige Yamada, Kamakura (JP); Shinichi Minegishi, Urayasu (JP)

(73) Assignee: Toray Industries, Inc., Tokyo (JP)

( * ) Notice: Subject to any disclaimer, the term of this patent is extended or adjusted under 35 U.S.C. 154(b) by 277 days.

(21) Appl. No.: 15/051,710

(22) Filed: Feb. 24, 2016

(65) Prior Publication Data

US 2016/0168601 A1 Jun. 16, 2016

Related U.S. Application Data

(62) Division of application No. 13/121,727, filed as application No. PCT/JP2009/066119 on Sep. 16, 2009, now abandoned.

(30) Foreign Application Priority Data

Sep. 30, 2008 (JP) .................................. 2008-252723
Sep. 30, 2008 (JP) .................................. 2008-252724

(51) Int. Cl.
*C12P 7/56* (2006.01)
*C12M 1/00* (2006.01)
*C12N 9/00* (2006.01)
*C12P 1/00* (2006.01)
*C12P 7/02* (2006.01)
*C12P 7/40* (2006.01)
*C12P 13/00* (2006.01)
*C12P 13/04* (2006.01)
*C12P 13/08* (2006.01)
*C12P 19/34* (2006.01)
*C12P 21/02* (2006.01)

(52) U.S. Cl.
CPC .............. *C12P 7/56* (2013.01); *C12M 29/18* (2013.01); *C12M 47/10* (2013.01); *C12N 9/00* (2013.01); *C12P 1/00* (2013.01); *C12P 7/02* (2013.01); *C12P 7/40* (2013.01); *C12P 13/001* (2013.01); *C12P 13/04* (2013.01); *C12P 13/08* (2013.01); *C12P 19/34* (2013.01); *C12P 21/02* (2013.01)

(58) Field of Classification Search
None
See application file for complete search history.

(56) References Cited

U.S. PATENT DOCUMENTS

| 3,717,552 | A | 2/1973 | Hondermarck et al. |
| 5,000,843 | A | 3/1991 | Kumazawa et al. |
| 5,085,997 | A | 2/1992 | Müller |
| 5,124,257 | A | 6/1992 | Azizian et al. |
| 5,143,833 | A | 9/1992 | Datta |
| 5,770,435 | A | 6/1998 | Donnelly et al. |
| 5,869,300 | A | 2/1999 | Yoshioka et al. |
| 6,022,742 | A | 2/2000 | Kopf |
| 6,149,824 | A * | 11/2000 | Chace .................... B01D 61/02 210/167.01 |
| 2004/0259240 | A1 | 12/2004 | Fadden |
| 2005/0272146 | A1 | 12/2005 | Hodge et al. |
| 2006/0019385 | A1 | 1/2006 | Smith et al. |
| 2009/0269812 | A1 * | 10/2009 | Sawai .................... C12P 13/04 435/88 |
| 2011/0111486 | A1 | 5/2011 | Furey |

FOREIGN PATENT DOCUMENTS

| AT | 402 635 B | 7/1997 |
| DE | 30 05 605 A1 | 10/1981 |
| EP | 1 988 170 A1 | 11/2008 |
| JP | 56-50958 B2 | 12/1981 |
| JP | 2-107181 A | 4/1990 |
| JP | 2-219582 A | 9/1990 |
| JP | 3-500486 A | 2/1991 |
| JP | 6-345683 A | 12/1994 |
| JP | 10-150996 A | 6/1998 |

(Continued)

OTHER PUBLICATIONS

Marek Gryta "The fermentation process integrated with membrane distillation" Separation and Purification Technology 24 (2001) 283-296 (Year: 2001).*

(Continued)

*Primary Examiner* — Thane Underdahl

(74) *Attorney, Agent, or Firm* — DLA Piper LLP (US)

(57) ABSTRACT

A method of producing a chemical product includes cultivating microorganisms or culture cells in a fermentation tank; transferring a culture liquid from the fermentation tank to a membrane separation tank to filter the culture liquid through a separation membrane; and collecting a fermentation product from a filtration liquid as the chemical product while refluxing an unfiltered culture liquid that has not been filtered to be joined to the culture liquid on an upstream side of the membrane separation tank, wherein one portion of the culture liquid to be transferred from the fermentation tank is allowed to bypass the membrane separation tank depending on a pressure at a culture liquid flow-in side of the membrane separation tank.

8 Claims, 22 Drawing Sheets

Specification includes a Sequence Listing.

(56) References Cited

FOREIGN PATENT DOCUMENTS

| | | |
|---|---|---|
| JP | 2004-222569 A | 8/2004 |
| JP | 2005-027533 A | 2/2005 |
| JP | 2005-333886 A | 12/2005 |
| JP | 2008-212138 A | 9/2008 |
| WO | 89/10408 A1 | 11/1989 |
| WO | 2007/097260 A1 | 8/2007 |
| WO | 2007/120449 A1 | 10/2007 |

OTHER PUBLICATIONS

A.J. Daugulis et al., "Extractive Fermentation—Integrated Reaction and Product Recovery," *Biotechnology Letters*, vol. 9, No. 6 (1987), pp. 425-430.

Toshihiko Hirao et al., "L-Lysine -Lysine production in continyuous culture of an L-lysine -lysine hyperproducing mutant of *Corynebacterium glutamicum*," *Applied Microbiology and Biotechnology*, vol. 32 (1989), pp. 269-273.

James B. McKinlay et al., "Insights into *Actinobacillus succinogenes* Fermentative Metabolism in a Chemically Defined Growth Medium," Applied and Environmental Microbiology, vol. 71, No. 11, Nov. 2005, pp. 6651-6656.

Supplementary European Search Report dated Mar. 2, 2015 from corresponding European Application No. 09817650.6.

\* cited by examiner

METHOD OF PRODUCING A CHEMICAL PRODUCT

TECHNICAL FIELD

This disclosure relates to a method of producing a chemical product by utilizing culture of microorganisms or culture cells. More specifically, this disclosure concerns a method of producing a chemical product and a fermentation apparatus in which, while carrying out culture, a liquid containing a fermentation product (chemical product) produced by the culture is efficiently filtered from a culture liquid containing microorganisms or culture cells through a separation membrane to collect the fermentation product so that a desired chemical product can be produced with high productivity.

BACKGROUND

The material producing method relating to the culture of microorganisms or culture cells is mainly classified into (1) Batch culture method and Fed-Batch culture method, as well as (2) continuous fermentation method.

In the above-mentioned Batch culture method and Fed-Batch culture method of (1), there are advantages in which culture can be completed using only a simple facility in a short time, and little damage is caused by bacterial contamination. For this reason, these methods have been conventionally used as a substance producing method utilizing microorganisms or culture cells. However, in those methods, since the concentration of fermentation product in a culture liquid becomes higher with an elapse of the time, the productivity and yield are lowered, for example, by an increase of the osmotic pressure or inhibition of the fermentation due to the product itself. For those reasons, these culture methods make it difficult to maintain the productivity and yield of a fermentation product in a high level stably for a long time.

On the other hand, the continuous fermentation method of the above-mentioned (2) is characterized in that, by avoiding the fermentation product in a fermentation tank from accumulating with a high concentration, the productivity and yield can be maintained in a high level for a long time.

For example, a continuous fermentation method has been disclosed with respect to the fermentation of L-glutamic acid (see JP-A No. 10-150996) and L-lysine (see Toshihiko Hirao et al., Appl. Microbiol. Biotechnol. 32, 269 273 (1989)). However, in these examples, although materials such as nutrients are continuously supplied to a culture liquid, the culture liquid containing microorganisms or culture cells is also drawn, with the result that the microorganisms or culture cells in the culture liquid are diluted; therefore, the improvement of its production efficiency is limited.

For this reason, as the continuous fermentation method, a method has been proposed in which microorganisms or culture cells are filtered through a separation membrane, and while the fermentation product is collected from a filtration liquid, the filtered microorganisms or culture cells are held in the fermentation tank or refluxed thereto to maintain the concentration of the microorganisms or cells in the culture liquid in a high level.

For example, a technique has been proposed in which continuous fermentation is carried out by using a continuous fermentation apparatus with a separation membrane (see International Publication No. 07/097260 Pamphlet). In this proposal, a continuous fermentation apparatus provided with a tank used for cultivating microorganisms or culture cells and a tank used for membrane separation on a target fermentation product from the microorganisms and culture cells in the culture liquid, is used so that various chemical products can be produced at a higher production speed in comparison with the batch culture method and with the fed-batch culture method.

In the continuous fermentation apparatus utilizing a separation membrane, it is thought that improving the flow velocity of culture liquid inside a membrane separation tank leads to make the membrane less fouling; as a result, the production speed can be improved due to increase in the quantity of filtration liquid through the separation membrane.

In WO '260, however, since the liquid transfer quantity from the fermentation tank and the flowing quantity into the membrane separation tank cannot be controlled separately, the flowing quantity of the culture liquid to be supplied to the membrane separation tank depends on the flowing quantity of the culture liquid transferred from the fermentation tank. Therefore, in an attempt to change the flow velocity of the culture liquid inside the membrane separation tank, the liquid transfer quantity from the fermentation tank needs to be changed, with the result that a liquid mixing state inside the fermentation tank is changed to cause serious changes of culture conditions. Moreover, when a pressure inside the membrane separation tank was increased due to fouling of the membrane or an increase in the concentration of the microorganisms or culture cells with an elapse of the time, and the like, it is preferable to reduce the flowing quantity of the culture liquid to be supplied to the membrane separation tank to optimize the membrane separation itself. However, when the flowing quantity of the culture liquid to be supplied to the membrane separation tank is changed, the culture conditions in the fermentation tank are changed greatly. For this reason, the flowing quantity of the culture liquid to be supplied to the membrane separation tank cannot be changed easily. In addition, when the quantity of culture liquid to be transferred from the fermentation tank is reduced to optimally control the pressure inside the membrane separation tank, the flow velocity of the culture liquid inside a liquid transfer line is decreased and the microorganisms or culture cells are precipitated inside the liquid transfer line, and a problem of decreasing of the production efficiency occurs. In contrast, when the pressure inside the membrane separation tank is too high, the microorganisms in the culture liquid transferred outside from the membrane separation tank might be damaged due to pressure fluctuation.

It could therefore be helpful to provide a method of producing a chemical product that can control flow velocity of a culture liquid inside a membrane separation tank without giving influences to culture conditions in the fermentation tank, and also suppress precipitation of microorganisms or culture cells so that the production efficiency of the chemical product can be improved, as well as a fermentation apparatus to which such a method can be desirably applied.

We found that by using any of the following structures (1) to (14), it is possible to properly maintain culture conditions (retention time of the culture liquid and so on), while controlling the flow velocity of culture liquid inside a membrane separation tank, and consequently to efficiently produce a chemical product, and complete this disclosure.

(1) A method of producing a chemical product including the steps of: cultivating microorganisms or culture cells in a fermentation tank; transferring a culture liquid from the fermentation tank to a membrane separation tank to filter the culture liquid through a separation membrane; and collecting a fermentation product from a filtration liquid as the chemical product while refluxing an unfiltered culture liquid that has not been filtered to be joined to the culture liquid on an upstream side of the membrane separation tank, wherein one portion of the culture liquid to be transferred from the fermentation tank is allowed to bypass the membrane separation tank depending on a pressure at the culture liquid flow-in side of the membrane separation tank.

(2) The method of producing a chemical product according to the above-mentioned (1), in which a flowing quantity of the culture liquid to be allowed to bypass the membrane separation tank is controlled so that a gauge pressure at the culture liquid flow-in side of the membrane separation tank is 1 MPa or less.

(3) The method of producing a chemical product according to the above-mentioned (1) or (2), in which one portion of the unfiltered culture liquid is refluxed to be joined to the culture liquid in the fermentation tank, while the rest of the portion of the unfiltered culture liquid is refluxed to be joined to a culture liquid located between the fermentation tank and the membrane separation tank.

(4) The method of producing a chemical product according to the above-mentioned (3), in which a flowing quantity of the unfiltered culture liquid to be refluxed to be joined to the culture liquid located between the fermentation tank and the membrane separation tank and a flowing quantity of the unfiltered culture liquid to be refluxed to be joined to the culture liquid in the fermentation tank are each independently controlled.

(5) The method of producing a chemical product according to the above-mentioned (3) or (4), in which a ratio of a flowing quantity of the unfiltered culture liquid to be refluxed to be joined to the culture liquid in the fermentation tank to a flowing quantity of the unfiltered culture liquid to be refluxed to be joined to the culture liquid located between the fermentation tank and the membrane separation tank is 1 or less.

(6) The method of producing a chemical product according to any one of the above-mentioned (1) to (5), in which each of the linear speed of the culture liquid to be transported from the fermentation tank to the membrane separation tank, the linear speed of the unfiltered culture liquid that is refluxed from the membrane separation tank to be joined to the culture liquid on the upstream side of the membrane separation tank and the linear speed of the culture liquid that is allowed to bypass the membrane separation tank is 2.5 cm/sec or more.

(7) The method of producing a chemical product according to any one of the above-mentioned (1) to (6), in which a quantity of culture liquid to flow into the membrane separation tank and/or a quantity of filtration liquid from the separation membrane are adjusted so that the recovery percentage of the quantity of filtration liquid from the separation membrane to the quantity of culture liquid to flow into the membrane separation tank is 10.0% or less.

(8) The method of producing a chemical product according to any one of the above-mentioned (1) to (7), in which a ratio of the culture liquid volume in the fermentation tank to a culture liquid volume in the membrane separation tank is 4 or more to 100 or less.

(9) A continuous fermentation apparatus including: a fermentation tank for cultivating microorganisms or culture cells; a membrane separation tank having a separation membrane used for collecting a fermentation product produced in a culture liquid from the fermentation tank; a circulation line that connects the fermentation tank with the membrane separation tank to transfer the culture liquid to the membrane separation tank, and refluxes an unfiltered culture liquid that has not been filtered through the separation membrane to be joined to the culture liquid on the upstream side of the membrane separation tank; and a culture liquid transfer means installed in the circulation line, in which this structure further includes a bypass line for the membrane separation tank; a detection means for a pressure at the culture liquid flow-in side of the membrane separation tank; and a flowing quantity control means installed in the bypass line.

(10) The continuous fermentation apparatus according to the above-mentioned (9), in which the flowing quantity control means is operated in response to the detection result of the detection means.

(11) The continuous fermentation apparatus according to the above-mentioned (9) or (10), further including a linear speed detection means for the circulation line so that the flowing quantity control means and/or the culture liquid transfer means are operated in response to the detection result of the linear speed detection means.

(12) The continuous fermentation apparatus according to any one of the above-mentioned (9) to (11), in which the membrane separation tank is set up in a circulation circuit having a liquid transfer means different from the culture liquid transfer means, which is independent from the fermentation tank.

(13) The continuous fermentation apparatus according to any one of the above-mentioned (9) to (12), in which the circulation line has an opening at a position that is immersed with the culture liquid to be stored in the fermentation tank.

(14) The continuous fermentation apparatus according to any one of the above-mentioned (9) to (13), in which the ratio of the fermentation tank volume to the membrane separation tank volume is from 4 or more to 100 or less.

One portion of the culture liquid to be transferred from the fermentation tank is allowed to bypass the membrane separation tank depending on a pressure at the culture liquid flow-in side of the membrane separation tank, that is, the flowing quantity of the culture liquid to be supplied to the membrane separation tank and the flowing quantity of the culture liquid to be transferred from the fermentation tank can be controlled independently. As a result, it is possible to make fouling of the membrane hardly occur, by appropriately changing the flow velocity of the culture liquid inside the membrane separation tank without changing the culture conditions, and consequently to increase the quantity of filtration liquid and improve the producing speed. Even if fouling of the membrane occurs with an elapse of the time or the concentration of the microorganisms or culture cells increases to cause a pressure rise inside the membrane separation tank, it is possible to transfer the culture liquid to the membrane separation tank, without causing virtually any change of culture conditions in the fermentation tank, and also to control the flowing quantity of the culture liquid to be supplied to the membrane separation tank and the pressure exerted in the membrane separation tank, while maintaining a flow velocity that hardly causes the microorganisms or culture cells to precipitate in the circulation line used for refluxing the unfiltered culture liquid that has not been filtered by the separation membrane, and as a result, it becomes possible to prevent damages to the membrane separation tank and also to prevent destruction of the microorganisms and culture cells in the culture liquid due to pressure fluctuations. Moreover, even upon occurrence of a failure inside the membrane separation tank, it is possible to completely stop the supply of the culture liquid into the membrane separation tank and correct the failure inside the membrane separation tank, or to exchange or switch membrane separation tanks while the fermentation is being continuously carried out.

Moreover, by controlling the recovery percentage of the filtration liquid in the membrane separation tank to 10% or less, with one portion of the culture liquid to be transferred from the fermentation tank being allowed to bypass the membrane separation tank depending on the pressure at the culture liquid flow-in side of the membrane separation tank, it becomes possible to further prevent fouling of the membrane and to prolong a continuous fermentation time.

As described above, production efficiency and sugar-related yield of a fermentation product obtained by continuous fermentation (that is, a desired product) can be simultaneously improved, and by further controlling the recovery percentage in the membrane separation tank to 10% or less, the continuous fermentation time can be also prolonged.

EXPLANATION OF REFERENCE NUMERALS

Figure 1A:
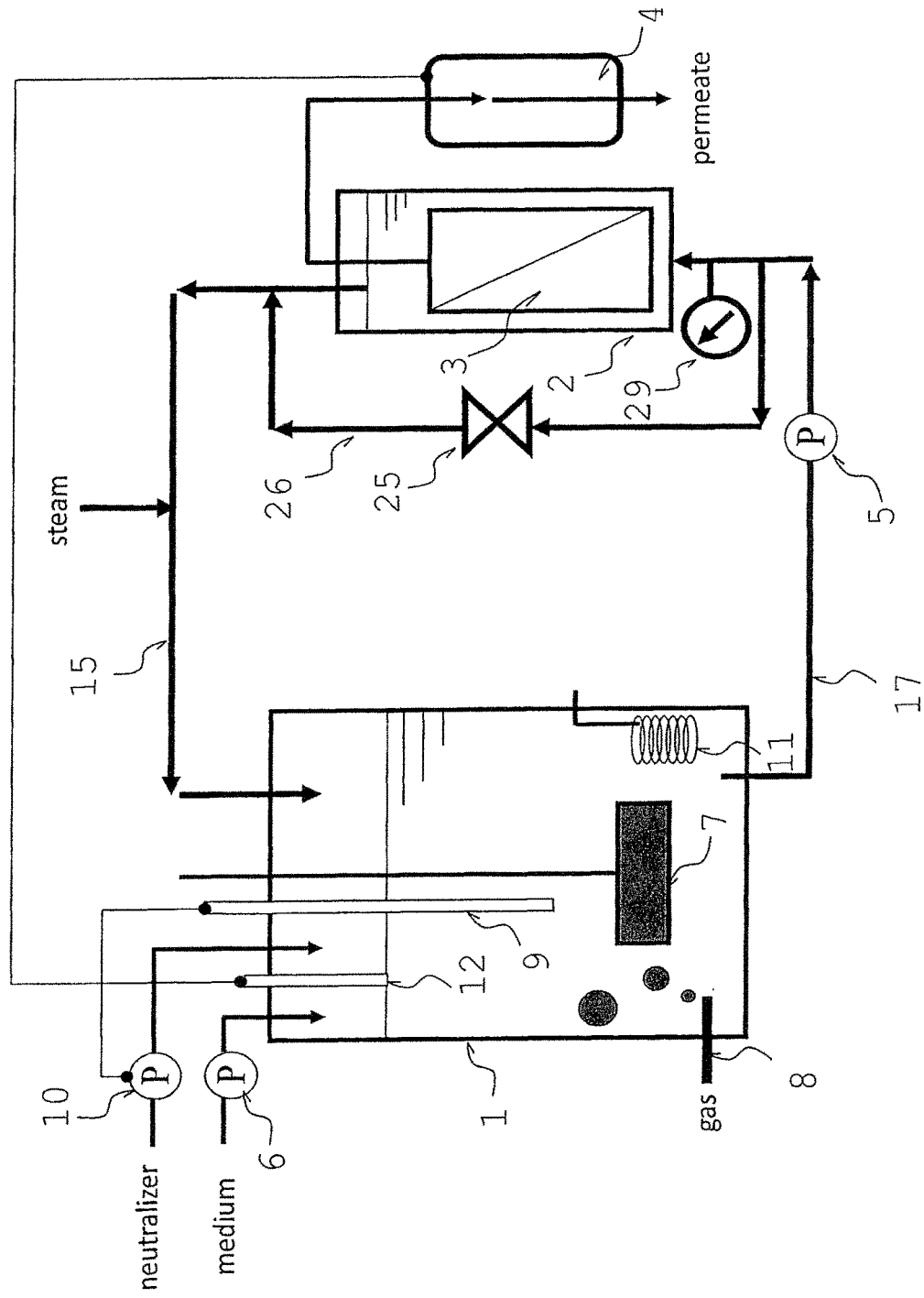
FIGS. 1A-1C outline schematic views that explain one example of our continuous fermentation apparatus with steam supplies located in different circulation line locations.

1 Fermentation tank
2, 2' Membrane separation tank
3, 3' Separation membrane
4 Filtration pump
5 Pump
6 Medium supply pump
7 Stirring shaft
8 Gas supply line
9 pH sensor
10 Neutralizer pump
11 Temperature adjuster
12 Level sensor
13 Atmosphere pressure opening unit
14A Joining point
14B Branch point
15 Liquid transfer line (return of unfiltered culture fluid to fermentation tank)
16 Pump
17 Transfer line
18 Supporting plate
19 Flow passage member
20 Separation membrane
21 Concave section
22 Liquid collecting pipe
23 Upper resin sealing layer
24 Lower resin sealing layer
25 Flowing-quantity control means
26 Bypass line
27, 27' Membrane separation tank open/close valve (medium supply side)
28, 28' Membrane separation tank open/close valve (medium discharge side)
29 Pressure meter
30 Flowing quantity meter

DETAILED DESCRIPTION

We provide a method of producing a chemical product, in which microorganisms or culture cells are cultivated in a fermentation tank, and the culture liquid is continuously transferred from the fermentation tank to a membrane separation tank to be filtered through a separation membrane so that a fermentation product is collected from the filtration liquid as a chemical product, while an unfiltered culture liquid that has not been filtered is refluxed to be joined to the culture liquid on an upstream side from the membrane separation tank, and at this time, one portion of the culture liquid transferred from the fermentation tank is allowed to bypass the membrane separation tank in response to a pressure of the culture liquid at the flow-in side of the membrane separation tank.

Figure 1B:
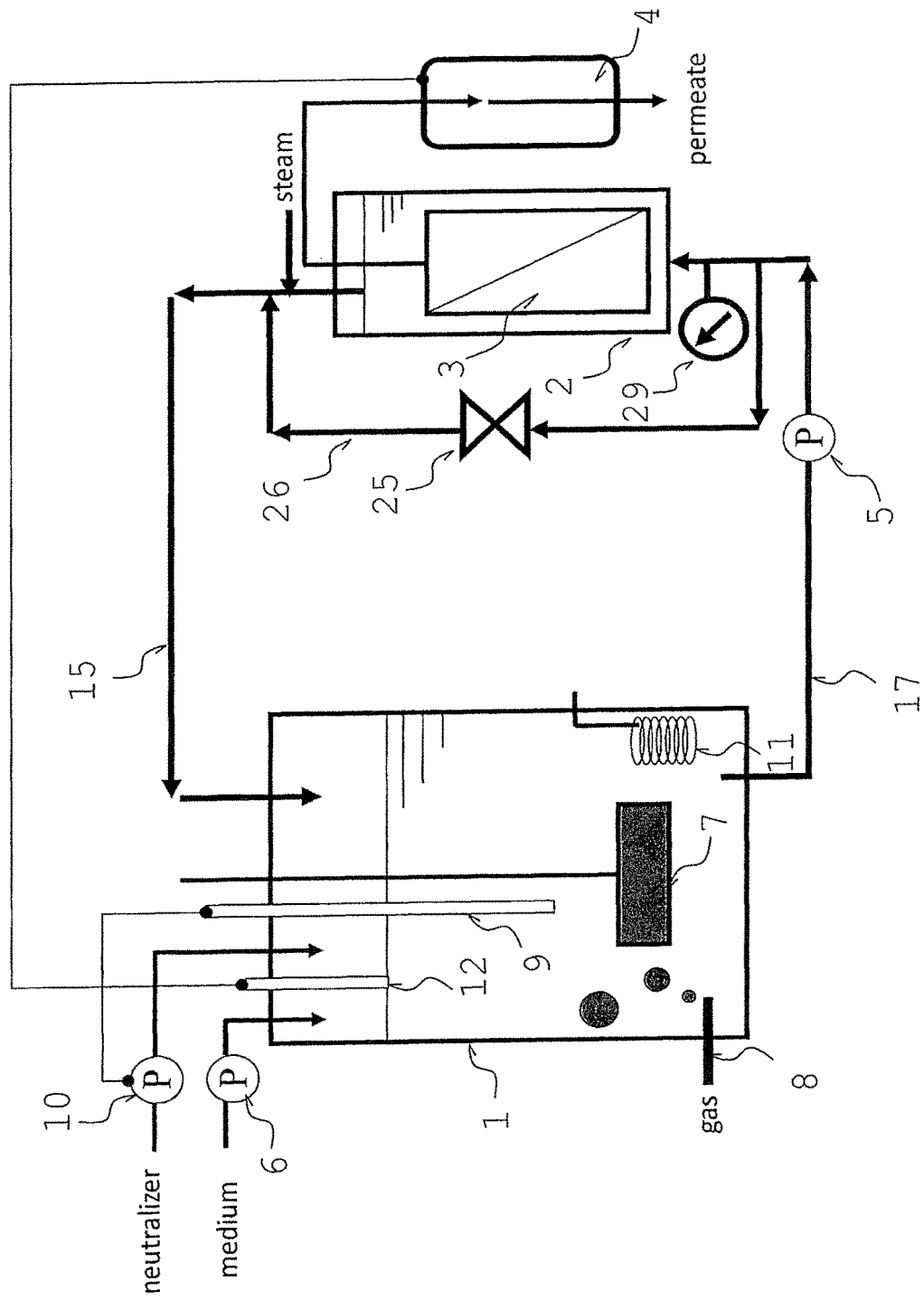
Figure 1C:
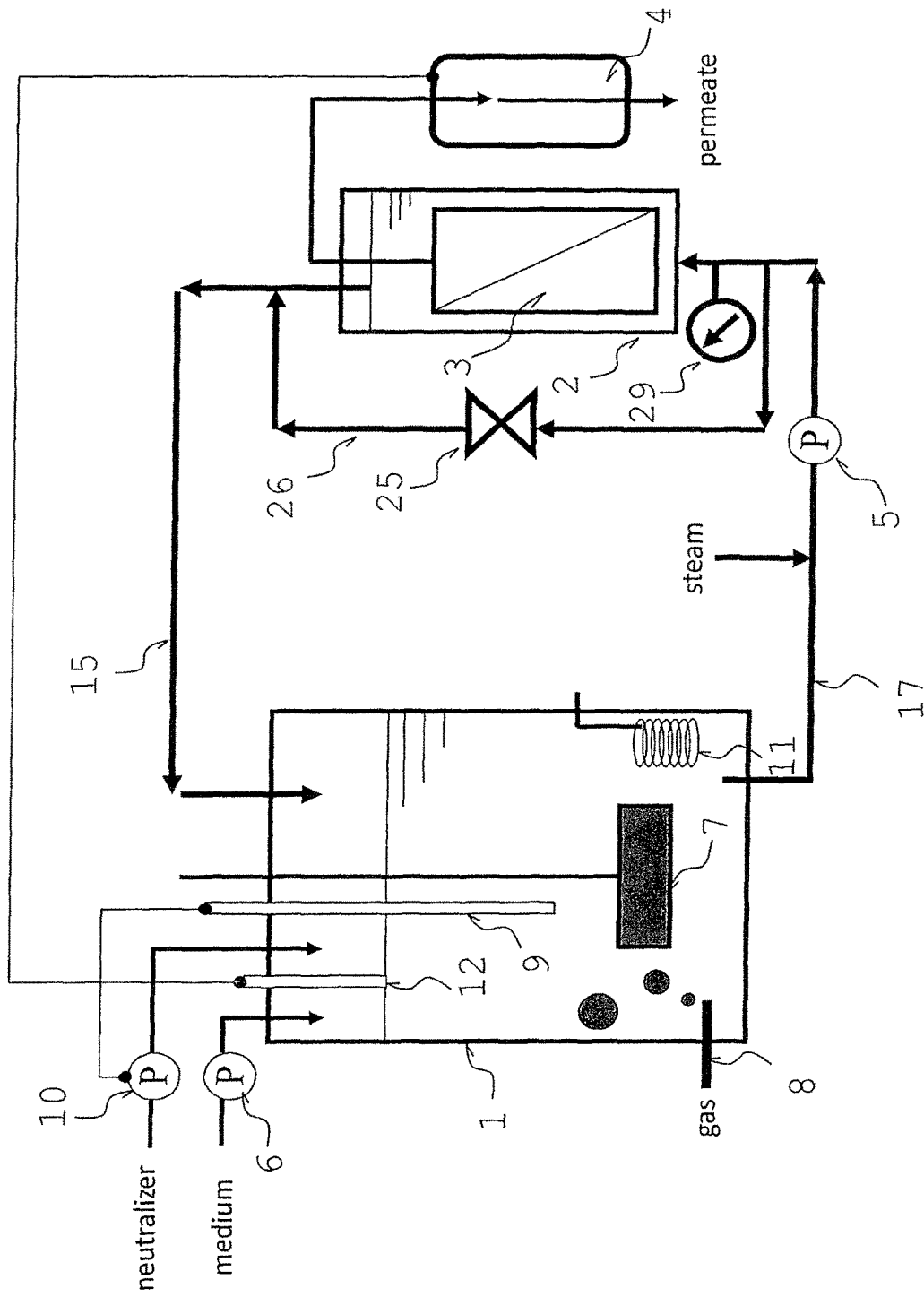

Our methods are executed by a fermentation apparatus, for example, shown in FIGS. 1A-1C. FIGS. 1A-1C outline schematic views showing a fermentation apparatus in accordance with one example with steam supplies positioned in different circulation line locations.

The fermentation apparatus shown in FIGS. 1A-1C is constituted of a fermentation tank 1 in which microorganisms or culture cells are cultivated, and a membrane separation tank 2 provided with a separation membrane 3 used to filter the culture liquid. The membrane separation tank 2 is installed outside a fermentation reaction tank, and connected to the fermentation tank 1 through a liquid transfer line 17 and a liquid transfer line 15 (circulation line).

The fermentation tank 1 has a function of continuously cultivating microorganisms or culture cells, and any tank may be used as this, as long as the circulation line can be connected to the tank; thus, a jar fermenter or the like, which has been conventionally used to cultivate microorganisms or culture cells, may be utilized.

The fermentation tank 1, which connects to a medium supply pump 6, is provided with a stirrer 7 so that a medium is loaded into the fermentation tank 1 by the medium supply pump 6, and, if necessary, allows the stirrer 7 to stir the culture liquid inside the fermentation tank 1. Moreover, a gas-supply device 8 also connects to this so that, if necessary, a required gas is supplied by the gas-supply device 8, In this structure, to recover and recycle the supplied gas and to again supply the gas by the gas-supply device 8, for example, a pipe is preferably located between a head space of the fermentation tank 1 and the gas-supply device 8 so that, by allowing the supply gas to flow in the order of the head space, the pipe and the gas-supply device 8, recovery and recycle may be preferably carried out.

Moreover, a pH sensor-control device 9 and a pH adjusting solution supply pump 10 are attached to the fermentation tank 1, if necessary, to adjust the pH of the culture liquid. Of course, to control the pH of the culture liquid by supplying both of acid and alkali upon culture, a plurality of pH adjusting solution supply pumps are preferably used. Moreover, if necessary, a temperature adjuster 11 is also attached thereto to adjust the temperature of the culture liquid to produce a chemical product with high productivity. Additionally, as the adjustments of the physiochemical conditions of the culture liquid by measuring and controlling devices, the adjustments of the pH and temperature have been exemplified. However, if necessary, controlling processes may be carried out on dissolved oxygen and ORP, and the concentration of microorganisms in the culture liquid may be further measured by an analyzer such as an on-line chemical sensor so that based on the resulting index, the physiochemical conditions may be controlled. Moreover, by using measured values under the physiochemical environment of the culture liquid obtained by the measuring and controlling devices as indexes, the load amount of medium and the speed thereof can be adjusted on demand.

A separation membrane 3 may be installed inside the membrane separation tank 2, and in the same manner as the fermentation tank 1, the shape and the like of the membrane separation tank 2 are not limited as long as a circulation line can be connected thereto. As the separation membrane 3, regardless of inorganic and organic materials to be used, any separation membranes may be used as long as only the microorganisms or culture cells can be filtered off from the culture liquid containing the microorganisms or culture cells> However, a porous membrane having appropriate separation and permeation performances in accordance with properties of the liquid to be processed and applications, which will be described later, is preferably used, and the membrane is preferably provided with resistance to sterilization (for example, at 120° C. for 30 minutes). Furthermore, the separation membrane 3 connects to a pump 4 to generate a transmembrane pressure difference between the raw liquid side and the permeation side of the separation membrane.

The membrane separation tank 2 and fermentation tank 1 are preferably designed to have such volumes as to set a culture liquid volume ratio of the culture liquid in the fermentation tank to the culture liquid in the membrane separation tank to 4 or more to 100 or less. That is, by taking it into consideration that in general, the culture liquid having about 80% of the volume of each of the membrane separation tank 2 and the fermentation tank 1 is stored therein, the tanks are desirably designed to set the ratio of the volume of the fermentation tank to the volume of the membrane separation tank to 4 or more to 100 or less. With this structure, it becomes possible to make the apparatus compact, and also to prolong the retention time of the culture liquid in the fermentation tank so that appropriate culture conditions can be achieved, power costs can be reduced, the producing speed of a chemical product is improved, and easy apparatus driving managements can be achieved.

A bypass line 26, connected to the membrane separation tank on its culture liquid flow-out side by bypassing the membrane separation tank from the culture liquid flow-in side of the membrane separation tank 2, is installed in the circulation lines (liquid transfer line 17 and liquid transfer line 15) so that, without supplying one portion of the culture liquid transferred from the fermentation tank 1 to the membrane separation tank 2, the portion of the culture liquid can be joined to the unfiltered culture liquid of the liquid transfer line 15, by bypassing the membrane separation tank 2. Additionally, in this example, one end of the bypass line 26 is connected to the liquid transfer line 17, with the other end being connected to the liquid transfer line 15. However, another structure in which the bypass line 26 connects to the fermentation tank 1 by bypassing the membrane separation tank 2 from the culture liquid flow-in side of the membrane separation tank 2, or connects to a portion between the fermentation tank 1 and the culture liquid flow-in side of the membrane separation tank 2. That is, one end (upstream side) of the bypass line 26 may connect to the liquid transfer line 17, with the other end (downstream side) being connected to the fermentation tank 1 to directly reflux the one portion of the culture liquid that has bypassed the membrane separation tank 2 to the fermentation tank 1. Alternatively, the two ends of the bypass line 26 may connect to the liquid transfer line 17 to allow the one portion of the culture liquid that has bypassed the membrane separation tank 2 to be directly joined to the culture liquid in the liquid transfer line 17 to be supplied from the fermentation tank 1.

A flowing quantity control means 25 is installed in the bypass line 26 of the membrane separation tank 2. The flowing quantity of the culture liquid to be supplied to the membrane separation tank 2 can be controlled by this flowing quantity control means. The flowing quantity control means may be prepared as either a valve or a pump, and from the viewpoint of costs, a valve is preferably used. When a valve is selected as the flowing quantity control means, the amount of the culture liquid to be supplied to the membrane separation tank 2 can be reduced by opening the valve. In contrast, by closing the valve, all the culture liquid flowing through the liquid transfer line 17 is allowed to flow into the membrane separation tank 2. Although the structure of the valve is not particularly limited, a diaphragm valve or a butterfly valve is preferably used because, upon steam sterilization, the culture liquid or the like is hardly remained because of its structure.

Moreover, when a pump is selected as the flowing quantity control means 25, a liquid transferring process can be carried out to allow the culture liquid to flow in the same direction as that of the culture liquid flowing through the membrane separation tank 2 so that by increasing the amount of the liquid transfer of the pump, the amount of the culture liquid to be supplied to the membrane separation tank 2 can be reduced, while, in contrast, by stopping the liquid transfer of the pump, all the culture liquid flowing through the liquid transfer line 17 is allowed to flow into the membrane separation tank 2.

The flowing quantity of the culture liquid to be supplied to the membrane separation tank 2 is basically controlled depending on a pressure at the culture liquid flow-in side of the membrane separation tank. For this reason, a pressure meter 29 is installed in the apparatus as shown in FIGS. 1A-1C. The pressure at the culture liquid flow-in side of the membrane separation tank is measured by the pressure meter 29, and in the case where the measured value is higher than a desired value, by activating the flowing quantity control means 25 so that one portion of the culture liquid transferred from the fermentation tank 1 is allowed to bypass the membrane separation tank 2, and circulated.

Moreover, a pump 5, which controls the flowing quantity of the culture liquid to be transferred from the fermentation tank, is installed in the circulation line. The pump may be installed in the liquid transfer line 17 or the liquid transfer line 15 (return path into the fermentation tank), and may also be installed in both of the lines. Although the system, shape and the material for a liquid contact portion thereof are not particularly limited, those pumps that are resistant to steam sterilization in the circulation line are preferably used.

Figure 6:
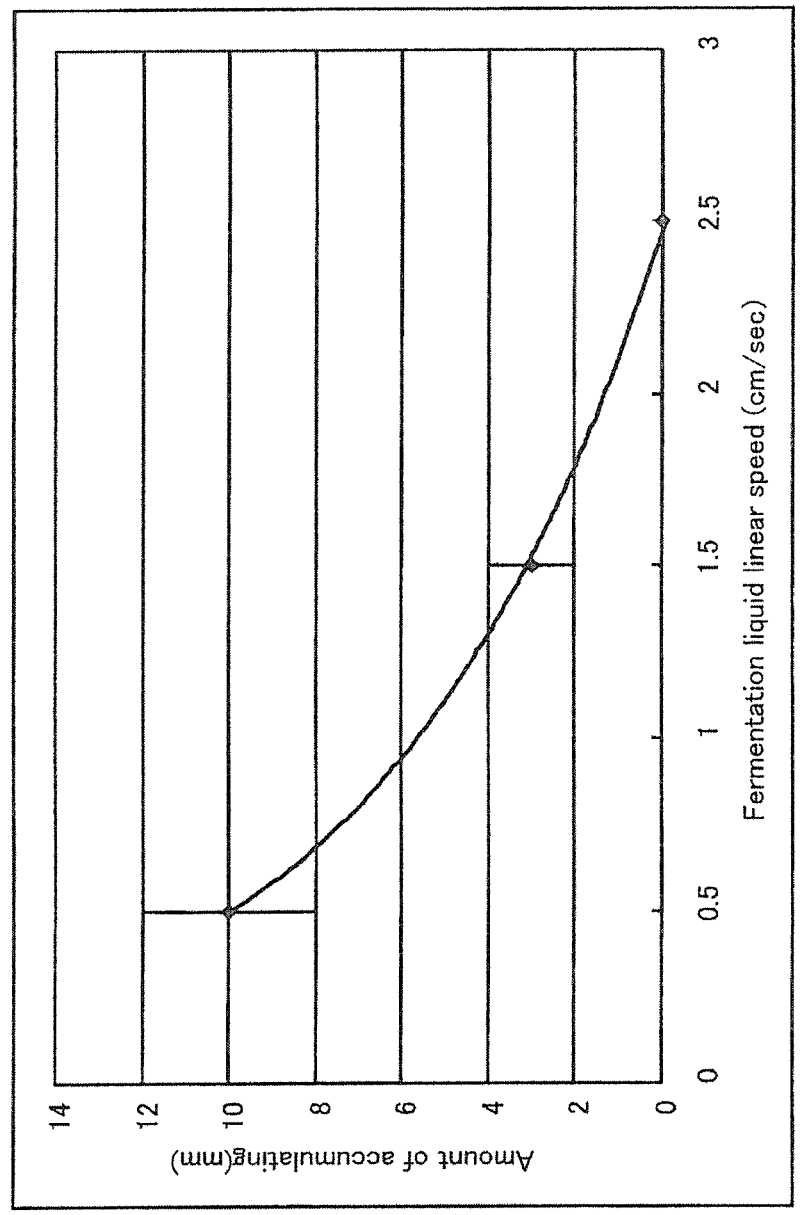
FIG. 6 is a drawing that shows a linear flow velocity of culture liquid inside a circulation line and an amount of bacteria precipitated inside the line, obtained in Example 2.

FIG. 6 shows a relationship between a culture liquid linear speed in the circulation line and an amount of precipitation of yeast strains having a lactic acid producing ability, and base upon these, we found that when the culture liquid linear speed in the circulation line (liquid transfer line 17 and liquid transfer line 15) is 2.5 cm/sec or more, the culture liquid can be circulated without allowing bacteria to be precipitated inside the pipe. Therefore, by detecting the linear flow velocity of the culture liquid inside the liquid transfer line 17 transferred from the fermentation tank and/or the unfiltered culture liquid inside the liquid transfer line 15, the flowing quantity control means 25 and the pump 5 are preferably operated to set the linear speed to 2.5 cm/sec or more. Moreover, because of the same reason, the linear speed of the culture liquid in the bypass line 26 is preferably 2.5 cm/sec or more.

Additionally, when, as described earlier, one portion of the culture liquid that has bypassed the membrane separation tank is joined to the culture liquid in the fermentation tank or to the culture liquid to be transferred from the fermentation tank to the membrane separation tank, by detecting the linear speed of the culture liquid transferred from the fermentation tank, the flowing quantity control means 25 and the pump 5 can be operated to set the linear speed to 2.5 cm/sec or more. Moreover, as will be described later, when the unfiltered culture liquid of the liquid transfer line 15 is refluxed to be joined to the culture liquid in the fermentation tank, while being refluxed to be directly joined to one portion of the culture liquid of the liquid transfer line 17, the linear speed of the culture liquid is preferably 2.5 cm/sec or more in each of the two lines. That is, each of the linear speed of the culture liquid to be transferred from the fermentation tank to the membrane separation tank, the linear speed of the unfiltered culture liquid to be refluxed from the membrane separation tank to be joined to the culture liquid on the upstream side from the membrane separation tank and the linear speed of the culture liquid to be allowed to bypass the membrane separation tank is preferably 2.5 cm/sec or more.

Moreover, in the apparatus shown in FIGS. 1A-1C, to adjust the flux in the separation membrane 3 and the amount of the culture liquid inside the fermentation tank, a level sensor 12 is installed in the fermentation tank 1. By detecting the amount of the culture liquid in the fermentation tank by the level sensor 12, the medium supply pump 6 can be controlled. To adjust the flux, the amount of filtration liquid may be controlled. Although the method of controlling the amount of the filtration liquid is not particularly limited, for example, a liquid-level pressure difference controlling device that alters the flowing quantity of the filtration liquid by controlling the liquid-level pressure difference may be installed, or the flowing quantity of the filtration liquid may be altered by driving a pump by using power of a power supply. Moreover, the fermentation apparatus to be used to produce a chemical product is preferably provided with a steam supply line used for sterilizing a fermentation tank 1, a membrane separation tank 2 and the liquid transfer lines 15 and 17.

Among various kinds of pumps to be used, for example, various pumps such as a centrifugal pump, a tube pump and a diaphragm pump, may be used, and preferably, those pumps in which the amount of circulation liquid and the amount of filtration liquid from the separation membrane can be calculated based upon the output settings of the pump may be preferably used, and more specifically, a diaphragm pump and a tube pump are desirably used.

In the method of producing a chemical product by using the fermentation apparatus having the above-mentioned structure, the culture is carried out, for example, in the following manner. In other words, microorganisms or culture cells are continuously cultivated in the fermentation tank 1, and the culture liquid is supplied to the membrane separation tank 2 from the fermentation tank 1 through the liquid transfer line 17 by the pump 5 inside the circulation line, and by causing a pressure difference between the raw liquid side and the filtration liquid side of the separation membrane 3 by a pump 4 or the like, the culture liquid is filtered so that a filtration liquid containing lactic acid or the like (chemical product) that is a fermentation product by the microorganisms or culture cells can be collected. On the other hand, an unfiltered culture liquid is refluxed into the fermentation tank 1 through the liquid transfer line 15. At this time, the flowing quantity of the pump 5 is set to such a velocity (for example, 2.5 cm/sec or more in linear flow velocity, as described earlier) as to prevent the microorganisms or culture cells from precipitating in the liquid transfer line 17 and the liquid transfer line 15.

In this case, however, when the culture and membrane-separation are continuously carried out, due to an increase in viscosity in the culture liquid and fouling of the separation membrane, as well as fouling of the flow path due to precipitated microorganisms or culture cells inside the membrane separation tank, the pressure inside the membrane separation tank is increased. When the pressure inside the membrane separation tank is increased, damages to the membrane separation tank and a load applied to the microorganisms or culture cells are increased. Therefore, the pressure inside the membrane separation tank is preferably 1 MPa or less. On the other hand, to suppress the pressure increase inside the membrane separation tank, when the amount of liquid transfer of the culture liquid from the fermentation tank 1 by the pump 5 is reduced, culture conditions inside the fermentation tank are changed greatly to cause the microorganisms and culture cells to be precipitated inside the circulation line, resulting in decrease of production efficiency.

Therefore, one portion of the culture liquid to be transferred from the fermentation tank 1 is allowed to bypass the membrane separation tank 2 and refluxed, in response to a pressure of the culture liquid at the flow-in side of the membrane separation tank 2. More preferably, the flowing quantity of the culture liquid to be allowed to bypass the membrane separation tank 2 is controlled to set the pressure of the culture liquid at the flow-in side of the membrane separation tank to 1 MPa or less. The pressure, mentioned in this case, refers to a gauge pressure and, in this disclosure, the pressure means a gauge pressure, unless otherwise specified.

The pressure fluctuations inside the membrane separation tank can be measured by the pressure meter 29 installed on the culture liquid supply side, and based upon the results of measurements, the flowing quantity of the culture liquid to be allowed to bypass the membrane separation tank is controlled so that the pressure increase inside the membrane separation tank can be controlled.

As a result, by preventing the microorganisms and culture cells inside the circulation line from being precipitated, it is possible to carry out the culture in a stable manner. Moreover, since damages to the membrane separation tank and an increased load applied to the microorganisms or culture cells can be reduced, it is possible to achieve high yield and high productivity.

In other words, in comparison with a conventional batch fermentation operation, the producing speed of the fermentation product can be increased so that a very efficient fermentation production is achieved, with the fermentation product being efficiently recovered. The production speed in the continuous culture can be calculated by equation (1):

$$\text{Chemical product producing rate (g/L·hr)} = \frac{\text{Chemical product concentration (g/L) in filtration liquid} \times \text{filtration liquid drawing rate (L/hr)}}{\text{Amount of operating liquid of apparatus (that is, total amount of culture liquid) (L)}} \quad (1)$$

Moreover, a fermentation producing speed in a batch culture is found by dividing an amount of product (g) at the time when all the material carbon source has been consumed by a time (h) required for consumption of the carbon source and the amount of culture liquid at that time (L).

Figure 2:
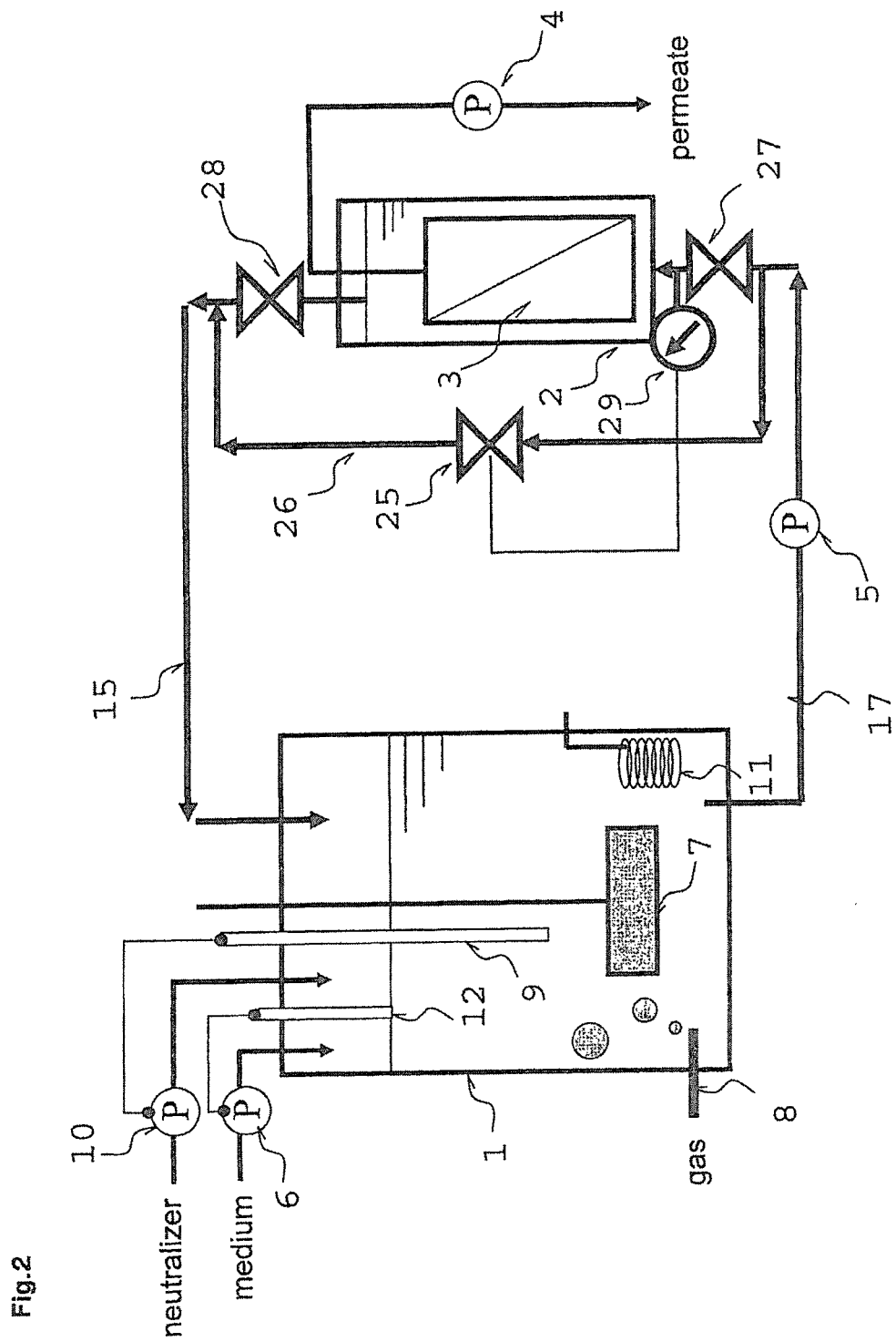
FIG. 2 is an outline schematic view that explains another example of our continuous fermentation apparatus.

The apparatus shown in FIGS. 1A-1C may be preferably revised, for example, in the following manner. That is, for example, as shown in FIG. 2, the flowing quantity control means 25 may preferably be operated in response to the results of measurements of the pressure meter 29. Moreover, a membrane separation tank open/close valve 27 may preferably be placed in the liquid transfer line 17 on the downstream side from the connected point to the bypass line 26, at a position on the upstream side from the membrane separation tank 2, or a membrane separation tank open/close valve 28 may preferably be placed in the liquid transfer line 15 on the upstream side from the connected point to the bypass line 26, at a position on the downstream side from the membrane separation tank 2. When the membrane separation tank open/close valve 27 and/or the membrane separation tank open/close valve 28 are installed, all the culture liquid flowing through the liquid transfer line 17 can be made to flow to the bypass line 26 on demand. With this arrangement, even upon occurrence of a failure inside the membrane separation tank due to fouling of the separation membrane and fouling of the flow path caused by the precipitated microorganisms or culture cells inside the membrane separation tank, the culture liquid to be supplied to the membrane separation tank can be completely stopped so that the correction of the failure inside the membrane separation tank and exchanging can be carried out.

Figure 7:
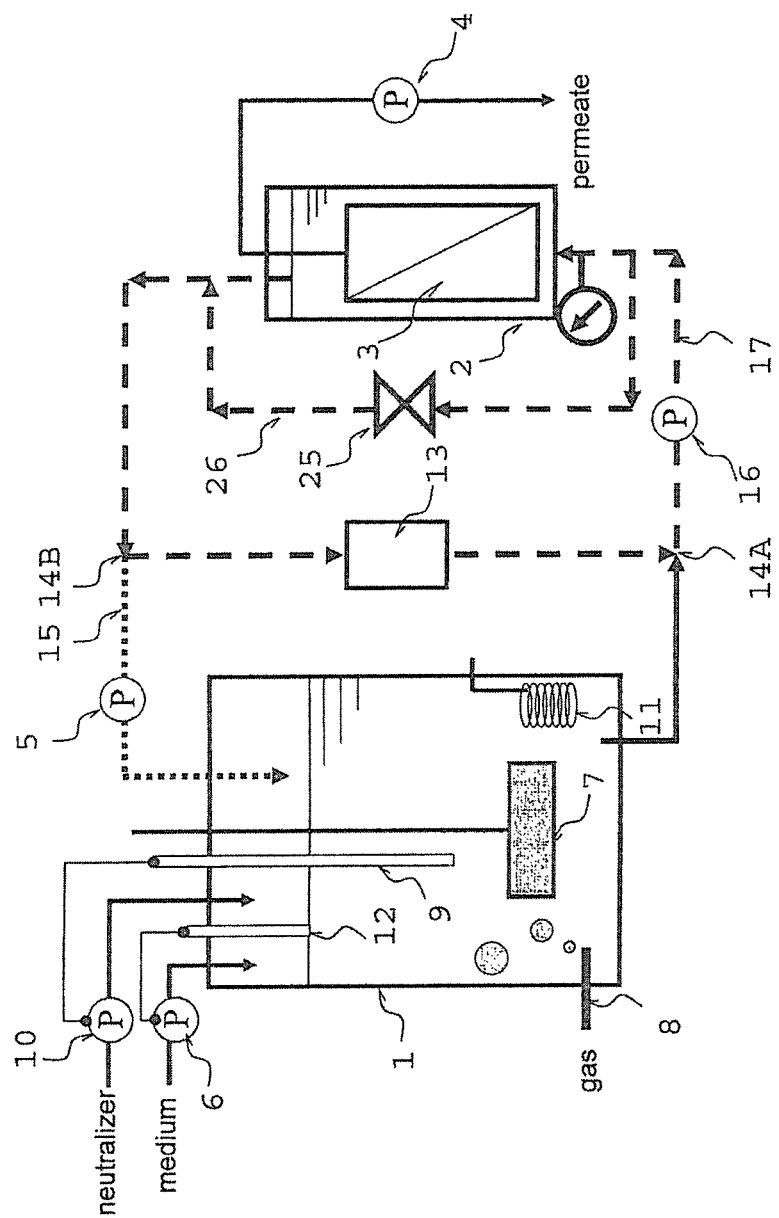
FIG. 7 is an outline schematic view that explains still another example of our continuous fermentation apparatus.

Moreover, as shown in FIG. 7, an unfiltered culture liquid of the liquid transfer line 15 is preferably refluxed to be joined to the culture liquid inside the fermentation tank, and is also preferably refluxed to be directly joined to one portion of the culture liquid of the liquid transfer line 17. At this time, the pump 5, which controls the flow velocity and flowing quantity of the unfiltered culture liquid to be refluxed to be joined to the culture liquid inside the fermentation tank, and also controls the flow velocity and flowing quantity of the culture liquid to be transferred from the fermentation tank, is placed at the downstream side closer to the fermentation tank of a branch point 14B in the liquid transfer line 15; and in a separate manner from this, a pump 16 is also placed at the downstream side of a joining point 14A in the liquid transfer line 17. With this structure, circulation circuits, which are independent from the fermentation tank 1, are formed with the downstream side of the joining point 14A in the liquid transfer line 17 and the membrane separation tank 2, as well as with the upstream side of the branch point 14B in the liquid transfer line 15. And the pumps 16 and 5 are each allowed to control the flow velocity and flowing quantity of the circulation circuit formed with the downstream side of the joining point 14A in the liquid transfer line 17 and the membrane separation tank 2, as well as with the upstream side of the branch point 14B in the liquid transfer line 15, and the flow velocity and flowing quantity of the circulation circuit formed with the downstream side of the branch point 14B in the liquid transfer line 15 and the fermentation tank 1, as well as with the upstream side of the joining point 14A in the liquid transfer line 17, in an each independent manner. For this reason, even when the flow velocity of the culture liquid inside the circulation circuit is increased by adjusting the pump 16, that is, even when the linear speed (linear flow velocity) of the culture liquid flowing on the surface of the separation membrane 3 inside the membrane separation tank is increased, the flow velocity at the downstream side of the branch point 14B in the liquid transfer line 15 can be maintained in a constant level by the pump 5 so that the velocity of the culture liquid returning into the fermentation tank 1 is maintained in a constant level. That is, since flow velocity of the culture liquid inside the membrane separation tank can be improved, with culture conditions inside the fermentation tank being maintained constantly, it is possible to maintain desirable conditions for culture in the fermentation tank, while the liquid is being transferred at a velocity that prevents the microorganisms or culture cells from being precipitated, and consequently to carry out stable culture, with high yield and high productivity being maintained.

Additionally, when the velocity of the unfiltered culture liquid to return to the fermentation tank 1 of the culture liquid becomes faster, a turbulence in the liquid current tends to be caused, with the result that the oxygen transfer coefficient kLa is influenced. Therefore, by keeping constant the velocity of the liquid returning to the fermentation tank 1 of the culture liquid, it is possible to stabilize the fermentation efficiency.

To increase the flow velocity flowing on the surface of the separation membrane 3 inside the membrane separation tank to consequently increase the production speed, with the culture efficiency being properly maintained, while the recovery amount of the resultant filtration liquid, that is, the fermentation product, is increased, the flowing quantity or flow velocity of the unfiltered culture liquid to be refluxed to be joined to the culture liquid in the fermentation tank (that is, the flowing quantity or flow velocity at the downstream side of the branch point 14B in the liquid transfer line 15) α is preferably smaller than the flowing quantity or flow velocity of the unfiltered culture liquid to be refluxed to be joined to the culture liquid between the fermentation tank and the membrane separation tank (that is, the flowing quantity or flow velocity at the downstream side of the branch point 14A in the liquid transfer line 17) β, and the ratio of these α/β is preferably 1 or less.

Figure 14:
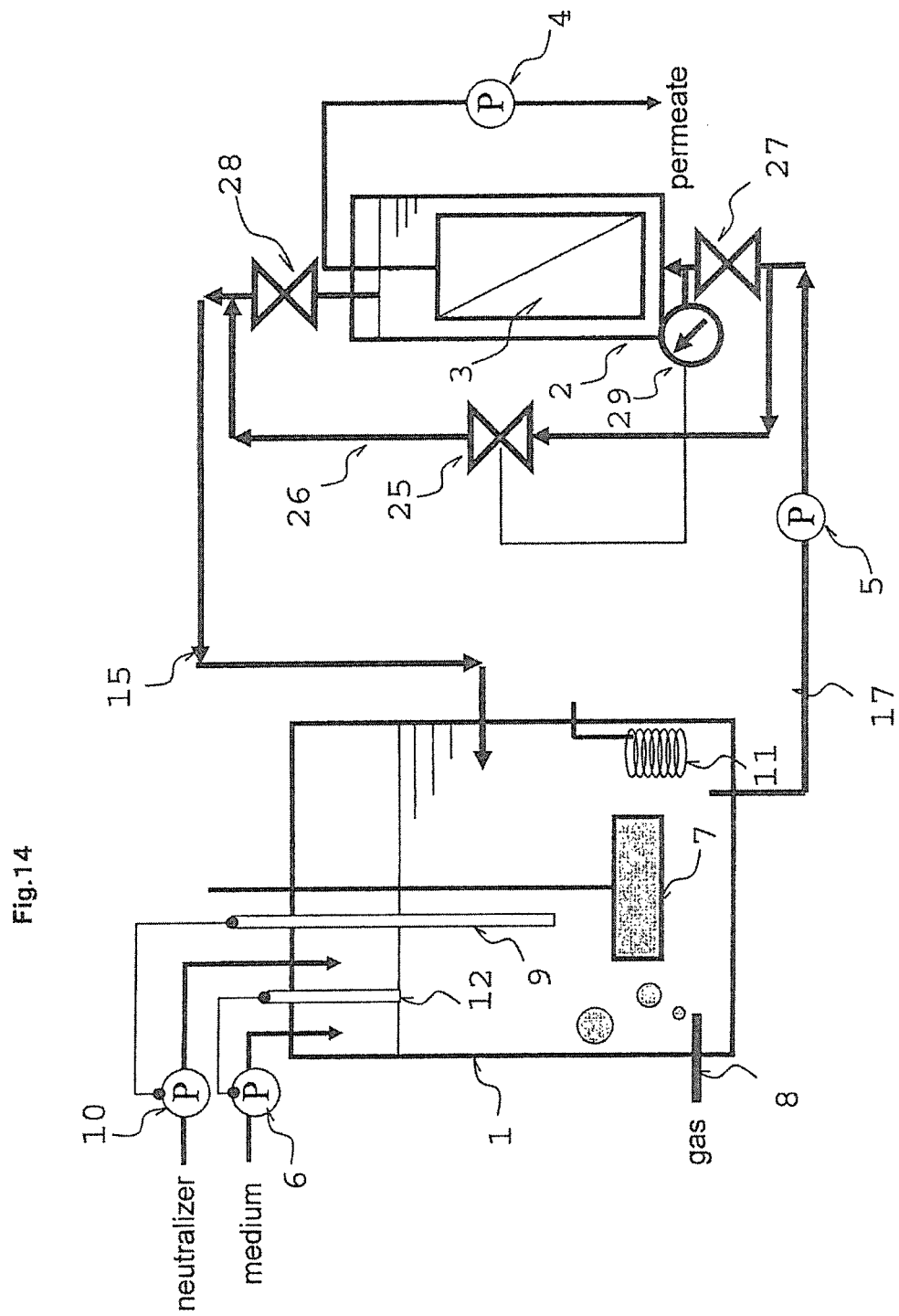
FIG. 14 is an outline schematic view that explains still another example of our continuous fermentation apparatus.

Moreover, as shown in FIG. 14, the liquid transfer line 15 used to reflux the unfiltered culture liquid to be joined to the culture liquid inside the fermentation tank preferably has an opening at a position that is immersed in the culture liquid stored in the fermentation tank 1. By allowing one of the ends of the liquid transfer line 15 to open at this position, the oxygen transfer coefficient kLa inside the fermentation tank 1 is made to be hardly fluctuated from a desired set value so that the reduction rate of the coefficient from the set value can be suppressed within 30% of the set value.

Figure 8:
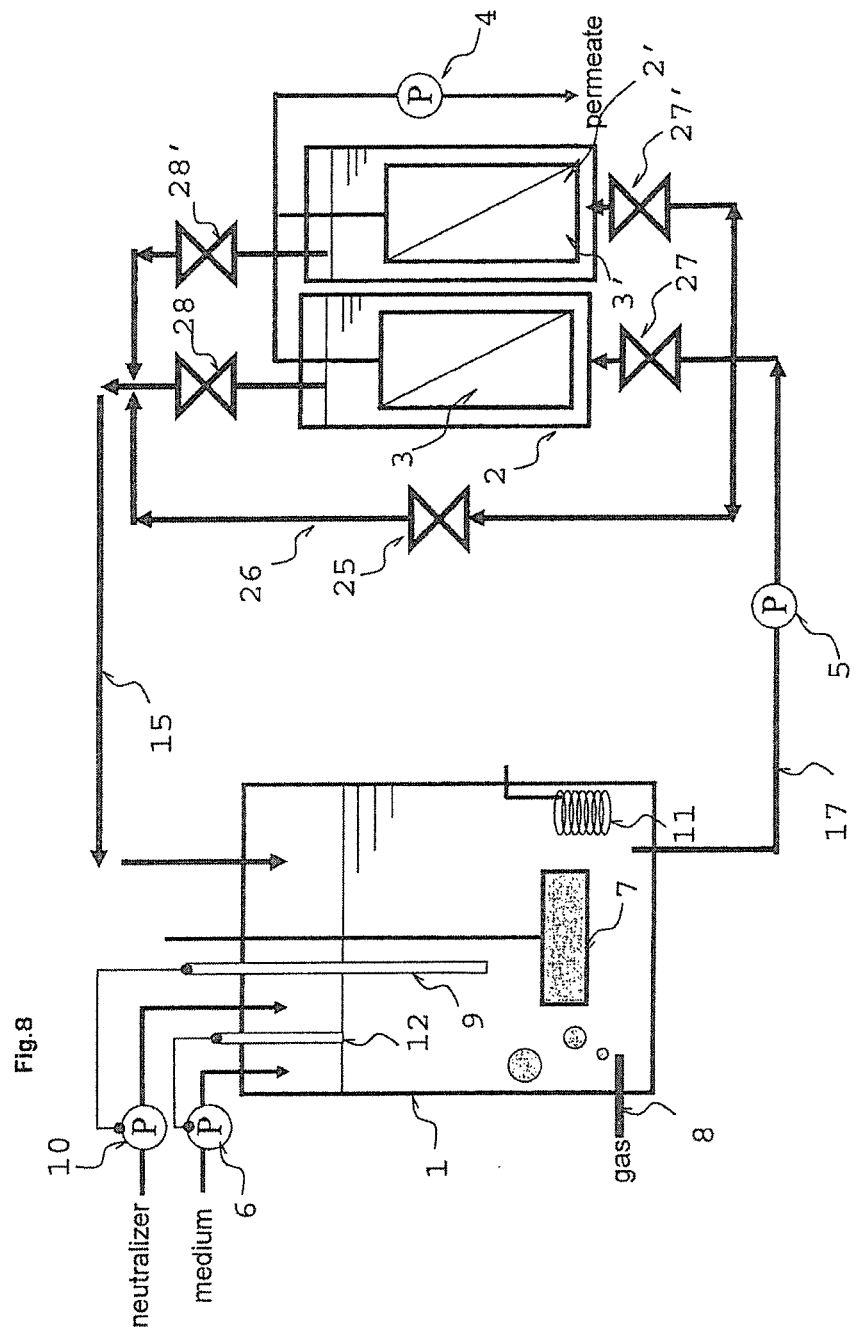
FIG. 8 is an outline schematic view that explains still another example of our continuous fermentation apparatus.

As shown in FIG. 8, a plurality of membrane separation tanks 2 are preferably connected in parallel with one another. With this arrangement, even upon occurrence of a failure inside one of the membrane separation tanks, the membrane separation tanks can be switched and properly used so that the culture can be continued without stopping the filtration inside the membrane separation tank. Moreover, when the membrane separation tanks are connected in parallel with one another, by connecting a steam supply line to the respective membrane separation tanks, sterilization can be carried out in each of the membrane separation tanks individually.

To increase the yield of the fermentation product, the fouling of the separation membrane is preferably prevented, and the continuous culture is preferably maintained for a long time stably. For these purposes, a recovery percentage that is a rate of the flowing quantity of the filtration liquid obtained from the separation membrane 3 relative to the flowing quantity of the culture liquid to be transferred to the membrane separation tank (hereinafter, sometimes, referred to simply as "recovery percentage") is preferably controlled to be 10.0% or less.

The recovery percentage refers to a ratio of the amount of filtration liquid from the separation membrane 3 to the amount of culture liquid (amount of circulated liquid) that has been transferred to the membrane separation tank per unit time, and is calculated by equation (2). When a plurality of the membrane separation tanks are connected with one another, it is calculated from the amount of filtration liquid and the amount of circulated liquid in each of the membrane separation tanks. Moreover, the amount of filtration liquid can be replaced by the separation membrane area used in the membrane separation tanks and the flux that can be drive-controlled so that equation (2) can be converted into equation (3).

$$\text{Recovery percentage of amount of filtration liquid per circulated liquid (\%)} = \frac{\text{Amount of filtration liquid (m}^3/\text{day)} \times 100}{\text{Amount of circulated liquid to membrane separation tank (m}^3/\text{day)}} \quad (2)$$

$$\text{Recovery percentage of amount of filtration liquid per circulated liquid (\%)} = \frac{\text{Area of separation membrane (m}^2) \times \text{flux (m/day)} \times 100}{\text{Amount of circulated liquid to membrane separation tank (m}^3/\text{day)}} \quad (3)$$

The amount of culture liquid to flow into the membrane separation tank and/or the amount of filtration liquid from the separation membrane can be adjusted to control the recovery percentage. That is, one or more factors, selected from the amount of circulated liquid, flux and amount of filtration liquid, are preferably controlled. Outputs of the pumps 5 and 16 located at the upstream side of the membrane separation tank, as described earlier, are preferably adjusted to control the amount of circulated liquid. As the method of controlling the flux or the amount of filtration liquid, the output adjustment of the pump 4 is preferably carried out.

Therefore, in the apparatus shown in FIGS. 1A-1C, for example, flow meters are installed in the liquid transfer line 17 and a filtration liquid draw-out line of the separation membrane 3, and by regularly monitoring the amount of circulated liquid and the amount of filtration liquid, the recovery percentage is calculated from equation (2) so that the pumps 4 and 5 are preferably driven, while the outputs thereof are being controlled to set the recovery percentage to 10.0% or less.

As the method of controlling the flux or the amount of filtration liquid, in addition to output adjustments of the pump 4, adjustments of liquid-level pressure difference, suction by a liquid, gas and the like, or a pressurization into the membrane separation tank may be proposed.

By using any of these methods, for example, a driving operation to control only the flux, with the amount of circulated liquid being maintained in a constant level, can be carried out. Moreover, a driving operation to control the amount of circulated liquid, with the flux being maintained in a constant level, can also be carried out.

The recovery percentage is preferably controlled to be 5.0% or less. From the viewpoint of enhancing the energy efficiency, the recovery percentage is as high as possible. Therefore, the lower limit of the recovery percentage is preferably at least 0.01% or more.

Next, the following description will discuss the flux. The flux can be calculated from equation (4).

$$\text{Flux} = \frac{\text{Amount of filtration liquid (m}^3/\text{day)}}{\text{Area of separation membrane (m}^2)} \quad (4)$$

It is clear that the membrane area used in the apparatus can be desirably set. The volume (m³/day) of filtration liquid amount is preferably obtained by measuring the volume of filtration liquid amount in one day. However, the volume of filtration liquid per day may be schematically calculated by measuring the volume of the amount of filtration liquid for about one hour. The flux is preferably 0.500 m/day or less, more preferably, from 0.050 m/day or more to 0.400 m/day or less. When the flux exceeds 0.500 m/day, it sometimes becomes difficult to maintain continuous culture by controlling the recovery percentage. Moreover, when the flux is less than 0.050 m/day, this fact means that the area of the separation membrane is too large, making it difficult to put into industrial use, from the economic viewpoint.

Next, the following description will discuss one example of production for a chemical product to be carried out by using the apparatus shown in FIGS. 1A-1C.

First, a microorganism and a culture raw material (medium) are stored in the fermentation tank 1, and by adding a neutralizer thereto on demand, the inside of the fermentation tank 1 is maintained from pH 4 to 8, with a temperature thereof being maintained from 20 to 50° C. With this arrangement, the culture of the microorganisms is carried out, and during the culture, desired fermentation products (chemical products) such as alcohol, an organic acid, an amino acid, a nucleic acid, and the like, are produced. During this process, as cultivation is carried out continuously for obtaining a desired fermentation product, the medium containing nutrients to be used for the culture is supplied to the fermentation tank 1 continuously or intermittently, through a medium-supply pump 6.

Moreover, simultaneously with the culture, the culture liquid inside the fermentation tank 1 is continuously circulated between the fermentation tank 1 and the membrane separation tank 2 to set a linear flow velocity inside a circulation line to 2.5 cm/sec or more by the pump 5. In the membrane separation tank 2, the culture liquid is filtered and separated into an unfiltered culture liquid containing the microorganisms and a filtration liquid containing fermentation products by using a separation membrane. As a result, the filtration liquid containing fermentation products can be taken out of the apparatus system, and by further concentrating, distilling and crystallizing the filtration liquid, a fermentation product having an enhanced purity can be obtained. On the other hand, the unfiltered culture liquid containing the microorganisms or culture cells, which has been filtered and separated, is kept inside the fermentation tank 1 so that the concentration of the microorganisms in the fermentation tank can be maintained in a high level, and the culture with high productivity of a chemical product can be carried out.

The linear flow velocity inside the circulation line can be calculated from (flowing quantity per unit time)/(cross-sectional area of pipe). Alternatively, a Coriolis' digital flow velocity sensor, or a non-contact electrode two-line type electromagnetic flow meter or the like may be connected to the pipe to carry out the measurements. By sensing the output of such a digital flow meter, the pump 5, the flowing-quantity control means 25 and the like can be controlled.

The concentration of the microorganisms or culture cells in the culture liquid in the fermentation tank 1 is preferably maintained within a high level but not to cause an inappropriate state for the growth of the microorganisms or culture cells, resulting in a higher rate of deaths of those. Thus, it is possible to obtain productivity with higher efficiency. For example, by maintaining the concentration at 5 g/L or more in dried weight, it is possible to obtain desired production efficiency.

To maintain this appropriate concentration, if necessary, the microorganisms or culture cells are preferably drawn from the fermentation tank. When the concentration of the microorganisms or culture cells inside the fermentation tank becomes too high, fouling in the separation membrane tend to be easily caused. By drawing the microorganisms or culture cells and maintaining the concentration in an appropriate level, the fouling in the separation membrane can be avoided. Moreover, since the productivity performance of a chemical product tends to be altered by the concentration of the microorganisms or culture cells in the fermentation tank, the productivity performance can be maintained within a fixed range, by drawing the microorganisms or culture cells, with the productivity performance being served as an index.

The supply of the culture raw material and the drawing of the culture liquid (liquid transfers of the culture liquid to the membrane separation tank) may be carried out from an appropriate point of time. That is, the starting times of the supply of the culture raw material and the drawing of the culture liquid are not necessarily made coincident with each other. Moreover, the supply of the culture raw material and the drawing of the culture liquid may be continuously or intermittently carried out.

Moreover, if necessary, the amount of culture liquid inside the fermentation tank may be preferably adjusted by using a level sensor 12. The adjustments of the amount of the culture liquid inside the fermentation tank can also be carried out not by measuring the level of the culture liquid in the fermentation tank, but by measuring the weight of the culture liquid.

The number of the fermentation apparatuses is not particularly limited as long as a chemical product can be generated, while microorganisms or culture cells are being grown. In general, the continuous culture operation is preferably carried out in a single fermentation tank from the viewpoint of culture managements. However, because of reasons such as a small size of the capacity of the fermentation tank, a plurality of fermentation tanks may be used. In this case, even when continuous culture is carried out, with a plurality of fermentation tanks being connected in parallel with one another, or in series with one another, by using pipes, a resulting product can be obtained with high productivity.

The culture liquid refers to a liquid obtained as a result of growth of microorganisms or culture cells in the culture raw material, and the culture raw material refers to a nutrient or the like that can accelerate the growth of microorganisms or culture cells to be cultivated, and allows a chemical product or the like that is a target product to be desirably produced. The composition of the culture raw material may be changed on demand from the culture raw material composition in the initial culture time to make the productivity of the target chemical product higher.

As the microorganisms or culture cells, examples thereof include yeast such as bread yeast, often used industrially, bacteria, such *Escherichia coli* and coryneform bacteria, filamentous fungus, Actinomycetes, animal cells and insect cells. In particular, eukaryotic organisms such as yeast, that easily causes cell destruction due to an inner pressure difference of a separated nucleus are preferably used, among these, yeast is more preferably used. Microorganisms and culture cells to be used may be separated and isolated from the natural environment, or may be those the nature of which is partially modified by mutation or gene recombination. Among these microorganisms or culture cells, those having a high producing ability for a target chemical product are preferably selected and used. The culture of microorganisms is sometimes referred to as "fermentation" or "fermentation culture."

As the culture raw material, any material may be used as long as it accelerates the growth of the microorganisms or the culture cells to be cultured and can desirably produce a target chemical product. Specific examples of the culture raw material include: a carbon source, a nitrogen source, inorganic salt and a general fluid-medium which contains organic trace-nutrients such as amino acid and vitamins, on demand.

As the carbon source, saccharides such as glucose, sucrose, fructose, galactose and lactose, starchy sugaring liquids containing these saccharides, sweet potato molasses, beet sugar molasses and hi-test-molasses may be used; moreover, organic acids such as acetic acid, alcohols such as ethanol, and glycerin may be used.

As the nitrogen source, ammonia gas, ammonia water, ammonium salts, urea, nitrate salts, and other organic nitrogen sources to be auxiliary used such as oil cakes, soybean hydrolyzation liquid, casein resolvents, other amino acids, vitamins, corn-steep-liquor, yeast or yeast extracts, meat-extracts, peptides such as peptone, and various cultivated bacteria and hydrolysates thereof may be used.

As the inorganic salts, phosphate, magnesium salt, calcium salt, iron salt, manganese salt and so on can be appropriately added. When the microorganisms need specific nutriments for its growth, the corresponding nutritious food can be added as an authentic preparation or a natural product containing it. Also, an anti-foaming agent can be used on demand.

The saccharide concentration in the culture liquid is preferably maintained to 5 g/l or less. The reason why to maintain the saccharide concentration to 5 g/l or less is desirable is to reduce the amount of saccharides that are washed away due to the drawing of the culture liquid to a minimum.

In general, the culture of microorganisms or culture cells is carried at pH 4 to 8 and at a temperature of 20 to 50° C. The pH of the culture liquid can be adjusted to a predetermined value within the above-mentioned range by using materials such as an inorganic acid or an organic acid, an alkaline material, urea, calcium carbonate and an ammonia gas. Moreover, if the speed-of-supply of oxygen needs to be raised, means such as to keep an oxygen concentration to 21% or more by adding oxygen to air, to pressurize the inside of the fermentation reaction tank, to increase stirring speed, and to increase a draft quantity, may be used.

After a concentration of microorganisms or culture cells has been increased by carrying out a Batch culture or a Fed-Batch culture in the initial stage of the culture, continuous culture may be started; or bacteria having a high concentration may be seeded, and a continuous culture may be carried out upon starting the culture.

As the chemical products (fermentation products) to be produced, not particularly limited as long as they are substances that are produced by the microorganisms or culture cells in the culture liquid, they can be selected on demand depending on the microorganisms of culture cells to be cultivated. Specific examples thereof include substances such as alcohol, organic acid, amino acid, nucleic acid and the like, that are mass produced in the fermentation industries. Examples of the alcohol include: ethanol, 1,3-propanediol, 1,4-butanediol and glycerol, examples of the organic acid include: acetic acid, lactic acid, pyruvic acid, succinic acid, malic acid, itaconic acid and citric acid, and examples of the nucleic acid include: nucleosides such as inosine and guanosine, nucleotides such as inosinic acid and guanylic acid, or diamine compounds such as cadaverine. Moreover, our methods can be applied to production of substances such as enzyme, antibiotic and recombination protein.

The following description will discuss microorganisms or culture cells used to obtain a desired chemical product, while specific chemical products are being exemplified.

As the microorganism or culture cells that can be used upon producing lactic acid, although not particularly limited, lactic acid bacteria can be desirably used. The lactic acid bacteria mentioned here is defined as the prokaryotic microorganism which produces lactic acid of 50% or more in sugar-related yield to the consumed glucose. Examples of the desirable lactic acid bacteria include any one of the genus of *LactoBacillus, Pediococcus, Tetragenococcus, Carnobacterium, Vagococcus, Leuconostoc, Oenococcus, Atopobium, Streptococcus, Enterococcus, Lactococcus,* and *Bacillus*. Among these, by selecting lactic acid bacteria that has a high sugar-related yield of lactic acid on demand, the production of lactic acid can be desirably carried out.

In addition, the lactic acid bacteria, those having a high sugar-related yield to L-lactic acid as lactic acids may be selected. The L-lactic acid is one kind of optical isomers of lactic acid, and clearly distinguished from the D-lactic acid forming an enanitomer thereto. Examples of the lactic acid bacteria having a high sugar-related yield to L-lactic acid include: *LactoBacillus yamanashiensis, LactoBacillus animalis, LactoBacillus agilis, LactoBacillus aviaries, LactoBacillus casei, LactoBacillus delbruekii, LactoBacillus paracasei, LactoBacillus rhamnosus, LactoBacillus ruminis, LactoBacillus salivarius, LactoBacillus sharpeae, Pediococcus dextrinicus, LactoBacillus lactis,* and so on, and selection can be made among these to be used for the production of L-lactic acid.

As the microorganisms or culture cells to be applicable to the production for D-lactic acid, for example, *LactoBacillus delbruekii, LactoBacillus plantarum, Pediococcus acidilactici, SporoLactoBacillus laevolacticus, SporoLactoBacillus inulinus,* and so on, may be used.

When L-lactic acid or D-lactic acid is produced, microorganisms or culture cells to which a lactic-acid producing ability is artificially added or in which such an activity is enhanced may be used. As the method for adding the lactic-acid producing ability thereto or for enhancing the lactic-acid producing ability, a known method by the use of drug mutation may be used. However, preferably, a recombinant microorganism is used. As the recombinant microorganism, those recombinant microorganisms in which the L-lactic acid or D-lactic acid producing ability is added to the microorganisms or culture cells, or enhanced therein, by introducing an L-lactic acid dehydrogenase gene (hereinafter, referred to sometimes as L-LDH) or a D-lactic acid dehydrogenase gene (hereinafter, referred to sometimes as D-DLH) thereto, are preferably used.

As the host of the above-mentioned recombinant microorganism, *Escherichia coli* which are prokaryotic cells, lactic acid bacteria and yeast, which are eukaryote, may be preferably used, and in particular, yeast is more preferably used. Among the yeasts, preferably, those belonging to a *Saccharomyces* genus are used, and more preferably, *Saccharomyces cerevisiae* may be used.

As the L-LDH or D-LDH, not particularly limited, those having an L-lactic acid dehydrogenase or a D-lactic acid hehydrogenase, which is a protein having such an activation as to convert deoxidization type nicotinamide adenine dinucleotide (NADH) and a pyruvic acid into oxidation type nicotinamide adenine dinucleotide (NAD+) and L-lactic acid or D-LDH, coded therein may be desirably used. Among these, as the L-LDH, an L-LDH derived from the

*Homo sapiens* or an L-LDH derived from the frog origin can be desirably used. Among those derived from the frog, an L-LDH derived from the frog belonging to Surinam toad (Pipidae) is desirably used, and among them, an L-LDH derived from an *Xenopus laevis* is more desirably used. Moreover, as the D-LDH, a gene, derived from *LactoBacillus plantarum* or *Pediococcus acidilactici* or *Bacillus laevolacticus*, is desirably used, and more preferably, a gene derived from *Bacillus laevolacticus* is used.

The gene of a genetic-polymorphism type and the gene of a mutagenesis type caused by mutation induction are included in L-LDH or D-LDH to be used. The gene of the genetic-polymorphism type refers to those in which one portion of the base sequence of a gene is altered because of a natural mutation on the gene. Moreover, the mutation induction refers to a process in which a mutation is artificially induced to a gene. The mutation induction is carried out by using a method in which a kit (Mutan-K, manufactured by the TAKARA BIO Inc.) for a site-directed mutation introduction is used, or a method in which a kit (BD Diversify PCR Random Mutagenesis, manufactured by (CLONTECH Inc.)) for a random mutation introduction is used.

Moreover, as the L-LDH or D-LDH to be used, even the one having a deficiency or an insertion in one portion of the base sequence can be used as long as it codes the protein having an L-lactate dehydrogenase activity or a D-lactate dehydrogenase activity.

Upon producing an L-lactic acid, the separation and purification of the L-lactic acid contained in a filtration liquid obtained from the separation membrane 3 can be carried out by combining conventionally known concentration, distillation, crystallization and so on. For example, a method in which, after the pH of the filtration liquid of the separation membrane 3 has been 1 or less, the resulting liquid is extracted by using diethyl ether, ethyl acetate and so on, or a method in which, after having been adsorbed onto an ion exchange resin and having been washed, elution is carried out thereon, a method in which, after having been reacted with alcohol in the presence of an acid catalyst, the resulting ester is distilled, and a method in which the culture liquid is crystallized and precipitated as a calcium salt or a lithium salt are proposed. Preferably, a method in which a concentrated L-lactic acid liquid obtained by evaporating moisture of the filtration liquid of the separation membrane 3 is subjected to distillation is proposed. In this case, upon distilling, the distillation is preferably carried out, while water is being supplied to keep the moisture concentration of a distillation source liquid constant. After the distillation of the L-lactic acid aqueous solution, the resulting liquid is concentrated by heating and evaporating the moisture thereof so that a purified L-lactic acid having a target concentration can be obtained. When an L-lactic acid aqueous solution having a low-boiling-point component such as ethanol and acetic acid, is obtained as a distillate, preferably, the low-boiling-point component is removed by the L-lactic acid concentration process. After the distilling operation, the distillate is subjected to the removal of an impurity by using an ion exchange resin, activated carbon, a chromatographic separation or the like so that an L-lactic acid having higher purity can be obtained.

Upon producing a D-lactic acid, in the same manner, the separation and purification of the D-lactic acid contained in a filtration liquid obtained from the separation membrane 3 can be carried out by combining conventionally known concentration, distillation, crystallization and so on. For example, a method in which, after the pH of the filtration liquid of the separation membrane 3 has been 1 or less, the resulting liquid is extracted by using diethyl ether, ethyl acetate and so on, or a method in which, after having been adsorbed onto an ion exchange resin and having been washed, elution is carried out thereon, a method in which, after having been reacted with alcohol in the presence of an acid catalyst, the resulting ester is distilled, and a method in which the culture liquid is crystallized and precipitated as calcium salt or lithium salt are proposed. Preferably, a method in which a concentrated D-lactic acid liquid obtained by evaporating moisture of the filtration liquid of the separation membrane 3 is subjected to distillation is proposed. In this case, upon distilling, the distillation is preferably carried out, while water is being supplied to keep the moisture concentration of the distilling source liquid constant. After elution of the D-lactic acid aqueous solution, the resulting liquid is concentrated by heating and evaporating the moisture thereof so that a purified D-lactic acid having a target concentration can be obtained. When a D-lactic acid aqueous solution having a low-boiling-point component (such as ethanol and acetic acid) is obtained as a distillate, preferably, the low-boiling-point component is removed by the D-lactic acid concentration process. After the distilling operation, the distillate is subjected to the removal of an impurity by using an ion exchange resin, activated carbon, a chromatographic separation or the like so that a D-lactic acid having higher purity can be obtained.

As the microorganisms or culture cells to be used upon producing ethanol, although not particularly limited, for example, yeasts belonging to any one of the genus of *Saccharomyces, Kluyveromyces* and *SchizoSaccharomyces* may be preferably used. Among these, *Saccharomyces cerevisiae, Kluyveromyces lactis*, and *SchizoSaccharomyces pombe* can be suitably used. Moreover, the bacteria which belong to the *LactoBacillus* genus or *Zymomonas* genus can also be desirably used. Among these, *LactoBacillus brevis* or *Zymomonas mobilis* can be used desirably.

The microorganisms or culture cells that can be used to produce ethanol may be microorganisms or culture cells to which an ethanol producing ability is artificially improved. More specifically, those having one portion of the nature partially modified by mutation or gene recombination may be used. One example of those having one portion of the nature modified is given as yeast in which a glucoamylase gene of a mold that belongs to *Rhizopus* genus is combined to acquire the utilizing ability of raw starch (the microorganism, 3:555-564(1987).

As the separation and purification of ethanol contained in a filtration liquid obtained from the separation membrane 3, for example, a purification method using a distillation method, and a concentration and purification method using an NF membrane or a RO membrane or a separation membrane made of zeolite can be desirably used.

As the microorganisms or culture cells to be used upon producing a pyruvic acid, although not particularly limited, for example, bacteria belonging to any one of the genus of *Pseudomonas, Coryncbacterium, Escherichia* and *Acinetobacter* can be desirably used. More desirably, bacteria of *Pseudomonas fuluorescens, Pseudomonas aeruginosa, Escherichia coli* and so on can also be used.

As the microorganisms or culture cells that can be used for producing pyruvic acid, microorganisms or culture cells to which a pyruvic-acid producing ability is artificially improved may be used, or those the nature of which is partially modified by mutation or gene recombination may be used. For example, those bacteria whose ATPase gene directly relating to ATP production by the oxidative phosphorylation is muted or removed can be desirably used. Moreover, molds, yeasts and so on may be used desirably. For example, those molds or yeasts belonging to any one of the genus of *Saccharomyces, Toluropusis, Candida* and *Schizophyllum* can be used. More preferably, the pyruvic acid can be produced by using molds or yeasts of *Saccharomyces cerevisiae, Saccharomyces copsis, Candida glabrata, Candida Toluropusis glabrata, Schizophyllum commune* and so on.

The separation and purification for a pyruvic acid contained in the filtration liquid obtained from the separation membrane 3 can be carried out by using a method in which an anion exchange column is used. For example, a purification method which uses a weak salt ion exchanger, represented by JP-A No. 6-345683, can be desirably used.

As the microorganisms or culture cells to be used upon producing a succinic acid, although not particularly limited, for example, bacteria belonging to an *Anaerobiospirillum* genus and an Actin® *Bacillus* genus can be desirably used. Specifically, *Anaerobiospirillum succiniproducens*, described in U.S. Pat. No. 5,143,833, and *ActinoBacillus succinogenes*, disclosed by James B. Mckinlay et al, are proposed (applied Microbiol. Biotechnol., 71, 6651-6656 (2005)). Moreover, coryneform bacteria belonging to the genus of *Corynebacterium, Brevibacterium* and *Escherichia coli* and so on may be utilized. As the coryneform bacteria, *Corynebacterium glutamicum, Brevibacterium flavum, Brevibacterium lactofermentum*, and so on are desirably used.

As the microorganisms or culture cells that can be used to produce succinic acid, microorganisms or culture cells to which an ethanol producing ability is artificially improved may be used. More specifically, for example, a microorganism having an improved succinic acid producing ability by gene recombination may be used, and by using this, the productivity of succinic acid can be improved. As such a microorganism, for example, *Brevibacterium flavum* MJ233AB-41 (confidence number: FERM BP-1498) having a deficiency of lactate dihydrogenase, disclosed in JP-A No. 2005-27533, *Corynebacterium glutamicum*, described in the above-mentioned non-Patent Document 1, and *Escherichia coli* AFP111 strain which is a deficit strain of Pyruvate formate-lyase and lactate dehydrogenase, described in U.S. Pat. No. 5,770,435, may be used.

The separation and purification for a succinic acid contained in the filtration liquid obtained from the separation membrane 3 can be carried out by a normal purification method for a succinic acid. For example, a purification method in which a water decomposition electrodialysis process and vacuum-concentration and crystallization are combined with each other, described in JP-A No. 2005-333886, is desirably used.

As the microorganism or culture cells that can be used to produce itaconic acid, not particularly limited, specifically, molds or yeasts are desirably used. More preferably, a producing process for an itaconic acid by using molds belonging to the genus of *Aspergillus* or *Ustilago*, or yeasts belonging to the genus of *Candida* or *Rhodotorula*, is proposed. Among these, molds such as *Aspergillus terreus, Aspergillus itaconicus, Ustilago maydis, Ustilago cynodontis*, and *Ustilago rabenhorstina*, or *Candia antarctica* can be desirably used for the production of an itaconic acid.

The separation and purification for an itaconic acid contained in the filtration liquid obtained from the separation membrane 3 is preferably carried out by using ultra-filtration and electrodialysis. For example, the ultra-filtration, which is described in JP-B No. 56-50958, or a purification method by electrodialysis in which a salt-type cation exchange resin membrane is used can be proposed.

As the microorganisms or culture cells to be used upon producing 1,3-propanediol, although not particularly limited, as native strains, specific microorganisms include those belonging to the genus *Klebsiella, Clostridium*, or *LactoBacillus*, which have an activity of synthesizing 1,3-propanediol from glycerol.

Upon producing 1,3-propanediol from glycerol, the microorganism preferably includes (a) at least one gene that codes polypeptide having a glycerol hydratase activity; (b) at least one gene that codes a glycerol hydratase reactivating factor; and (c) at least one gene that codes a non-specific catalyst activity for converting 3-hydroxy propionaldehyde into 1,3-propanediol.

More preferably, the recombinant microorganism capable of producing 1,3-propanediol from glucose is preferably used. As the host of the recombinant microorganism, those recombinant microorganisms, selected from the group consisting of: *Klebsiella* genus, *Clostridium* genus, *LactoBacillus* genus, *Cytrobacter* genus, *Enterobacter* genus, *Aerobacter* genus, *Aspergillus* genus, *Saccharomyces* genus, *SchizoSaccharomyces* genus, *ZygoSaccharomyces* genus, *Pichia* genus, *Kluyveromyces* genus, *Candida* genus, *Hansenula* genus, *Debaryomyces* genus, *Mucor* genus, *Torulopsis* genus, *Methylobacter* genus, *Salmonella* genus, *Bacillus* genus, *Aerobacter* genus, *Streptomyces* genus, *Eschericia* genus and *Pseudomonas* genus, are preferably used, and more preferably, the *Eschericia coli* is used.

The recombinant microorganism capable of producing 1,3-propanediol from glucose is preferably prepared as a recombinant microorganism containing: (a) at least one gene that codes polypeptide having a glycerol-3-phosphate dehydrogenase activity; and (b) at least one gene that codes polypeptide having a glycorol-3-phosphatase activity. More specifically, the recombinant microorganism preferably includes a gene in which the glycerol dehydratase reactivating factor is coded by orfX and orfZ isolated from dha regulon. Moreover, the recombinant microorganism is preferably prepared as a recombinant microorganism that is deficient in a glycerol kinase activity and/or a glycerol dehydrogenase activity and/or a triosephosphate isomerase activity.

The separation and purification of 1,3-propanediol contained in the filtration liquid obtained from the separation membrane 3 can be carried out by concentration and crystallization. For example, a purification method using vacuum-concentration and crystallization was desirably used.

As the microorganism or culture cells to be used upon producing cadaverine, although not particularly limited, as a specific example, those microorganisms in which enzyme activities of lysine decarboxylase and/or lysine-cadaverine antiporter, possessed by the microorganism, are enhanced are preferably used. More desirably, the recombinant microorganism, to which a gene encoding lysine decarboxylase and/or lysine-cadaverine antiporter is inserted, is proposed. Most desirably, the recombinant microorganism, to which one or two or more kinds of genes encoding lysine decarboxylase is inserted, is proposed.

Upon producing cadaverine by using a recombinant microorganism, a recombinant microorganism having *Eschericia coli* or Coryneform bacteria as a host is preferably used. More preferably, Coryneform bacteria that have a lysine decarboxylase activity and also have at least any one of homoserine auxotrophy and S-(2-aminoethyl)-L-cysteine tolerance are used. Among the coryneform bacteria, those selected from a *Cornynebacterium* genus or *Brevibacterium* genus are more preferably used, and *Corynebacterium glutamicum* is most preferably used. Moreover, the microorganism preferably has a deficiency of a homoserine dehydrogenase activity, and the deficiency of a homoserine dehydrogenase activity is preferably caused by a mutation generation due to a gene insertion.

The separation and purification of cadaverine contained in the filtration liquid obtained from the separation membrane 3 can be carried out by combining known methods such as concentration, distillation and crystallization. For example, a purification method using crystallization, as shown in JP-A No. 2004-222569, may be preferably used. Various polymer materials are prepared depending on acids to be used upon continuous fermentation and, when the application of a polymer material in which a high purity is required, the purification method using crystallization is preferably used. When the pH of the culture liquid is maintained by using hydrochloric acid, cadaverine dihydrochloride can be recovered by crystallization of the filtration liquid. More specifically, a method in which, upon continuous fermentation, the pH of the culture liquid is maintained by dicarboxylic acid so that cadaverine dicarboxylate is recovered is proposed. At this time, the carboxylic acid is preferably prepared as an aliphatic and/or aromatic dicarboxylic acid having only two carboxyl groups as functional group, and any one of acids, selected from the group consisting of: adipic acid, sebacic acid, 1,12-dodecane dicarboxylic acid, succinic acid, isophthalic acid and terephthalic acid, is more preferably used.

As the microorganisms or culture cells to be used upon producing a nucleic acid, not particularly limited, those having a high producing ability of the nucleic acid may be isolated from the natural field, or the prokaryotic microorganism whose producing ability is artificially enhanced may be used. More specifically, those the nature of which is partially modified by mutation and gene recombination may be used.

The following description will discuss the modification of one portion of the nature. To efficiently produce a nucleic acid, it is necessary to synthesize a nucleic acid to be stored, and also to excrete the resulting nucleic acid outside the cell. For this reason, by modifying the nature of microorganisms or culture cells, that is, by increasing an enzyme relating to a biosynthesis pathway of nucleic acid, by reducing an enzyme activity relating to a degradation pathway of nucleic acid, or by modifying the protein relating to excrete of nucleic acid outside the cell or the cellular membrane composition, microorganisms or culture cells that can effectively produce a nucleic acid can be prepared.

More specifically, upon producing inosine, the microorganisms and culture cells are desirably designed to have no adenylosuccinate synthetase activity or only a weak activity thereof. Moreover, they are also designed to have no inosinic acid dehydrogenase activity or only a weak activity thereof. Furthermore, they are also designed to have no nucleosidase activity or only a weak activity thereof. Upon producing guanosine, the microorganisms and culture cells are desirably designed to have no adenylosuccinate synthetase activity or only a weak activity thereof. Moreover, they are also designed to have no guanylate reductase activity or only a weak activity thereof. Furthermore, they are also desirably designed to have no nucleosidase activity or only a weak activity thereof. In addition, they are desirably designed to have no nucleotidase activity or only a weak activity thereof. Upon producing uridine, the microorganisms and culture cells are desirably designed to have no uridine phosphorylase activity or only a weak activity thereof. Upon producing cytidine, they are desirably designed to have no cytidine deaminase activity or only a weak activity thereof, and also to have no homoserine dehydrogenase or only a weak activity thereof.

As the microorganisms or culture cells to be used upon producing a nucleic acid, coryneform bacteria or *Bacillus subtilis* can be preferably used. For example, upon producing inosine, as the coryneform bacteria, bacteria belonging to a *Corynebacterium* genus are used. Among the *Corynebacterium* genus, *Corynebacterium gulutamicum*, *Corynebacterium ammoniagenes*, *Corynebacterium guanofaciens* or *Corynebacterium petrophilium* is preferably used. Moreover, as the *Bacillus subtilis*, bacteria belonging to a *Bacillus* genus are proposed, and among these, *Bacillus subtilis*, *Bacillus liqueniformis* and *Bacillus pumilus* are preferably used. Moreover, upon producing guanosine, as the Coryneform bacteria, bacteria belonging to a *Corynebacterium* genus are used, and among these, *Corynebacterium gulutamicum* is preferably used; as the as the *Bacillus subtilis*, bacteria belonging to a *Bacillus* genus are proposed, and among these, *Bacillus subtilis*, *Bacillus liqueniformis* and *Bacillus pumilus* are preferably used. Moreover, upon producing guanosine, as the Coryneform bacteria, bacteria belonging to a *Corynebacterium* genus are used, and among these, *Corynebacterium gulutamicum* is preferably used. Upon producing uridine or cytidine, among the *Bacillus subtilis*, bacteria belonging to a *Bacillus* genus are preferably used, and among these, *Bacillus subtilis* is preferably used.

Separation and purification of a nucleic acid contained in the filtration liquid obtained from the separation membrane 3 can be preferably carried out by combining known methods such as an ion exchange resin processing method, a concentration cooling crystallization method, a membrane separation method and the like, with one another. Purification may be carried out by using the known activated carbon adsorption method and recombination method to remove impurities.

Upon producing amino acid, as the corresponding amino acid, preferable examples thereof include: L-threonine, L-lysine, L-glutamic acid, L-tryptophan, L-isoleucine, L-glutamine, L-arginine, L-alanine, L-histidine, L-proline, L-phenylalanine, L-aspartic acid, L-thyrosin, methionine, serine, valine and leucine.

For example, upon producing L-threonine, as the microorganisms or culture cells, bacteria belonging to the genus *Escherichia*, *Providencia* genus, *Corynebacterium*, *Brevibacterium* or *Serratia* can be used. Among these, in particular, examples of preferable bacteria include: *Escherichia coli*, *Providencia rettgeri*, *Corynebacterium glutamicum*, *Brevibacterium flavum*, *Brevibacterium lactofermentum* and *Serratia marcescens*.

As the microorganisms or culture cells to be used upon producing L-lysine or L-glutamic acid, *Corynebacterium gulutamicum*, *Brevibacterium flavum*, or *Brevibacterium lactofermentum* are preferably used.

As the microorganisms or culture cells to be used upon producing L-tryptophan, *Corynebacterium glutamicum*, *Brevibacterium flavum*, *Brevibacterium lactofermentum*, *Bacillus subtilis*, *Bacillus amyloliquefaciens* and *Escherichia coli* can be preferably used.

As the microorganisms or culture cells to be used upon producing L-isoleucine, *Corynebacterium gulutamicum*, *Brevibacterium flavum*, *Brevibacterium lactofermentum* or *Serratia marcescens* can be preferably used.

As the microorganisms or culture cells to be used upon producing L-glutamine, *Corynebacterium gulutamicum, Brevibacterium flavum, Brevibacterium lactofermentum* or *Flavobacterium rigense* can be preferably used.

As the microorganisms or culture cells to be used upon producing L-arginine, *Corynebacterium gulutamicum, Brevibacterium flavum, Serratia marcescens, Escherichia coli* or *Bacillus subtilis* can be preferably used.

As the microorganisms or culture cells to be used upon producing L-alanine, *Brevibacterium flavum* or *Arthrobacter oxydans* can be preferably used.

As the microorganisms or culture cells to be used upon producing L-histidine, *Corynebacterium gulutamicum, Brevibacterium flavum, Brevibacterium ammoniagenes, Serratia marcescens, Escherichia coli, Bacillus subtilis* or *Streptomyces coelicolor* can be preferably used.

As the microorganisms or culture cells to be used upon producing L-proline, *Corynebacterium gulutamicum, Kurthia catenaforma, Serratia marcescens* or *Escherichia coli* can be preferably used.

As the microorganisms or culture cells to be used upon producing L-phenylalanine or L-thyrosin, *Corynebacterium gulutamicum, Brevibacterium flavum, Brevibacterium lactofermentum* or *Escherichia coli* can be preferably used.

As the microorganisms or culture cells to be used upon producing L-aspartic acid, *Brevibacterium flavum, Bacillus megatherium, Escherichia coli* or *Pseudomonas fluorescens* can be preferably used.

As the microorganisms or culture cells to be used upon producing methionine, *Corynebacterium gulutamicum* is preferably used.

As the microorganisms or culture cells to be used upon producing serine, *Corynebacterium gulutamicum, Brevibacterium flavum, Brevibacterium lactofermentum* or *Arthrobacter oxydans* can be preferably used.

As the microorganisms or culture cells to be used upon producing valine, *Brevibacterium lactofermentum, Serratia marcescens* or *Klebsiella pneumoniae* can be preferably used.

As the microorganisms or culture cells to be used upon producing leucine, *Corynebacterium gulutamicum, Brevibacterium lactofermentum* or *Serratia marcescens* can be preferably used.

As the microorganisms or culture cells to be used upon producing the above-described amino acids, those originally having a high producing ability of the amino acid may be isolated from the natural field, or the microorganisms or culture cells prepared by artificially enhancing the producing ability of the above-exemplified microorganisms or culture cells may be used. Moreover, those the nature of which is partially modified by mutation and gene recombination may be used.

As examples of the microorganism or culture cells the nature of which is partially modified, *Providencia rettgeri* whose L-threonine producing ability is improved, described in JP-A No. 2-219582, and *Corynebacterium gulutamicum* whose L-alanine producing ability is improved, described in Japanese Patent Application National Publication No. 3-500486, are given.

The following description will discuss a porous membrane that is preferably used as the separation membrane.

As the porous membrane, a porous membrane that uses an inorganic material such as ceramics, or an organic material such as a resin, as a material, may be used, and a porous separation membrane containing a porous resin layer is preferably used. This porous membrane has a structure in which a porous resin layer serving as a separation functional layer is formed on the surface of a porous base material. The porous base material is used for supporting the porous resin layer to apply strength to the separation membrane. The porous resin layer may or may not permeate the porous base material. However, from the viewpoint of strength, the membrane having the porous resin layer permeating the porous base material is preferably adopted.

The material for the porous base material is prepared as an organic material and/or an inorganic material, and among these, an organic fiber is preferably used. Preferable porous base materials are composed of fabric, non-woven fabric or the like formed by using organic fibers such as cellulose fibers, cellulose triacetate fibers, polyester fibers, polypropylene fibers and polyethylene fibers. Among these, non-woven fabric, which is easily controlled in its density and can be easily manufactured, is preferably used.

The porous resin layer functions as a separation functional layer as described above, and an organic polymer membrane is preferably used for this layer. Examples of the material for the organic polymer membrane include: polyethylene-based resin, polypropylene-based resin, polyvinyl chloride-based resin, polyvinylidene fluoride-based resin, polysulfone-based resin, polyether sulfone-based resin, polyacrylonitrile-based resin, polyolefin-based resin, cellulose-based resin and cellulose triacetate-based resin. The organic polymer membrane may be formed by a mixture mainly composed of these resins. In this case, the main component refers to a component that is contained at 50% by weight or more, preferably at 60% by weight or more. Among these, as a membrane material forming the porous resin layer, polyvinyl chloride-based resin, polyvinylidene fluoride-based resin, polysulfone-based resin, polyether sulfone-based resin, polyacrylonitrile-based resin, or polyolefin-based resin, which is easily formed into a film by using a solution, and superior in physical durability and chemical resistance, is preferably used, and polyvinylidene fluoride-based resin or polyolefin-based resin is more preferably used, and the polyvinylidene fluoride-based resin or a resin mainly composed of this is most preferably used.

As the polyvinylidene fluoride-based resin, a homopolymer of vinylidene fluoride is preferably used, and a copolymer of a vinyl-based monomer copolymerizable with vinylidene fluoride may also be preferably used. As the vinyl-based monomer copolymerizable with vinylidene fluoride, examples thereof include: tetrafluoroethylene, hexafluoropropylene, and ethylene fluoride trichloride. Moreover, as the polyolefin-based resin, polyethylene, polypropylene, chlorinated polyethylene and chlorinated polypropylene are proposed, and chlorinated polyethylene is preferably used.

The following description will discuss the outline of a method of forming a porous membrane by an example.

First, of the porous membrane, the following description will discuss the outline of a method of forming a flat membrane. The flat membrane is obtained by processes in which, after a coat film of a film-forming stock solution containing a resin and a solvent that form a porous resin layer has been formed on the surface of a porous base material, with the porous base material being impregnated with the film-forming stock solution, only the surface on the coat film side of the porous base material is made in contact with a solidifying bath containing a non-solvent to solidify the resin so that a porous resin layer is formed on the surface of the porous base material. At this time, the average thickness of the porous base material, which is selected depending on the purpose thereof, is preferably 50 µm or more to 3000 µm or less, and the average thickness of the porous base material is more preferably 20 μm or more to 5000 μm or less, most preferably, from 50 μm or more to 2000 μm or less.

Next, the following description will discuss the outline of a method of forming a hollow fiber membrane. The hollow fiber membrane is formed by processes in which a film-forming stock solution composed of a resin and a solvent that form a porous resin layer is discharged from a pipe outside of a double-pipe-type mouth piece, with a fluid to form a hollow portion being discharged from a pipe inside of the double-pipe-type mouth piece, and this is cooled and solidified in a cooling bath. At this time, the inner diameter of the hollow fiber is preferably from 200 μm or more to 5000 μm or less, and the film thickness of the porous resin layer is preferably from 20 μm or more to 2000 μm or less. Moreover, a textile or a knitted cloth having a tube shape, formed by an organic fiber or an inorganic fiber, may be contained inside the hollow fiber.

The outside surface of the hollow fiber membrane thus obtained may be coated (laminated) with another porous resin layer. Such lamination of the porous resin layer may be carried out to modify the characteristics of the hollow fiber membrane such as hydrophilic characteristic, hydrophobic characteristic, its pore diameter or the like, into desirable characteristics.

The porous resin layer to be laminated on the surface can be formed through processes in which a stock solution, formed by dissolving a resin into a solvent, is made in contact with a solidifying bath containing a non-solvent to solidify the resin. As the material for the resin to be laminated, for example, the same material as that of the porous resin layer is preferably used. Moreover, not particularly limited, the lamination method may be carried out by immersing the hollow fiber membrane in the stock solution, or may be carried out by applying the stock solution onto the surface of the hollow fiber membrane, and after the lamination, one portion of the stock solution may be scraped, or blown off by using an air knife so that the amount of lamination can be adjusted.

The porous membrane is preferably designed to have an average pore diameter from 0.01 μm or more to 1 μm or less. When the average pore diameter of the porous membrane is from 0.01 m or more to 1 μm or less, fouling due to the microorganisms used for fermentation hardly occurs so that the filtering performance can be continuously maintained for a long time. Moreover, when the average pore diameter of the porous membrane is from 0.01 μm or more to 1 μm or less, it is possible to provide a high expulsion rate that can prevent the microorganisms or culture cells from leaking, or can maintain a high water permeating property for a long time.

When the pore diameter is close to the size of the microorganisms or the culture cells, since these might directly plug the pores, the average pore diameter of the porous membrane is preferably 1 μm or less. Moreover, the average pore diameter of the porous membrane is preferably set to have a size that is not too large in comparison with the size of the microorganisms or culture cells to prevent occurrence of problems such as leakage of the microorganisms or culture cells, that is, a reduction of the expulsion rate. For this reason, in the case where, among microorganisms and culture cells, yeast, bacteria or the like whose cells are small are used, the average pore diameter is preferably 0.4 μm or less, more preferably 0.2 μm or less. The microorganisms or culture cells may tend to produce a substance other than the target chemical product, for example, proteins, polysaccharide, or the like, that are easily aggregated, or fragments of cells may tend to be generated due to deaths of the microorganisms or culture cells in the culture liquid. The average pore diameter is more preferably 0.1 μm or less to avoid fouling of the porous membrane due to these substances.

Based upon the facts described above, the average pore diameter of the porous membrane is preferably 0.4 μm or less, more preferably 0.2 μm or less, most preferably 0.1 μm or less.

In contrast, when the average pore diameter is too small, the water permeating property is lowered to cause a failure in an efficient driving process even when the membrane is not fouled so that the average pore diameter of the porous membrane is preferably 0.01 μm or more. More preferably, it is 0.02 μm or more, most preferably 0.04 μm or more.

In this case, the average pore diameter can be obtained by measuring processes in which, under a scanning-type electron microscopic observation in magnification of 10,000 times, all the diameters of pores observed within a range of 9.2 μm×10.4 μm are measured and averaged. When the pores do not form a true circle, a circle having the same area (equivalent circle) as the area possessed by each pore is found by an image processing apparatus or the like, and the diameter of the equivalent circle is defined as the diameter of the pore.

The separation membrane becomes better as the standard deviation σ of the pore diameters is made smaller, that is, it becomes better as the distribution of the sizes of the pore diameters is narrowed. The distribution of the sizes of the pore diameters is preferably narrowed so that the standard deviation is preferably 0.1 μm or less. When the standard deviation of the pore diameters is made smaller, that is, when the sizes of the pore diameters are uniformed, it is possible to obtain a filtration liquid having uniform characteristics, and also to facilitate driving managements of the apparatus.

The standard deviation σ of the pore diameters is calculated by equation (5) in which, supposing that the number of pores to be observed within the range of 9.2 μm×10.4 μm is N, with the respective diameters thus measured supposed to be $X_k$ and with the average value of the pore diameters supposed to be X(ave).

$$\sigma = \sqrt{\frac{\sum_{k=1}^{N}(X_k - X(ave))^2}{N}} \tag{5}$$

In the separation membrane, the permeability of the culture liquid containing a chemical product forms one of critical factors, and the pure-water permeability coefficient of the separation membrane before use can be used as an index for permeability. The pure-water permeability coefficient of the separation membrane is preferably $1\times10^{-10}$ m³/m²·s·Pa or more, when calculated by using purified water having a temperature of 25° C. derived from a reverse osmosis membrane, with the amount of permeated water being measured at a head height of 1 m. Moreover, to obtain a sufficient amount of filtration liquid in practical use, the pure-water permeability coefficient of the separation membrane is preferably $2\times10^{-9}$ m³/m²·s·Pa or more to $6\times10^{-7}$ m³/m²·s·Pa or less, more preferably, $2\times10^{-9}$ m³/m²·s·Pa or more to $2\times10^{-7}$ m³/m²·s·Pa or less.

The membrane surface roughness of the separation membrane forms a factor that gives influences to fouling of the separation membrane. To lower the peeling coefficient and membrane resistance of the separation membrane to produce a chemical product under a lower transmembrane pressure difference, the membrane surface roughness of the separation membrane is preferably 0.1 μm or less. The surface roughness is preferably made as small as possible to stably produce a chemical product by suppressing the fouling.

Moreover, the membrane surface roughness forms one of factors that allows microorganisms or culture cells adhered to the separation membrane surface to be easily peeled therefrom, by a membrane surface washing effect derived from a liquid flow by a stirring or a circulation pump. From these points of view as well, the membrane surface roughness of the separation membrane is made as small as possible, and is more preferably 0.1 μm or less. When the surface roughness is 0.1 μm or less, the microorganisms or culture cells adhered to the membrane can be easily peeled.

Furthermore, by setting the membrane surface roughness of the porous membrane to 0.1 μm or less, it is possible to reduce a shearing force exerted on the membrane surface upon filtration of the microorganisms or culture cells, with the result that damages to the microorganisms or the culture cells can be suppressed. As a result, fouling of the separation membrane can be suppressed so that a stable filtration process can be carried out for a long time.

In this case, the membrane surface roughness refers to an average value of fluctuations on the membrane surface in a direction perpendicular to the membrane surface direction, and as described below, this can be measured by using an atomic force microscope (AFM).

Device: Atomic force microscope (Nanoscope IIIa, manufactured by Digital Instruments Co., Ltd.)
Conditions: Probe SiN Cantilever (manufactured by Digital Instruments Co., Ltd.)
: Scanning mode Contact mode (measured in air)
Tapping mode in water (measured in water)
: Scanning range 10 μm, 25 μm in rectangular area (measured in air)
5 μm, 10 μm in rectangular area (measured in water)
: Scanning resolution 512×512
Sample preparation: Upon measuring, a membrane sample was immersed in ethanol at normal temperature for 15 minutes, and after having been immersed in RO water for 24 hours to be washed, the resultant sample was air dried and used. RO water refers to water that has been filtered by using a reverse osmosis membrane (RO membrane) that is one type of the filtration membrane so that impurities such as ions, and salts are excluded therefrom. The size of pores of the RO membrane is about 2 nm or less.

The membrane surface roughness $d_{rough}$ is calculated by equation (6), based upon the height in the Z-axis direction of each of points measured by the AFM.

$$d_{rough} = \sum_{n=1}^{N} \frac{|Z_n - \bar{Z}|}{N} \quad (6)$$

$D_{rough}$: Surface roughness(μ m)

$Z_n$: Height in Z-axis direction (μ m)

$\bar{Z}$: Average height in scanning range(μ m)

$N$: Number of measured samples

The above-mentioned separation membrane can be shaped into a desired form on demand in accordance with the shape of the membrane separation tank, and can be used.

Figure 4:
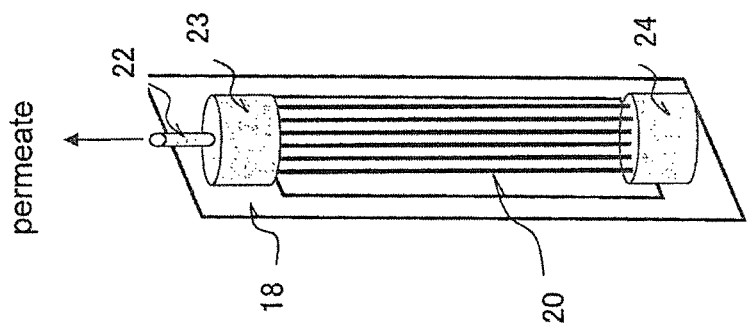
FIG. 4 is a schematic perspective view that explains another example of the separation membrane element.
Figure 3:
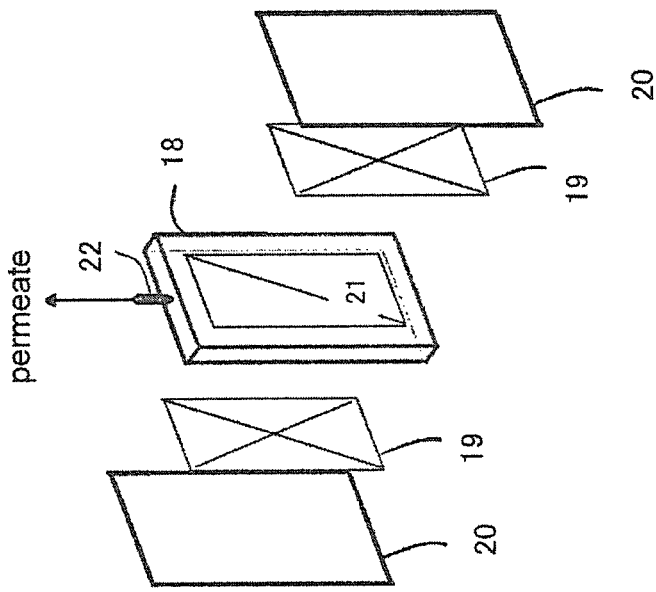
FIG. 3 is a schematic development that explains one example of a separation membrane element.

For example, in a separation membrane in a flat membrane mode, by combining it with a supporting member prepared separately, a separation membrane element, as shown in FIG. 3, can be prepared. Moreover, with respect to the hollow fiber membrane, by bonding and sealing the hollow portion by using a member made of a resin or the like, a separation membrane element, as shown in FIG. 4, can be prepared. From the viewpoint that the installation of the membrane area per volume is advantageously carried out, the hollow fiber membrane is preferably used.

Referring to drawings, the following description will discuss the outline of the separation membrane element.

FIG. 3 is a schematic perspective view that explains one example of a separation membrane element in which a separation membrane of the flat membrane mode is used. As shown in FIG. 3, the separation membrane element has a structure in which, on both surfaces of a supporting plate 18 having rigidity, a flow passage member 19 and a separation membrane 20 are placed in this order. The supporting plate 18 is provided with a concave section 21 on each of the both surfaces. The separation membrane 20 filtrates a culture liquid. The flow passage member 19 is used to allow a filtration liquid through the separation membrane 20 to efficiently flow onto the supporting plate 18. The filtration liquid containing a chemical product flowing onto the supporting plate 18, is allowed to pass through the concave section 21 of the supporting plate 18, and taken out of the continuous fermentation apparatus through a liquid collecting pipe 22 serving as a discharging means. In this case, a method utilizing a water-level pressure difference, a pump and a suction filtration by using a liquid, a gas or the like, or a method of pressurizing the inside of the apparatus system or the like can be used as a driving force for use in taking the filtration liquid out.

Additionally, when the membrane area needs to be enlarged to be fitted to the fermentation tank, these separation membrane elements may be laminated so that the membrane area can be enlarged.

FIG. 4 is a schematic perspective view showing a separation membrane element using a separation membrane of the hollow fiber mode, which is mainly constituted of a supporting plate 18, separation membranes 20 of the hollow fiber mode, an upper resin sealing layer 23 and a lower resin sealing layer 24. The separation membranes 20, which are formed into a bundle, are bonded and secured to the supporting plate 18 by the upper resin sealing layer 23 and the lower resin sealing layer 24. The hollow portion of each separation membrane 20 of the hollow fiber mode is sealed by the lower resin sealing layer 24 bonded and secured thereto so that the culture liquid is prevented from leaking. In contrast, the hollow portion of each separation membrane 20 of the hollow fiber mode is not sealed by the upper resin sealing layer 23, with the hollow portion being allowed to communicate with the liquid collecting pipe 22. This separation membrane element can be installed in the continuous fermentation apparatus by using the supporting plate 18. A filtration liquid that has been filtered through the separation membrane 20 is allowed to pass through the hollow portion of the hollow fiber membrane, and taken out of the continuous fermentation apparatus through the liquid collecting pipe 22. As a driving force for use in taking the filtration liquid out, a method utilizing a water-level pressure difference, a pump and a suction filtration by using a liquid, a gas or the like, or a method of pressurizing the inside of the apparatus system or the like can be used.

The membrane separation tank 2 provided with the separation membranes is desirably subjected to a high-pressure steam sterilization, and with this arrangement, it is possible to avoid the tank from contamination due to various bacteria. The high-pressure steam sterilization refers to a process by which microorganisms or culture cells that are present in the tank are sterilized by heating and pressurizing the membrane separation tank by using steam. As the heating and pressurizing conditions, it is preferable to pressurize and heat the tank, for example, at 121.1° C. under a steam pressure of 1 atmospheric pressure, for 20 minutes or more. Therefore, the membrane separation tank 12 of the continuous fermentation apparatus, the separation membranes placed in the membrane separation tank 12, and the element constituent members are preferably prepared as those members that are resistant to high-pressure steam sterilizing operations under these conditions. Thus, the inside of the fermentation tank including the separation membrane element can be sterilized. When the inside of the fermentation tank is kept in a sterilizable condition, it is possible to avoid risk of contamination by undesired microorganisms upon continuous fermentation, and consequently to carry out the continuous fermentation in a stable manner.

The separation membrane and members such as the supporting plate that constitute the separation membrane element are preferably made resistant to the conditions of, for example, 121.1° C. under a steam pressure of 1 atmospheric pressure, for 20 minutes or more, which are the conditions for high-pressure steam sterilizing operations, and as long as these conditions are satisfied, the kinds of the separation membrane and element constituent members are not particularly limited. As the material for the separation membrane having such resistance, the aforementioned materials for the porous membrane may be used. Moreover, as the element constituent members for the supporting plate or the like, for example, metal such as stainless steel and aluminum, or resins such as polyamide-based resin, fluorine-based resin, polycarbonate-based resin, polyacetal-based resin, polybutylene terephthalate-base resin, PVDF, modified polyphenylene ether-based resin and polysulfone-based resin, may be preferably selected and used.

EXAMPLES

Referring to examples and comparative examples, the following description will discuss our methods in detail.

More specifically, Examples 1 to 9 and Comparative Examples 1 to 4 explain continuous production for a chemical product, which is carried out by using a continuous fermentation apparatus shown in any one of FIGS. 2, 7, 9, and 13 to 16, in which L-lactic acid was selected as the chemical product, a yeast (Reference Example 1) having an L-lactic acid producing ability was used as a microorganism or culture cells, and a porous membrane (flat membrane: Reference Example 2) was selected as a separation membrane.

Moreover, Example 10 and Comparative Example 5 explain continuous production for a chemical product, which is carried out by using a continuous fermentation apparatus shown in FIG. 2, in which cadaverine (1,5-pentanediamine) was selected as the chemical product, a microorganism having a cadaverine producing ability was used as the microorganism or culture cells, and a porous membrane (flat membrane: Reference Example 2) was selected as a separation membrane.

Moreover, Example 11 and Comparative Example 6 explain continuous production for a chemical product, which is carried out by using a continuous fermentation apparatus shown in FIG. 2, in which L-lysine was selected as the chemical product, a microorganism having a L-lysine producing ability was used as the microorganism or culture cells, and a porous membrane (flat membrane: Reference Example 2) was selected as a separation membrane.

In each of the examples, a butterfly valve was used as a flowing-quantity control means 25 so that the flowing quantity and flowing pressure of a culture liquid to flow into the membrane separation tank were adjusted.

However, these examples are used for explaining some modes of this disclosure, and this disclosure is not intended to be limited to these examples.

Reference Example 1

Production of Yeast Strain (SU014 Strain) Having Lactic Acid Producing Ability

In this example, a yeast in which a L-ldh gene derived from *Xenopus Laevis* having a base sequence shown in SEQ ID NO: 1 was introduced to the downstream of a PDC1 promoter was used as the yeast having a lactic acid producing ability. The cloning of the L-ldh gene derived from the *Xenopus Laevis* was carried out by using a PCR method. In PCR, a phagemid DNA, prepared in accordance with an attached protocol of a *Xenopus Laevis* kidney cDNA library (available from STRATAGENE Corporation) was used as a mold.

In a PCR amplification reaction, KOD-Plus polymerase (available from Toyobo Co., Ltd.) was used, and attached reaction buffer, dNTPmix and the like were also used. A phagemid DNA adjusted in accordance with the attached protocol as described above was loaded in a reaction system of 50 μl to be 50 ng/sample, a primer was loaded therein to be 50 pmol/sample, and KOD-Plus polymerase was also loaded therein to be 1 unit/sample. After the reaction solution had been thermally denatured by PCR amplifier iCycler (manufactured by Bio-Rad Laboratories, Inc.) at a temperature of 94° C. for 5 minutes, the resultant solution was subjected to 30 cycles of thermal denaturation at 94° C. for 30 seconds, primer annealing at 55° C. for 30 seconds, and complimentary strand-extension at 68° C. for 1 minute, and then cooled to a temperature of 4° C. Additionally, the reaction was carried out so that, to a gene amplification primer (SEQ ID NOs: 2 and 3), a SalI recognition sequence and a NotI recognition sequence were added on the 5-terminal side and the 3-terminal side, respectively.

A PCR amplified fragment was purified, and after its terminals had been phosphorylated by a T4 polynucleotide Kinase (available from Takara Bio Inc.), the resultant fragment was ligated with a pUC118 vector (which was cut by a restriction enzyme HincII, with the cut-off surface being subjected to a dephosphorylation treatment). The ligation was carried out by using a DNA Ligation Kit Ver. 2 (available from Takara Bio Inc.). The ligation solution was transformed into competent cells of *Escherichia coli* DH5α (manufactured by Takara Bio Inc.), and these were scattered onto an LB plate containing 50 μg/mL of antibiotic substance, ampicillin, and cultivated overnight. With respect to the colony thus grown, a plasmid DNA was collected by a mini-prep kit, and cleaved by restriction enzymes SalI and NotI so that the plasmid into which an ldh gene derived from *Xenopus Laevis* was inserted was selected. A series of these operations were all carried out in accordance with the attached protocol.

Figure 5:
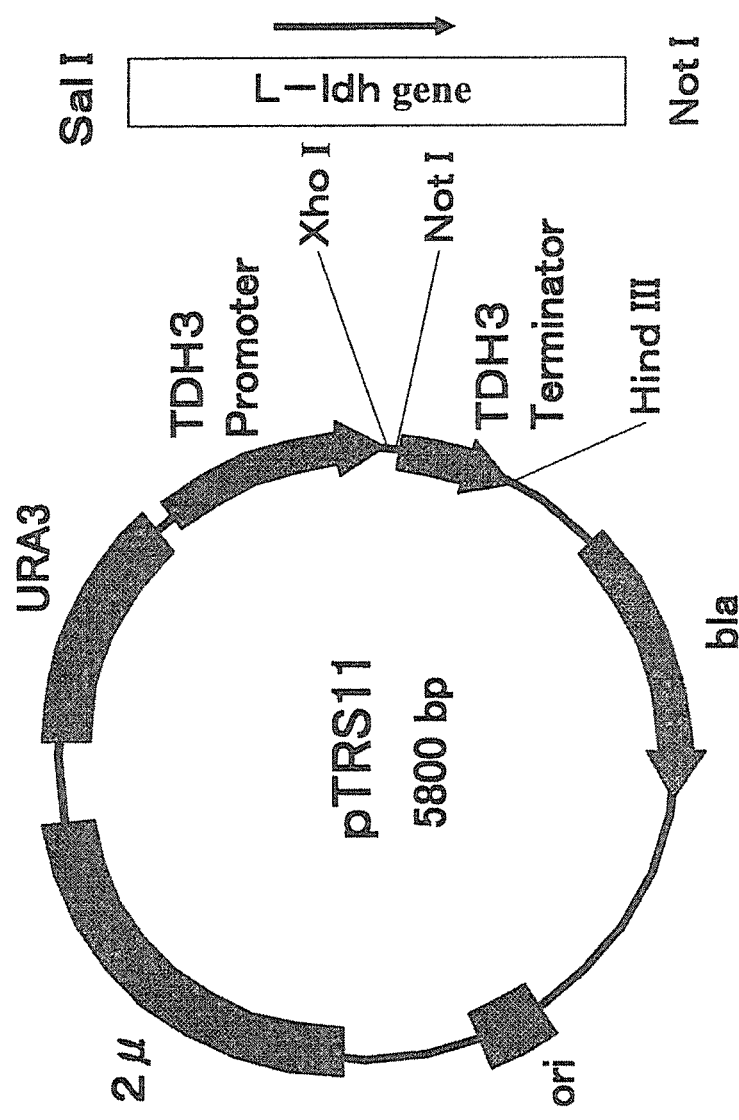
FIG. 5 is a drawing that illustrates a physical map of a yeast expression vector pTRS11 used in a reference example.

The pUC118 vector into which the L-ldh gene derived from *Xenopus Laevis* was inserted was cleaved by the restriction enzymes SalI and NotI so that the DNA fragment was separated by 1% agarose gel electrophoresis, and the fragment containing the L-ldh gene from *Xenopus Laevis* was purified by using a normal method. The fragment containing the L-ldh gene was ligated with the XhoI/NotI cleaved portion of an expression vector pTRS11, shown in FIG. 5, and by using the same method as described above, a plasmid DNA was collected, and cleaved by restriction enzymes XhoI and NotI so that the plasmid into which the ldh gene from *Xenopus Laevis* was inserted was selected. Hereinafter, the expression vector with which the L-ldh gene from *Xenopus Laevis* thus formed was combined is referred to a pTRS102.

By using this pTRS102 as an amplification mold, a 1.3 kb PCR fragment containing the L-ldh gene from *Xenopus Laevis* and a TDH3 terminator sequence was amplified by PCR in which oligonucleotide (SEQ ID NOs: 4 and 5) was used as a primer set. In this case, a sequence shown in SEQ ID NO: 4 was designed so that a sequence corresponding to 60 bp upstream from a star codon of PDC1 gene could be added.

Next, by using a plasmid pRS424 as an amplification mold, a 1.2 kb PCR fragment containing a TRP1 gene that serves as a yeast selection marker was amplified by PCR in which oligonucleotide (SEQ ID NOs: 6 and 7) was used as a primer set. In this case, a sequence shown in SEQ ID NO: 7 was designed so that a sequence corresponding to 60 bp downstream from a stop codon of PDC1 gene could be added.

The respective DNA fragments were separated by 1% agarose gel electrophoresis, and purified by using a normal method. A mixture of the 1.3 kb fragment and the 1.2 kb fragment thus obtained was used as an amplification mold, a PCR fragment of about 2.5 kb, in which the L-ldh gene from *Xenopus Laevis*, to the 5 terminal and 3 terminal of which the respective sequences corresponding to the upstream and downstream 60 bp of PDC1 gene were added, the TDH3 terminator and the TRP1 gene were coupled to one another, was amplified by a PCR method in which oligonucleotide (SEQ ID NOs: 4 and 7) was used as a primer set.

The PCR fragment was separated by 1% agarose gel electrophoresis. After purification by a normal method, the resultant fragment was transformed into a yeast *Saccharomyces cerevisiae* NBRC10505 strain, and cultivated on a tryptophan non-application medium so that a transformed strain in which the L-ldh gene from *Xenopus Laevis* was introduced to the downstream of a PDC1 gene promoter on a chromosome was selected.

The transformed strain thus obtained was confirmed to be a yeast in which the L-ldh gene from *Xenopus Laevis* was introduced to the downstream of the PDC1 gene promoter on a chromosome in the following manner. First, a genome DNA of the transformed strain was prepared by using a genome DNA extraction kit "Gentorukun" (registered trademark)(manufactured by Takara Bio Inc.), and it was confirmed that, by using this genome DNA as an amplification mold, an amplified DNA fragment of about 2.8 kb was obtained by PCR in which oligonucleotide (SEQ ID NOs: 8 and 9) was used as a primer set. Additionally, in the non-transformed strain, an amplified DNA fragment of about 2.1 kb was obtained by the above-mentioned PCR. In the following description, the transformed strain in which the L-ldh gene from *Xenopus Laevis* is introduced to the downstream of the PDC1 gene promoter on a chromosome is referred to as B2 strain. The sequences on the upstream side and the downstream side of the PDC1 gene can be obtained by *Saccharomyces* Genome Database (URL:http://www.yeastgenome.org/).

Next, yeast SW015 strain in which the pdc1 gene is substituted by a TRP1 marker, with the pdc5 gene having a temperature-sensitive mutation, described in Pamphlet of International Publication WO2007/097260, was joined to B2 strain obtained as described above so that a diploid cell was obtained. The diploid cell was formed into an ascus on an ascus formation medium. The ascus was dissected by a micromanipulator so that monoploid cells were obtained, and the auxotrophy of each monoploid cell was examined. Among the acquired monoploid cells, strains having the ldh gene from *Xenopus Laevis* inserted into the pdc1 gene locus, with the pdc5 gene being subjected to a temperature-sensitive mutation (incapable of growth at 34° C.), were selected. The yeast strain thus obtained was defined as SU014 strain.

Moreover, as to whether or not the SU014 strain had a lactic acid producing ability, measurements were carried out by an HPLC method under the following conditions to confirm whether any lactic acid is contained in the supernatant fluid of a culture medium, in which transformed cells were cultivated in an SC medium (METHODS IN YEAST GENETICS 2000 EDITION, CSHL PRESS).

Column: Shim-Pack SPR-H (manufactured by Shimadzu Corporation)
Mobile Phase: 5 mM p-toluene sulfonic acid (flow velocity: 0.8 mL/min)
Reaction Solution: 5 mM p-toluene sulfonic acid, 20 mH bis/tris, 0.1 mM EDTA.2Na (flow velocity: 0.8 mL/min)
Detection Method: Electric Conductivity
Temperature: 45° C.

Moreover, the optical purity measurements of L-lactic acid were carried by the HPLC method under the following conditions:

Column: TSK-gel Enantio LI (manufactured by Tosoh Corporation)
Mobile Phase: 1 mM Copper sulfate aqueous solution
Flow velocity: 1.0 ml/min
Detection Method: UV254 nm
Temperature: 30° C.

Additionally, the optical purity of L-lactic acid is calculated by the following equation:

$$\text{Optical Purity (\%)}=100\times(L-D)/(L+D)$$

In this case, L represents the concentration of L-lactic acid, and D represents the concentration of D-lactic acid.

As a result of the HPLC analysis, an L-lactic acid was detected, and the amount of a D-lactic acid was the detection limit or less. Based upon the above examinations, it was confirmed that this SU014 strain had a L-lactic acid producing ability.

Reference Example 2

Production of Porous Flat Membrane

By using a polyvinylidene fluoride (PVDF) resin as a resin and N,N-dimethyl acetoamide (DMAc) as a solvent, these were sufficiently stirred under a temperature of 90° C. so that the following stock solution was obtained:
PVDF: 13.0% by weight
DMAc: 87.0% by weight.

After the above-mentioned stock solutions had been cooled to a temperature of 25° C., these were applied to an nonwoven fabric (porous base material) made of polyester fibers having a density of 0.48/cm³ and a thickness of 220 µm that had been preliminarily affixed onto a glass plate, and then immediately immersed in a solidifying bath having the following composition at a temperature of 25° C. for 5 minutes so that a porous membrane, with a porous resin layer formed on the porous base material, was obtained:

Water: 30.0% by weight
DMAc: 70.0% by weight.

After the porous membrane had been peeled from the glass plate, the resultant membrane was immersed in hot water at a temperature of 80° C. three times so that DMAc was washed away, thereby obtaining a separation membrane (porous membrane). The surface of the porous resin layer within a range of 9.2 vim×10.4 µm was observed under a scanning-type electron microscope in magnification of 10,000 times, an average value of the diameters of all the pores observed was 0.1 µm. Next, the pure water filtration coefficient of the separation membrane was evaluated to obtain a value of $50 \times 10^{-9}$ m³/m²·s·Pa. The measurements of the amount of the filtered pure water were carries out by using purified water at a temperature of 25° C. derived from a reverse osmosis membrane, with a head height of 1 m. Moreover, the standard deviation of the pore diameters was 0.035 µm, and the membrane surface roughness was 0.06 µm.

Example 1

By using the SU014 strain produced in Reference Example 1, continuous fermentation was carried out by the continuous fermentation apparatus shown in FIG. 2 so that an L-lactic acid was produced. In this case, as the culture medium, a raw sugar culture medium (60 g/L Yutosei (trade name, available from Muso Co., Ltd.), 1.5 g/L ammonium sulfate) was used. This raw sugar culture medium was subjected to a steam sterilizing treatment at high pressure (2 atmospheric pressure) at a temperature of 121° C. for 15 minutes, and used. As the separation membrane element member, a molded product composed of stainless steel and polysulfone resin was used, and a porous flat membrane produced in Reference Example 2 was used as the separation membrane. As a pump 5 inside the liquid transfer line 17, a diaphragm-type pump "APLS-20" (manufactured by TACMINA Corporation) was used, and as a pump 4 to be used for drawing a filtration liquid from the membrane separation tank, a peristaltic pump was used. The driving conditions in examples were set as follows:

Capacity of fermentation tank: 20 (L)
Separation membrane to be used: PVDF filtration membrane (produced in Reference Example 2)
Capacity of membrane separation tank: 5 (L)
Effective filtration area of membrane separation element: 4000 cm²
Temperature adjustment: 32 (° C.)
Fermentation tank draft quantity: air 1 (L/min)
Stirring velocity of fermentation tank: 100 (rpm)
pH adjustment: adjusted to pH 5 by using 8N calcium hydroxide
Medium supply velocity: variably controlled by a level sensor 12 inside the fermentation tank
Sterilization: pressurized steam sterilization under 121° C. at 0.2 MPa for 20 minutes over all the membrane separation tank, fermentation tank and the medium to be used
Flowing quantity of pump 4: 3 L/hr
Maximum inner diameter of liquid transfer lines 15, 17: 50 mm
Output of pump 5: 5 L/min
Linear speed of liquid transfer line 15, 17: 4.2 cm/sec
Flux: 0.180 m/day
Recovery percentage: not controlled (1% or less).

As a pre-culture, the SU014 strain was subjected to shaking culture overnight (primary pre-culture primarily carried) on a raw sugar medium of 5 ml in a test tube. The culture liquid thus obtained was inoculated into a fresh raw sugar medium of 100 ml and subjected to, in a 500-ml Sakaguchi flask, shaking culture at 30° C. for 24 hours (pre-culture preliminarily carried out). The resultant culture liquid was inoculated into a fresh raw sugar medium of 1000 ml, and subjected to, in a 3000-ml Sakaguchi flask, shaking culture at 30° C. for 24 hours (pre-culture).

This pre-culture liquid was inoculated into a lactic acid fermentation media of total 20 L of the fermentation tank 1 and the inside of the membrane separation tank, and the inside of the fermentation tank was stirred by a stirrer attached thereto, and the draft quantity was adjusted and the temperature and the pH were adjusted, and after 50 hours culture, the pump 4 was operated so that a filtration liquid containing an L-lactic acid was drawn out. At this time, the pressure of the culture liquid to flow into the membrane separation tank 2 was measured once a day, and a flowing quantity control means 25 (butterfly valve) attached to the bypass line was adjusted so that the gauge pressure was 0.1 MPa.

Figure 10:
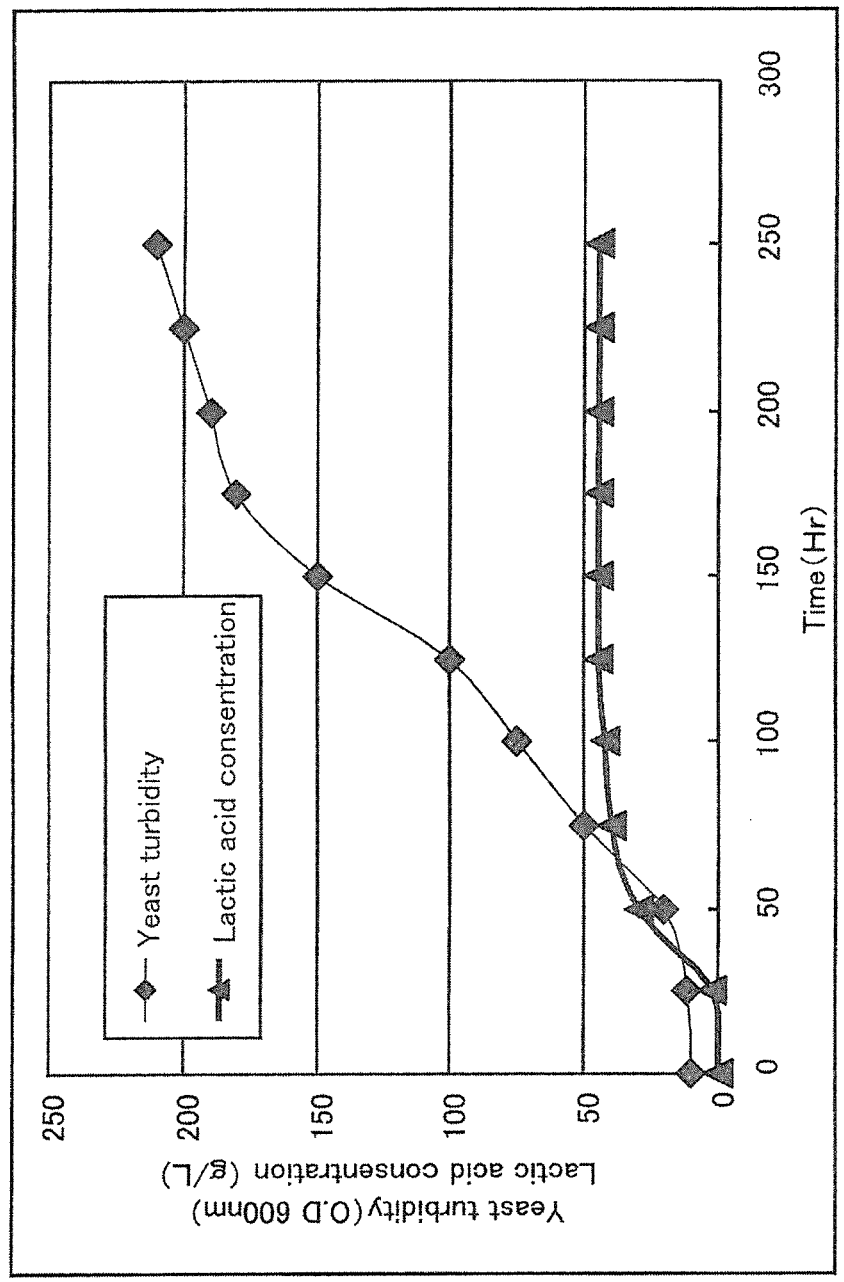
FIG. 10 is a drawing that shows a lactic acid concentration and a yeast turbidity obtained in Example 1.

After 250 hours culture, the yeast turbidity in the fermentation tank, the concentration of lactic acid as a product in the filtration liquid and the sugar concentration were measured, and the yield of lactic acid per sugar was also calculated. The results of these are shown in FIG. 10 and Table 1. Additionally, the lactic acid concentration was measured by the method shown in Reference Example 1. The yeast turbidity was measured by a photometer based upon light absorption at 600 nm. Moreover, the yield of lactic acid per sugar refers to a ratio of the weight of produced lactic acid to the weight of sugar consumed, and is calculated from equation (7):

$$\text{Yield per sugar }(\%) = \frac{\text{Produced chemical product concentration }(g/L) \times \text{amount of filtration liquid per unit of time }(L/h) \times 100}{\begin{array}{c}(\text{Sugar concentration of supplied medium }(g/L) - \\ \text{sugar concentration in filtration liquid }(g/L)) \times \\ \text{amount of filtration liquid per unit of time }(L/h)\end{array}} \quad (7)$$

The sugar concentration was measured by an HPLC method under the following conditions:

Column: Luna NH2 250×4.6 mm (manufactured by Phenomenex Co., Ltd.)
Mobile Phase: water:acetonitrile=25:75
Flow velocity: 0.6 ml/min
Detection Method: RI (differential refractometer)
Response: 4
Polarity: +
Temperature: 30° C.

Comparative Example 1

Figure 9:
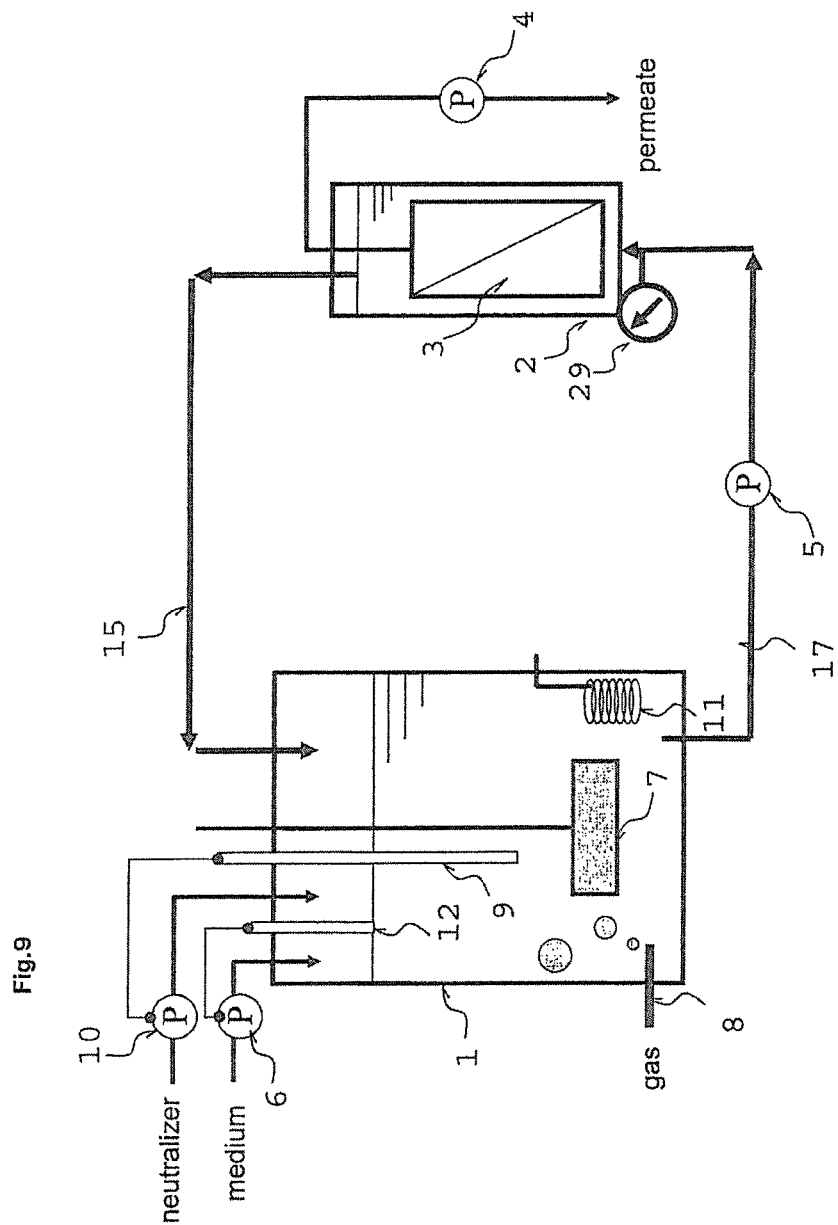
FIG. 9 is an outline schematic view that explains a mode of a continuous fermentation apparatus used in comparative examples.

Continuous fermentation was carried out in the same manner as in Example 1 except that a continuous fermentation apparatus shown in FIG. 9 was used, and the yeast turbidity and the concentration of lactic acid as a product were measured. The apparatus shown in FIG. 9 had the same structure as that of the apparatus of FIG. 2 except that the bypass line 26, the flowing quantity control means 25 and the open/close valves of the membrane separation tank 27 and 28 were not installed therein.

Figure 11:
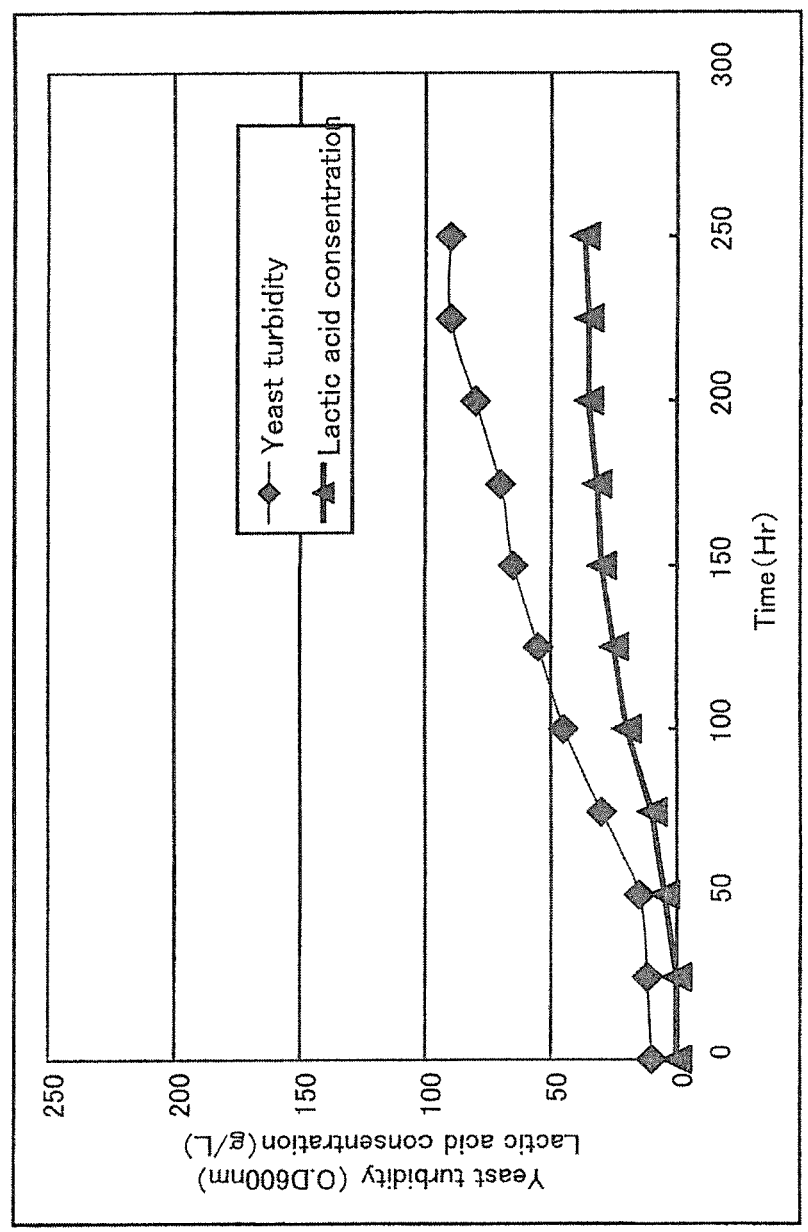
FIG. 11 is a drawing that shows a lactic acid concentration and a yeast turbidity obtained in Comparative Example 1.

The results are shown in FIG. 11 and Table 1. Moreover, the pressure of a culture liquid to be supplied to the membrane separation tank during the continuous fermentation was measured, and the results are shown in FIG. 12.

Figure 12:
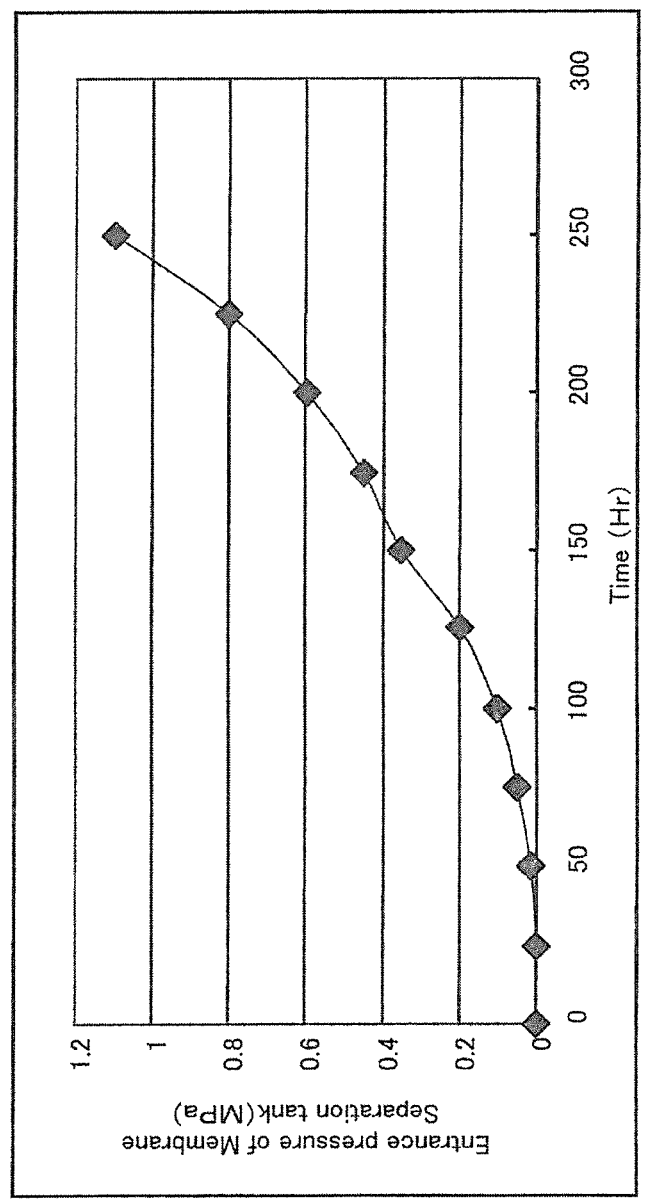
FIG. 12 is a drawing that shows a pressure of a culture liquid at the flow-in side of a membrane separation tank, obtained in Comparative Example 1.

In Comparative Example 1, since no control was carried out on the pressure of the culture liquid to be supplied to the membrane separation tank, the pressure fluctuated during the continuous fermentation, and became 1 MPa or more in 250 hours since the start of the fermentation, as shown in FIG. 12. Moreover, both of the yeast turbidity and the concentration of the produced lactic acid were lower than those of Example 1, and the yield of lactic acid per sugar was 63% after the 250 hours continuous fermentation.

As described above, by adjusting the flowing culture liquid into the membrane separation tank by the bypass line 26 and the flowing quantity control means 25 attached thereto, unexpected effects such as high concentration fermentation of yeast, improvement of the concentration of lactic acid (chemical product) and improvement of the yield of lactic acid per sugar, were confirmed.

Example 2

By using the continuous fermentation apparatus and the culture liquid after the fermentation of Example 1, the liquid was transported for 2 hours through the pipes to each set the linear flow speeds in the circulation lines to 0.5, 1.5, and 2.5 cm/see, and the amounts of accumulated bacteria that had been precipitated inside the pipes were measured. The results thereof are shown in FIG. 6. Based upon this, it can be said that, by setting the culture liquid linear speed inside the circulation lines to 2.5 cm/sec or more, it becomes possible to circulate the culture liquid, without causing bacteria to be precipitated inside the pipes.

Example 3

Continuous fermentation was carried out in the same manner as in Example 1 except that the output of the pump 5 was changed to 10 L/min, After 100 hours culture, as well as after 250 hours culture, the yeast turbidity, the concentration of lactic acid as a product in the filtration liquid and sugar concentration in the fermentation tank were measured, and the yield of the lactic acid per sugar was also calculated. The results are shown in Table 1.

In the case of Example 3, the lactic acid concentration and the yield of lactic acid pr sugar were slightly lowered in comparison with those of Example 1. This is probably because the liquid mixing state in the fermentation tank was changed due to an increase of the circulation flowing quantity (pump 5).

Comparative Example 2

Continuous fermentation was carried out in the same manner as in Example 3 except that the continuous fermentation apparatus shown in FIG. 9 was used.

Since, in Comparative Example 2, the pressure of the culture liquid to be supplied to the membrane separation tank was not controlled, the pressure inside the membrane separation tank increased during the continuous fermentation, and 70 hours after the start of the fermentation, it became 1 MPa or more. When further driven, the culture liquid started leaking from the membrane separation tank, resulting in a failure in further carrying out the continuous fermentation.

From Example 3 and Comparative Example 2, we found that no bypass line 26 would cause a failure in the continuous fermentation, and by adjusting the flowing culture liquid into the membrane separation tank by using the flowing quantity control means 25 attached to the bypass line 26, such an effect was obtained that continuous fermentation could be stably executed.

Example 4

Continuous fermentation was carried out in the same manner as in Example 3 except that a continuous fermentation apparatus shown in FIG. 7 was used, the output of the pump 5 was 5 L/min, and the output of the pump 16 was 10 L/min.

After 100 hours culture, as well as after 250 hours culture, the yeast turbidity, the concentration of lactic acid as a product in the filtration liquid and the sugar concentration in the fermentation tank were measured, and the yield of the lactic acid per sugar was also calculated. The results are shown in Table 1.

As a result, even when, in Example 1, the circulation flowing quantity was increased in the same manner as in Example 3 by the pump 16, by controlling a return flowing quantity of the liquid into the fermentation tank by the pump 16, it became possible to obtain the lactic acid concentration, the yeast turbidity and the yield of the lactic acid per sugar having the same results as those of Example 1 prior to the changing of the circulation flowing quantity.

Comparative Example 3

Figure 13:
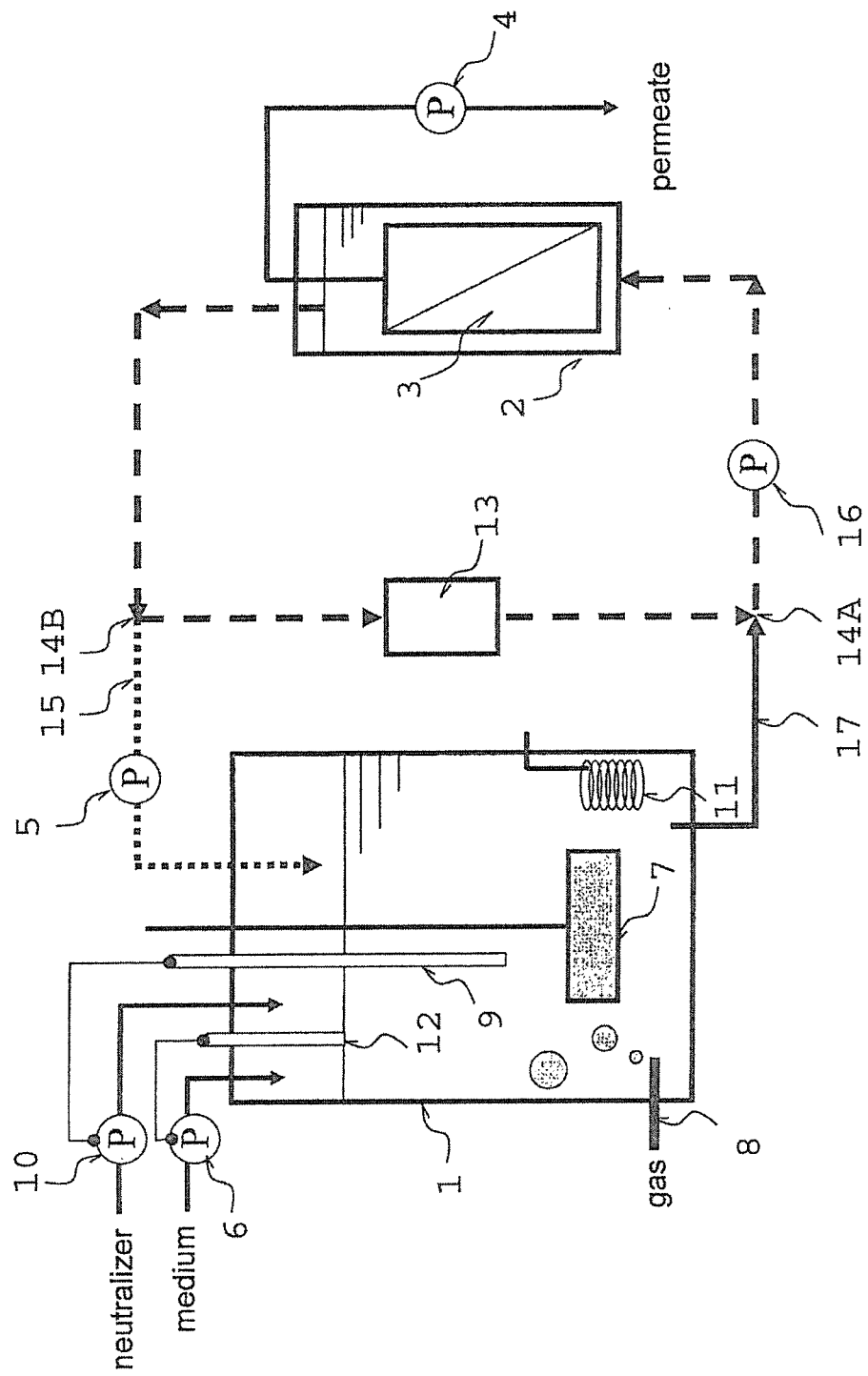
FIG. 13 is an outline schematic view that explains a mode of a continuous fermentation apparatus used in the comparative example.

Continuous fermentation was carried out in the same manner as in Example 4 except that a continuous fermentation apparatus shown in FIG. 13 was used. In this case, the apparatus shown in FIG. 13 had the same structure as that of the apparatus of FIG. 7 except that the bypass line 26, the flowing quantity control means 25 and the membrane separation valves 27 and 28 were not installed therein.

In Comparative Example 3, since no control was carried out on the pressure of the culture liquid to be supplied to the membrane separation tank, the pressure increased during the continuous fermentation, and 70 hours after the start of the culture, it became 1 MPa or more. When further driven, the culture liquid started leaking from the membrane separation tank, resulting in a failure in the continuous fermentation.

Example 5

Continuous fermentation was carried out in the same manner as in Example 3 except that a continuous fermentation apparatus shown in FIG. 14 was used. The apparatus shown in FIG. 14 had the same structure as that of the apparatus shown in FIG. 2, except that the liquid transfer line 15 was allowed to open at a position that is immersed in a culture liquid to be stored in the fermentation tank 1.

After 100 hours culture, as well as after 250 hours culture, the yeast turbidity, the concentration of lactic acid forming a product in the filtration liquid and the sugar concentration in the fermentation tank were measured, and the yield of lactic acid per sugar was also calculated. The results are shown in Table 1.

As a result, even when, in Example 1, the circulation flowing quantity was increased in the same manner as in Example 3 by the pump 5, by forming a return position of the unfiltered culture liquid at a position that was immersed in the culture liquid in the fermentation tank, it became possible to obtain the lactic acid concentration, the yeast turbidity and the yield of lactic acid per sugar having the same results as those of Example 1 prior to the changing of the circulation flowing quantity.

Comparative Example 4

Figure 15:
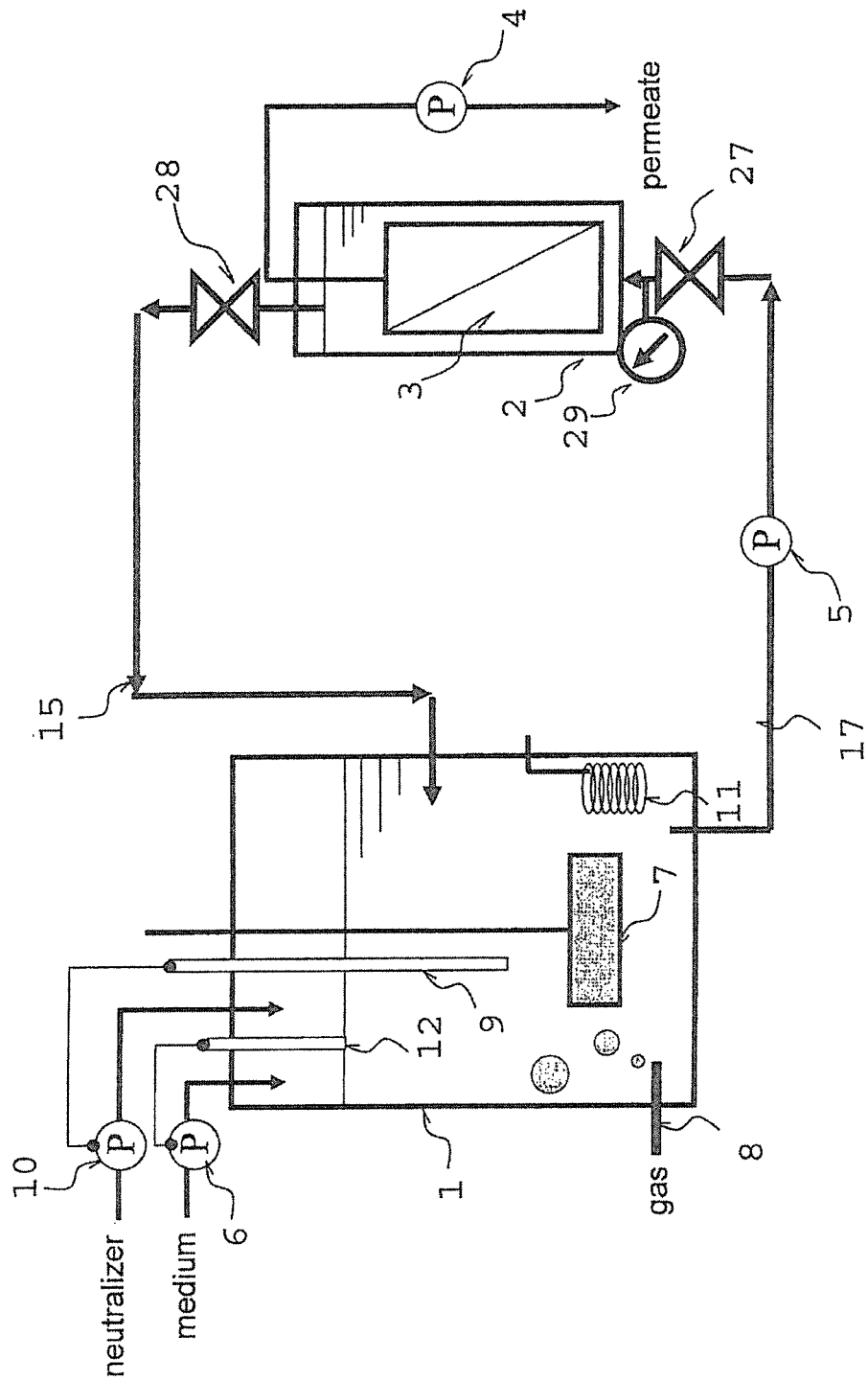
FIG. 15 is an outline schematic view that explains a mode of a continuous fermentation apparatus used in the comparative examples.

Continuous fermentation was carried out in the same manner as in Example 5 except that a continuous fermentation apparatus shown in FIG. 15 was used. In this case, the apparatus shown in FIG. 15 had the same structure as that of the apparatus of FIG. 14 except that the bypass line 26, the flowing quantity control means 25 and the membrane separation valves 27 and 28 were not installed therein.

In Comparative Example 4, since no control was carried out on the pressure of the culture liquid to be supplied to the membrane separation tank, the pressure increased during the continuous fermentation, and 70 hours after the start of the fermentation, it became 1 MPa or more. When further driven, the culture liquid started leaking from the membrane separation tank, resulting in a failure in the continuous fermentation.

Figure 17:
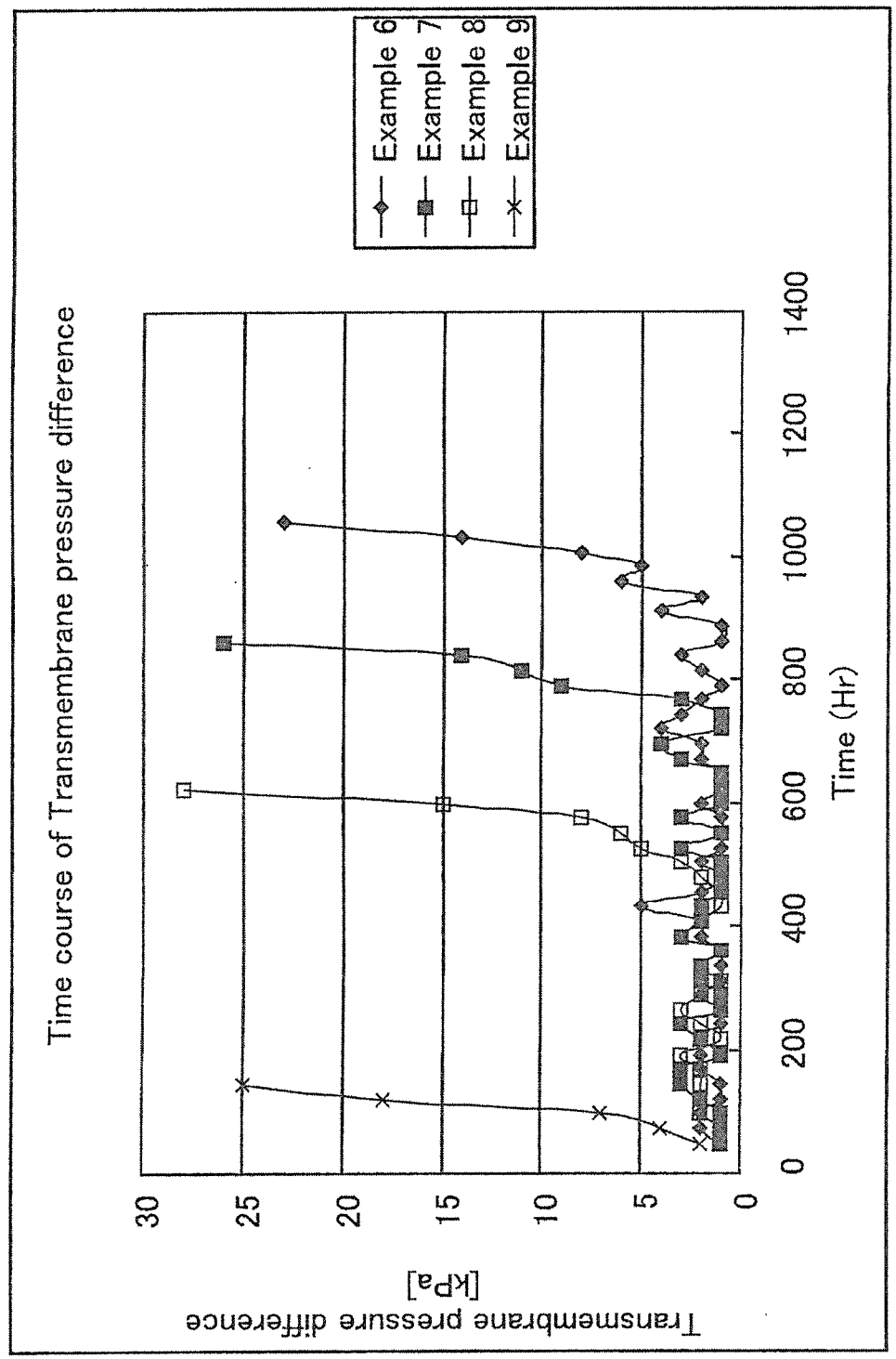
FIG. 17 is a drawing that shows a transition of transmembrane pressure differences obtained in Examples 6 to 9.

The change of the measured transmembrane pressure difference is shown in FIG. 17. Over 1000 hours from the start of the operation, the transmembrane pressure difference was kept in a stable state, and with an operation at a recovery percentage of 1.5%, L-lactic acid was produced by the continuous fermentation stably for a long time. Upon completion of the continuous fermentation, the yeast turbidity in the fermentation tank, the concentration of lactic acid as a product in the filtration liquid, the sugar concentration and the yield of lactic acid per sugar were measured and calculated, and these results are shown in Table 2.

Example 7

Continuous fermentation was carried out in the same manner as in Example 6 except that the recovery percentage was 3.0%.

The change of the measured transmembrane pressure difference is shown in FIG. 17. Over 800 hours from the start of the operation, the transmembrane pressure difference was kept in a stable state, and even under an operation at a recovery percentage of 3.0%, L-lactic acid was produced by the continuous fermentation stably for a long time. Upon completion of the continuous fermentation, the yeast turbidity in the fermentation tank, the concentration of lactic acid as a product in the filtration liquid, the sugar concentration

TABLE 1

| Example Conditions | Example 1 | | Comparative Example 1 | | Example 2 | Example 3 | | Comparative Example 2 | Example 4 | | Comparative Example 3 | Example 5 | | Comparative Example 4 |
|---|---|---|---|---|---|---|---|---|---|---|---|---|---|---|
| Chemical Product | Lactic Acid | | Lactic Acid | | Lactic Acid | Lactic Acid | | Lactic Acid | Lactic Acid | | Lactic Acid | Lactic Acid | | Lactic Acid |
| Microorganism | SU014 | | SU014 | | SU014 | SU014 | | SU014 | SU014 | | SU014 | SU014 | | SU014 |
| Apparatus | FIG. 2 | | FIG. 9 | | FIG. 2 | FIG. 2 | | FIG. 9 | FIG. 7 | | FIG. 13 | FIG. 14 | | FIG. 15 |
| Pump 4 | 3 L/hr | | 3 L/hr | | 0 L/hr | 3 L/hr | | 3 L/hr | 3 L/hr | | 3 L/hr | 3 L/hr | | 3 L/hr |
| Pump 5 | 5 L/min | | 5 L/min | | 0.6, 1.79, 2.98 L/min | 10 L/min | | 10 L/min | 5 L/min | | 10 L/min | 10 L/min | | 10 L/min |
| Pump 16 | — | | — | | — | — | | — | 10 L/min | | 5 L/min | — | | — |
| Flux | 0.180 m/day | | 0.180 m/day | | — | 0.180 m/day | | 0.180 m/day | 0.180 m/day | | 0.180 m/day | 0.180 m/day | | 0.180 m/day |
| Recovery Percentage | 1% or less | | 1% | | 0.00 | 0.5% or less | | 0.50% | 0.5% or less | | 0.50% | 0.5% or less | | 0.5% or less |
| Fermentation Time | 100 h | 250 h | 100 h | 250 h | — | 100 h | 250 h | 70 h | 100 h | 250 h | 70 h | 100 h | 250 h | 70 h |
| Compound Concentration | 45 g/L | 45 g/L | 20 g/L | 35 g/L | — | 40 g/L | 40 g/L | — | 45 g/L | 45 g/L | — | 45 g/L | 45 g/L | — |
| Microorganism Concentration | 75 | 200 | 50 | 100 | — | 60 | 180 | — | 75 | 200 | — | 75 | 200 | — |
| Yield Per Sugar | 80% | 80% | 55% | 63% | — | 72% | 72% | — | 80% | 80% | — | 80% | 80% | — |

Example 6

Figure 16:
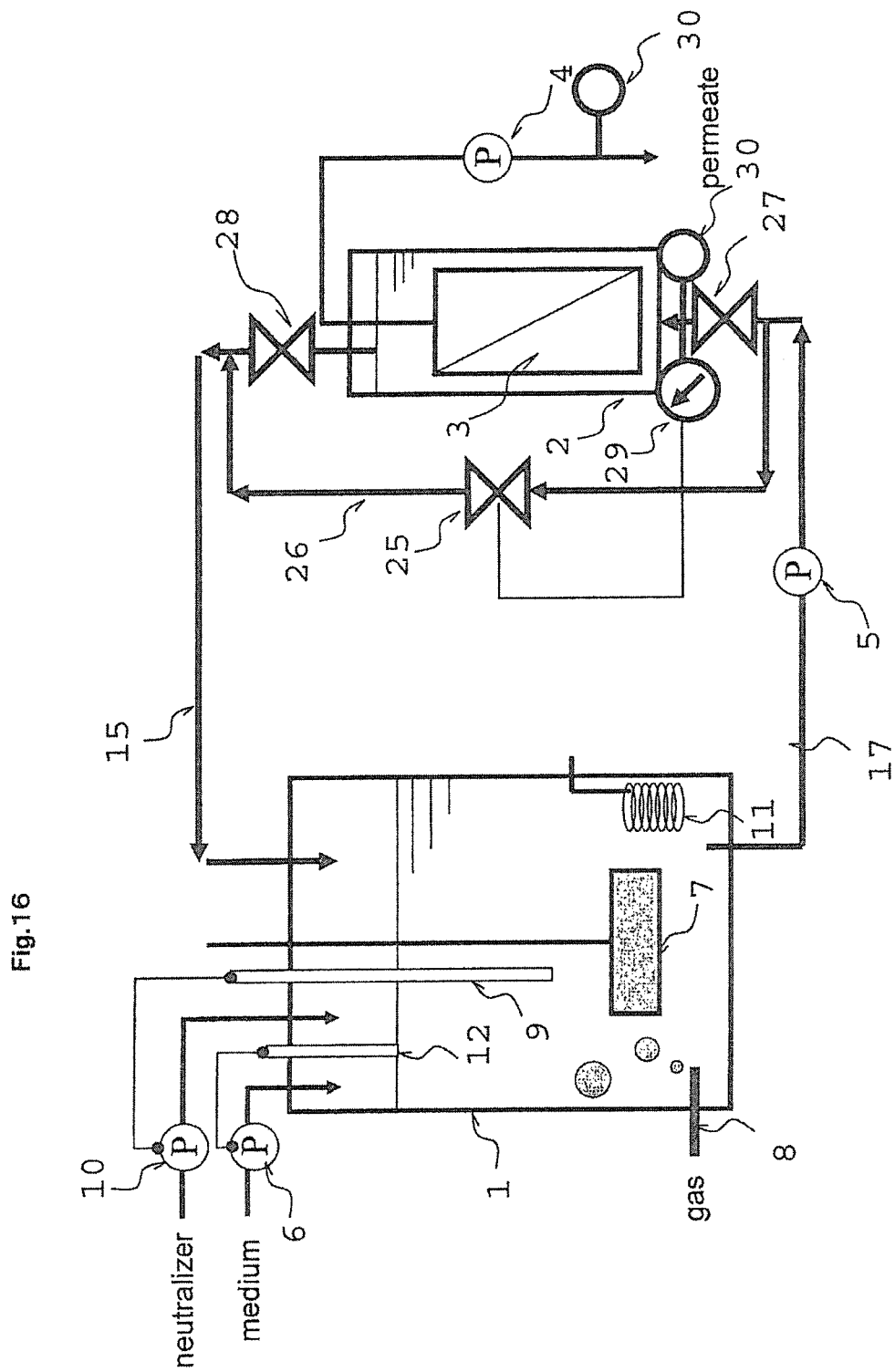
FIG. 16 is an outline schematic view that explains the other example of our continuous fermentation apparatus.

Continuous fermentation was carried out in the same manner as in Example 1 except that a continuous fermentation apparatus shown in FIG. 16 was used, the continuous fermentation was carried out while adjusting the taking-out flowing quantity of the filtration liquid by the pump 4 to set the recovery percentage calculated from the value of a flowing quantity meter 30 to 1.5%, and that, even after 250 hours, the continuous fermentation was carried out. The apparatus shown in FIG. 16 had the same structure as that of the apparatus of FIG. 2 except that the flowing quantity meter 30 was installed therein. Simultaneously, a transmembrane pressure difference, exerted on the separation membrane 3, was measured with time, and the blocked time of the membrane due to an abrupt increase of the transmembrane pressure difference was evaluated.

Example 8

Continuous fermentation was carried out in the same manner as in example except that the recovery percentage was 9.9%.

The change of the measured transmembrane pressure difference is shown in FIG. 17. Over 550 hours from the start of the operation, the transmembrane pressure difference was kept in a stable state, and even under an operation having a recovery percentage of 9.9%, L-lactic acid was produced by the continuous fermentation stably. Upon completion of the continuous fermentation, the yeast turbidity in the fermentation tank, the concentration of lactic acid as a product in the filtration liquid, the sugar concentration and the yield of lactic acid per sugar were measured and calculated, and these results are shown in Table 2.

Example 9

Continuous fermentation was carried out in the same manner as in Example 6 except that the recovery percentage was 12.0%.

The change of the measured transmembrane pressure difference is shown in FIG. 17. 100 hours after the start of the operation, the transmembrane pressure difference abruptly rose to cause a block of the pores of the membrane. Upon completion of the continuous fermentation, the yeast turbidity in the fermentation tank, the concentration of lactic acid as a product in the filtration liquid, the sugar concentration and the yield of lactic acid per sugar were measured and calculated, and these results are shown in Table 2. After 100 hours continuous fermentation, the lactic acid concentration in the fermentation tank was 45 g/L. Moreover, the yeast turbidity, OD600, is increased to 100, and the yield of lactic acid per sugar was 80%.

However, since it became difficult to carry out filtration, it difficult to continuously produce L-lactic acid by continuous fermentation over a period exceeding 100 hours.

Based upon the results of Examples 6 to 9, by carrying out a continuous fermentation operation with the recovery percentage being 10% or less, unexpected remarkable effects such as a continuous fermentation operation for a long time (500 hours or more), were confirmed.

TABLE 2

| Example Conditions | Example 6 | Example 7 | Example 8 | Example 9 |
|---|---|---|---|---|
| Chemical Product | Lactic Acid | Lactic Acid | Lactic Acid | Lactic Acid |
| Microorganism | SU014 | SU014 | SU014 | SU014 |
| Apparatus | FIG. 16 | FIG. 16 | FIG. 16 | FIG. 16 |
| Pump 4 | Fluctuated | Fluctuated | Fluctuated | Fluctuated |
| Pump 5 | 5 L/min | 5 L/min | 5 L/min | 5 L/min |
| Pump 16 | — | — | — | — |
| Flux | Fluctuated | Fluctuated | Fluctuated | Fluctuated |
| Recovery Percentage | 1.50% | 3.00% | 9.90% | 12.00% |
| Fermentation Time | 1000 h | 800 h | 550 h | 100 h |
| Compound Concentration | 45 g/L | 45 g/L | 45 g/L | 45 g/L |
| Microorganism Concentration | 320 | 270 | 250 | 100 |
| Yield Per Sugar | 80% | 80% | 80% | 80% |

Example 10

By using a *Corynebacterium glutamicum* TR-CAD1 strain described in JP-A No. 2004-222569, continuous fermentation was carried out by the continuous fermentation apparatus shown in FIG. 2 so that cadaverine was produced. As the culture medium, a cadaverine production medium having a composition shown in Table 3 was used. This cadaverine production medium was subjected to a high-pressure (2 atm) steam sterilizing treatment at 121° C. for 15 minutes, and then used. As the separation membrane element member, a molded product composed of stainless steel and a polysulfone resin was used, and as the separation membrane, the porous flat membrane, produced in Reference Example 2, was used. Moreover, as a pump 5 inside the liquid transfer line 17, a diaphragm-type pump "APLS-20" (manufactured by TACMINA Corporation) was used, and as a pump 4 to be used for drawing a filtration liquid from the membrane separation tank, a peristaltic pump was used.

TABLE 3

| Cadaverine Production Medium | |
|---|---|
| Glucose | 150 g/L |
| Citric acid | 1 g/L |
| Urea | 15 g/L |
| Potassium dihydrogen phosphate | 0.5 g/L |
| Dipotassium hydrogen phosphate | 0.5 g/L |
| Magnesium sulfate heptahydrate | 0.5 g/L |
| L-threonine | 0.8 g/L |
| L-methionine | 0.6 g/L |
| L-leucine | 1.5 g/L |
| Iron sulfate heptahydrate | 6.0 mg/L |
| Organic acid manganese monohydrate | 4.2 mg/L |
| Biotin | 1.0 mg/L |
| Thiamin | 2.0 mg/L |

Adjusted to pH 7.0 with 3M ammonium

Moreover, conditions in examples are as follows:
Fermentation tank capacity: 20 (L)
Separation membrane to be used: PVDF filtration membrane (produced in Reference Example 2)
Membrane separation tank capacity: 5 (L)
Membrane separation element effective filtration area: 4000 cm$^2$
Temperature adjustment: 30 (° C.)
Fermentation tank draft quantity: air 3 (L/min)
Stirring velocity of fermentation tank: 100 (rpm)
pH adjustment: adjusted to pH 7.0 by using 3M HCl and 3M ammonia water
Medium supply velocity: variably controlled by a level sensor inside the fermentation tank
Sterilization: pressurized steam sterilization under 121° C. at 0.2 MPa for 20 minutes over all the membrane separation tank, fermentation tank and the medium to be used
Flowing quantity of pump 4: 3 L/hr
Maximum inner diameter of liquid transfer lines 15, 17: 50 mm
Output of pump 5: 5 L/min
Linear speed of liquid transfer lines 15, 17: 4.2 cm/sec
Flux: 0.180 m/day
Recovery percentage: not controlled (1% or less).

As a pre-culture, the TR-CAD1 strain was subjected to shaking culture overnight (primary pre-culture primarily carried) on a cadaverine production medium to which 5 ml of kanamycin (25 μg/ml) was added in a test tube. The culture liquid thus obtained was inoculated into a cadaverine production medium of 50 ml to which fresh kanamycin (25 μg/ml) was added and subjected to, in a 500-ml Sakaguchi flask, shaking culture at 30° C. for 24 hours under conditions of an amplitude of 30 cm, at 180 rpm (pre-culture preliminarily carried out). The resultant culture liquid was inoculated into a fresh cadaverine production medium of 1000 ml, and subjected to, in a 3000-ml Sakaguchi flask, shaking culture at 30° C. for 24 hours (pre-culture). This pre-culture liquid was inoculated into a cadaverine production media of total 20 L of the fermentation tank 1 and the inside of the membrane separation tank, and the inside of the fermentation tank was stirred by a stirrer attached thereto, and the draft quantity, the temperature and the pH were adjusted, and after 50 hours culture, the pump 4 was operated so that a filtration liquid containing cadaverine was drawn out.

At this time, the pressure of the culture liquid to flow into the membrane separation tank 2 was measured once a day, and the flowing quantity control means 25 (butterfly valve) attached to the bypass line 26 was adjusted so that the gauge pressure was 0.1 MPa.

Figure 18:
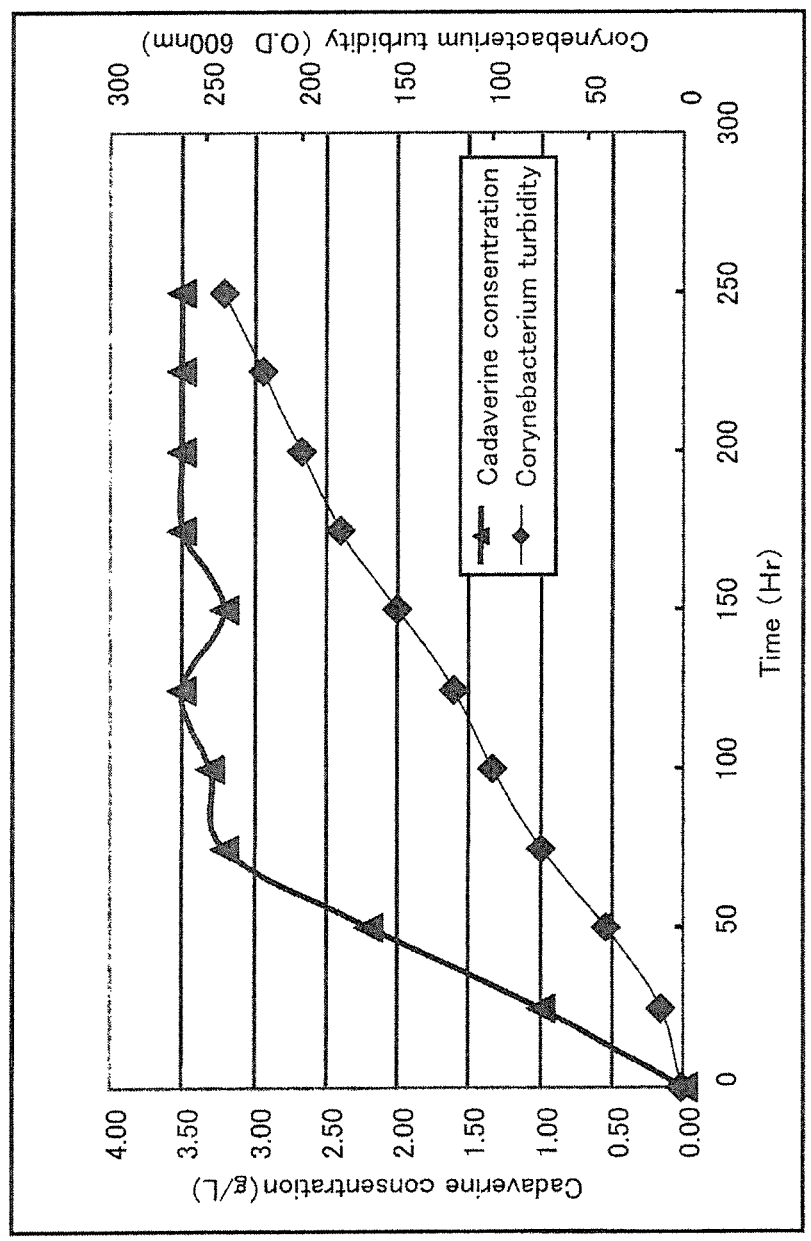
FIG. 18 is a drawing that shows a cadaverine concentration and a coryneform-bacteria turbidity obtained in Example 10.

After 250 hours culture, the yeast turbidity in the fermentation tank, the concentration of cadaverine as a product in the filtration liquid and the sugar concentration were measured, and the yield of cadaverine per sugar was also calculated. These results are shown in FIG. 18 and Table 4. The cadaverine concentration was 3.5 g/L. Moreover, the *Corynebacterium* turbidity was measured by a photometer based upon light absorption at 600 nm. Moreover, the yield of cadaverine per sugar was 3%.

The cadaverine concentration was measured through the following method: Analyzing Method of cadaverine concentration by HPLC Column to be used: CAPCELL PAK C18 (manufactured by Shiseido Co., Ltd.)
    Mobile Phase: 0.1% (w/w) aqueous solution of phosphoric acid: acetonitrile=4.5:5.5
    Detection: UV 360 nm
    Sample pre-treatment: To an analysis sample (25 μl) were added 25 μl of 1,4-diaminobutane (0.03 M) serving as an internal standard substance, 150 μl of sodium hydrogen acetate (0.075 M) and an ethanol solution of 2,4-dinitrofluorobenzene (0.2 M), and mixed with one another, and this was kept at 37° C. for one hour.

After the reaction solution (50 μl) had been dissolved in 1 ml of acetonitrile, the resultant solution was centrifuged at 10,000 rpm for 5 minutes, and its supernatant fluid (10 μl) was then subjected to an HPLC analysis.

Comparative Example 5

Continuous fermentation was carried out in the same manner as in Example 10 except that the apparatus shown in FIG. 9 was used. The *Corynebacterium* turbidity and the concentration of cadaverine as a produced product were measured. In this case, the apparatus shown in FIG. 9 had the same structure as that of the apparatus shown in FIG. 2, except that the bypass line 26, the flowing quantity control means 25 and the open/close valves of the membrane separation tank 27 and 28 were not installed therein.

Figure 19:
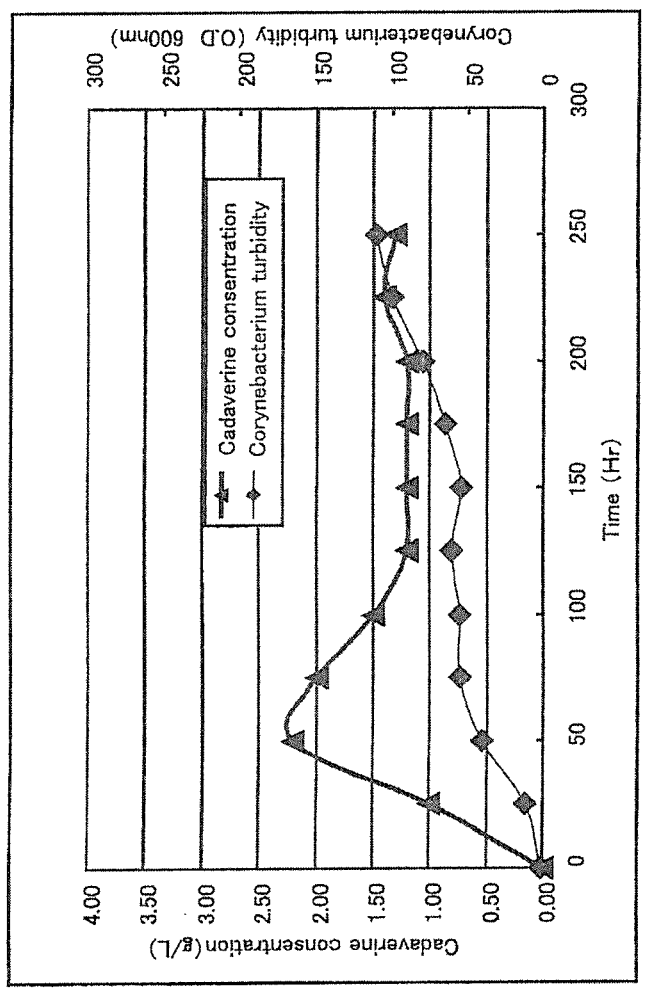
FIG. 19 is a drawing that shows a cadaverine concentration and a coryneform-bacteria turbidity obtained in Comparative Example 5.

The results are shown in FIG. 19 and Table 4. Moreover, the pressure of a culture liquid to be supplied to the membrane separation tank during the continuous fermentation was measured, and the results are shown in FIG. 20.

TABLE 4

| Example Conditions | Example 10 | Comparative Example 5 |
|---|---|---|
| Chemical Product | Cadaverine | Cadaverine |
| Microorganism | TR-CAD1 | TR-CAD1 |
| Apparatus | FIG. 2 | FIG. 9 |
| Pump 4 | 3 L/hr | 3 L/hr |
| Pump 5 | 5 L/min | 5 L/min |
| Pump 16 | — | — |
| Flux | 0.180 m/day | 0.180 m/day |
| Recovery Percentage | 1% or less | 1% |
| Fermentation Time | 250 h | 250 h |
| Compound Concentration | 3.5 g/L | 1.2 g/L |
| Microorganism Concentration | 250 | 100 |
| Yield Per Sugar | 3% | 1% |

Figure 20:
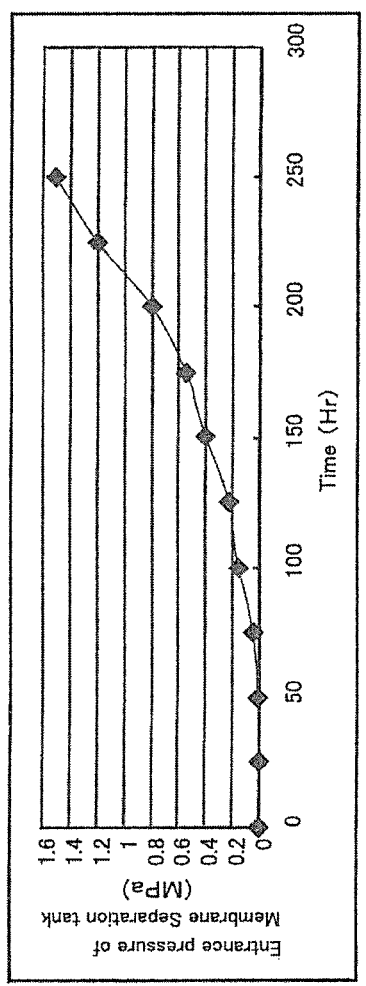
FIG. 20 is a drawing that shows a pressure of a culture liquid at the flow-in side of a membrane separation tank obtained in Comparative Example 5.

In Comparative Example 5, since no control was carried out on the pressure of the culture liquid to be supplied to the membrane separation tank, the pressure increased during the continuous fermentation, and 225 hours after the start of the fermentation, it became 1 MPa or more as shown in FIG. 20. Moreover, both of the *Corynebacterium* turbidity and the concentration of cadaverine became lower than those in Example 10. The yield of cadaverine per sugar was 1.0%.

As described above, by adjusting the flowing culture liquid into the membrane separation tank by the bypass line 26 and the flowing quantity control means 25 attached thereto, unexpected effects such as high concentration fermentation of *Corynebacterium*, improvement of the concentration of cadaverine (chemical product) and improvement of the yield of cadaverine per sugar, were confirmed.

Example 11

By using a *Corynebacterium glutamicum* delta-HOM strain described in JP-A No. 2008-212138, continuous fermentation was carried out by the continuous fermentation apparatus shown in FIG. 2 so that L-lysine was produced. As the culture medium, a L-lysine production medium having a composition shown in Table 5 was used. This L-lysine production medium was subjected to a high-pressure (2 atm) steam sterilizing treatment at 121° C. for 15 minutes, and then used. As the separation membrane element member, a molded product composed of stainless steel and polysulfone resin was used, and as the separation membrane, the porous flat membrane, produced in Reference Example 2, was used. Moreover, as the pump 5 inside the liquid transfer line 17, a diaphragm-type pump "APLS-20" (manufactured by TACMINA Corporation) was used, and as the pump 4 to be used for drawing a filtration liquid from the membrane separation tank, a peristaltic pump was used.

TABLE 5

| L-lysine Production Medium | |
|---|---|
| Glucose | 100 g/L |
| Urea | 1 g/L |
| Yeast Extract | 5 g/L |
| Dipotassium hydrogen phosphate | 2.5 g/L |
| Magnesium sulfate heptahydrate | 0.75 g/L |
| Calcium chloride dihydrate | 0.05 g/L |
| Iron sulfate heptahydrate | 0.05 g/L |
| Manganese sulfate pentahydrate | 13 ppm |
| Copper sulfate pentahydrate | 6.3 ppm |
| Zinc sulfate heptahydrate | 13 ppm |
| Nickel chloride hexahydrate | 5 ppm |
| Cobalt chloride hexahydrate | 1.3 ppm |
| Molybdenum | 1.3 ppm |
| β-alanine | 23 ppm |
| Nicotinic acid | 14 ppm |
| Biotin | 0.5 ppm |
| Thiamin | 7 ppm |

Moreover, conditions in examples are explained as follows:
    Fermentation tank capacity: 20 (L)
    Separation membrane to be used: PVDF filtration membrane (produced in Reference Example 2)
    Membrane separation tank capacity: 5 (L)

Membrane separation element effective filtration area: 4000 cm$^2$

Temperature adjustment: 30 (° C.)

Fermentation tank draft quantity: air 5 (L/min)

Stirring velocity of fermentation tank: 300 (rpm)

pH adjustment: adjusted to pH 7.3 by using 3M HCl and 3M ammonia water

Medium supply velocity: variably controlled by a level sensor inside the fermentation tank Sterilization: pressurized steam sterilization under 121° C. at 0.2 MPa for 20 minutes over all the membrane separation tank, fermentation tank and the medium to be used Flowing quantity of pump 4: 3 L/hr Maximum inner diameter of liquid transfer lines 15, 17: 50 mm Output of pump 5: 5 L/min Linear speed of liquid transfer lines 15, 17: 4.2 cm/sec Flux: 0.180 m/day Recovery percentage: not controlled (1% or less).

As a pre-culture, delta-HOM strain was subjected to shaking culture overnight (primary pre-culture primarily carried) on a BY medium of 5 ml (0.5% yeast extract, 0.7% meat extract, 1% heptone, 0.3% sodium chloride) in a test tube. The culture liquid thus obtained was inoculated into a L-lysine production medium of 50 ml and subjected to, in a 500-ml Sakaguchi flask, shaking culture at 30° C. for 24 hours under conditions of an amplitude of 30 cm, at 180 rpm (pre-culture preliminarily carried out). The resultant culture liquid was inoculated into a fresh L-lysine production medium of 1000 ml, and subjected to shaking culture, in a 3000-ml Sakaguchi flask at 30° C. for 24 hours (pre-culture). This pre-culture liquid was inoculated into a L-lysine production media of total 20 L of the fermentation tank 1 and the inside of the membrane separation tank, and the inside of the fermentation tank was stirred by a stirrer attached thereto, and the draft quantity was adjusted, and the temperature and the pH were adjusted, and after 50 hours culture, the pump 4 was operated so that a filtration liquid containing L-lysine was drawn out.

At this time, the pressure of the culture liquid to flow into the membrane separation tank 2 was measured once a day, and the flowing quantity control means 25 (butterfly valve) attached to the bypass line 26 was adjusted so that the gauge pressure was 0.1 MPa.

Figure 21:
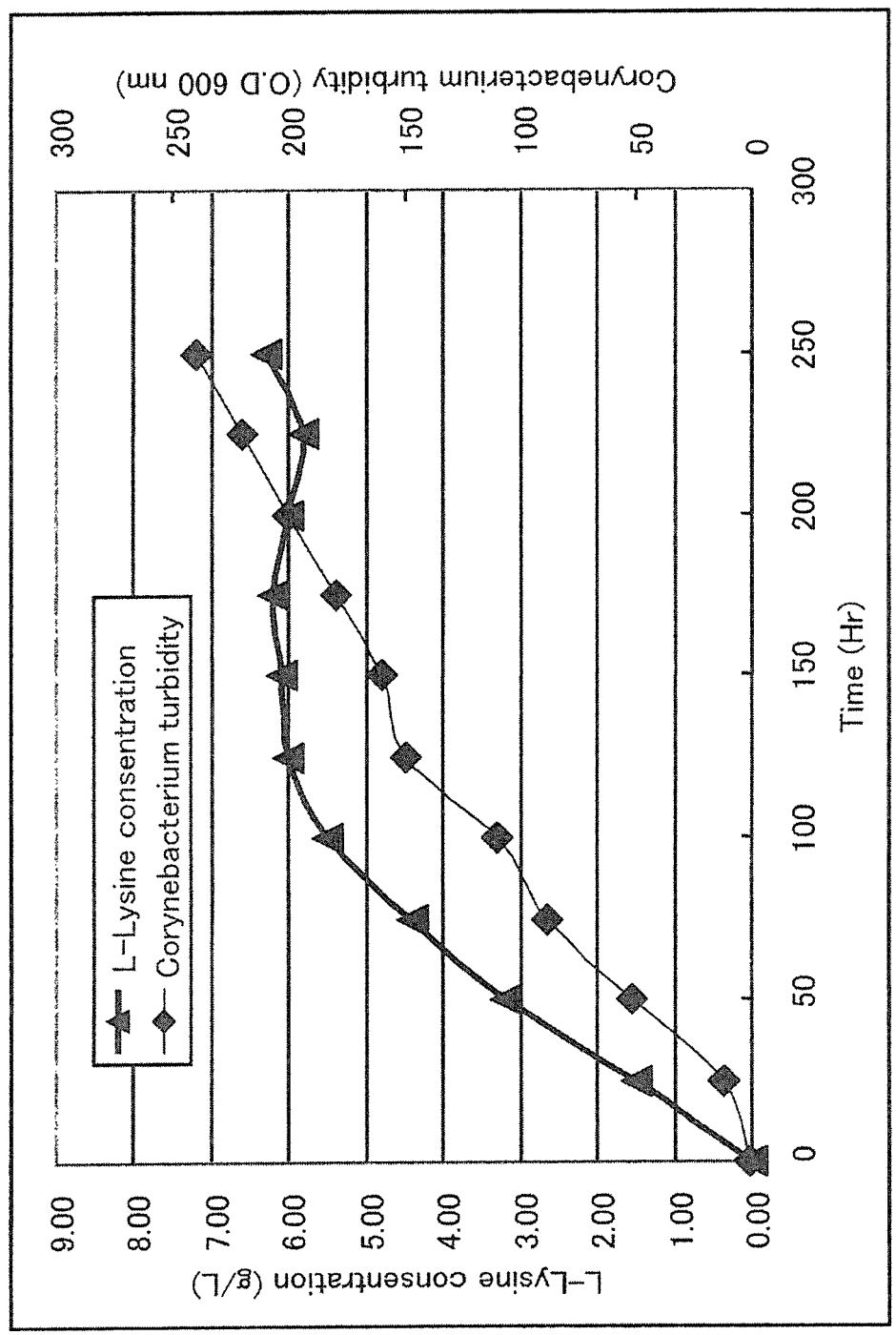
FIG. 21 is a drawing that shows an L-lysine concentration and a coryneform-bacteria turbidity obtained in Example 11.

After 250 hours culture, the *Corynebacterium* turbidity in the fermentation tank, the concentration of L-lysine as a product in the filtration liquid and the sugar concentration were measured, and the yield of L-lysine per sugar was also calculated. The results of these are shown in FIG. 21 and Table 6. The L-lysine concentration was 6.0 g/L. Moreover, the *Corynebacterium* turbidity was measured by a photometer based upon light absorption at 600 nm. Moreover, the yield of L-lysine per sugar was 5.5%. The L-lysine concentration was measured by using the same measuring method as in cadaverine concentration.

Comparative Example 6

Continuous fermentation was carried out in the same manner as in Example 11 except that the apparatus shown in FIG. 9 was used. The *Corynebacterium* turbidity and the concentration of cadaverine as a product were measured. In this case, the apparatus shown in FIG. 9 had the same structure as that shown in FIG. 2, except that the bypass line 26, the flowing quantity control means 25 and the open/close valves of the membrane separation tank 27 and 28 were not installed therein.

Figure 22:
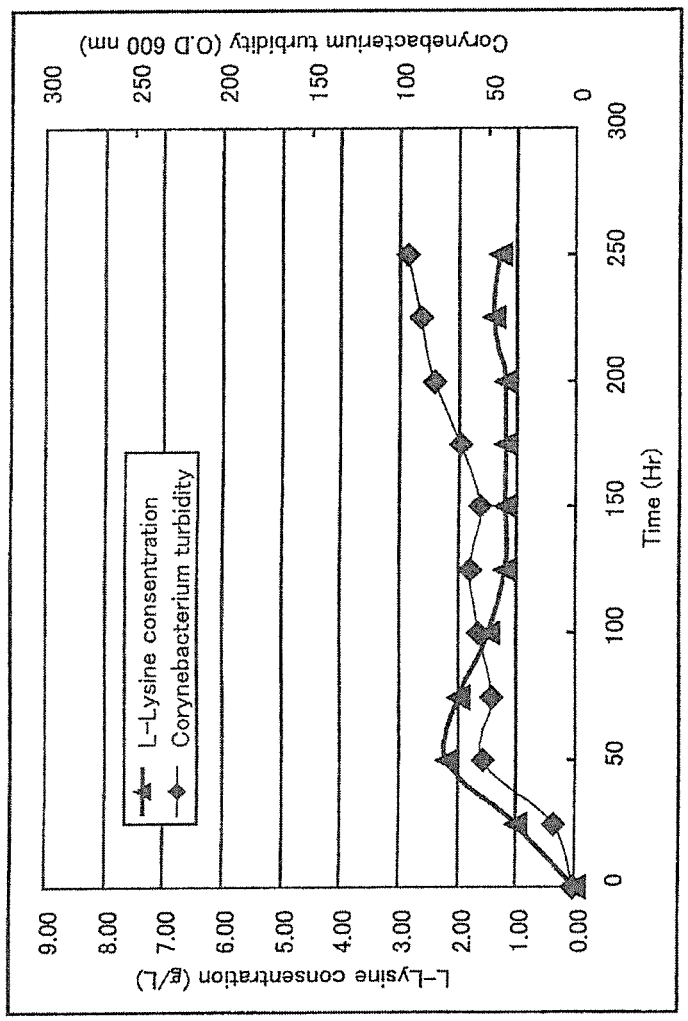
FIG. 22 is a drawing that shows an L-lysine concentration and a coryneform-bacteria turbidity obtained in Comparative Example 6.

The results are shown in FIG. 22 and Table 6. Moreover, the pressure of a culture liquid to be supplied to the membrane separation tank during the continuous fermentation was measured, and the results are shown in FIG. 23.

TABLE 6

| Example Conditions | Example 11 | Comparative Example 6 |
|---|---|---|
| Chemical Product | L-lysine | L-lysine |
| Microorganism | delta-HOM | delta-HOM |
| Apparatus | FIG. 2 | FIG. 9 |
| Pump 4 | 3 L/hr | 3 L/hr |
| Pump 5 | 5 L/min | 5 L/min |
| Pump 16 | — | — |
| Flux | 0.180 m/day | 0.180 m/day |
| Recovery Percentage | 1% or less | 1% |
| Fermentation Time | 250 h | 250 h |
| Compound Concentration | 6.0 g/L | 1.2 g/L |
| Microorganism Concentration | 250 | 100 |
| Yield Per Sugar | 5.5% | 1.1% |

Figure 23:
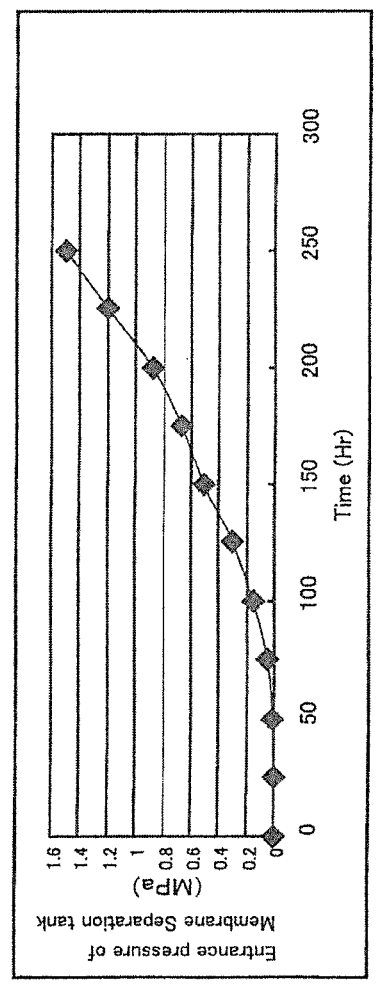
FIG. 23 is a drawing that shows a pressure of a culture liquid at the flow-in side of a membrane separation tank obtained in Comparative Example 6.

In Comparative Example 6, since no control was carried out on the pressure of the culture liquid to be supplied to the membrane separation tank, the pressure was fluctuated during the continuous fermentation, and 225 hours after the start of the fermentation, it became 1 MPa or more as shown in FIG. 23. Moreover, both of the *Corynebacterium* turbidity and the concentration of L-lysine became lower than those in Example 11. The yield of L-lysine per sugar was 1.1%.

As described above, by adjusting the flowing culture liquid into the membrane separation tank by the bypass line 26 and the flowing quantity control means 25 attached thereto, unexpected effects such as high concentration fermentation of *Corynebacterium*, improvement of the concentration of L-lysine (chemical product) and improvement of the yield of L-lysine per sugar, were confirmed.

INDUSTRIAL APPLICABILITY

Our methods can be suitably applied to production of various chemical products obtained by the fermentation of microorganisms such as alcohols, organic acids, amino acids, nucleic acids, enzymes, antibiotics, and recombination proteins.

The invention claimed is:

1. A method of producing a chemical product comprising:
cultivating microorganisms or cells with a culture liquid inside a fermentation tank to produce a chemical product in the culture liquid;
transferring the culture liquid which comprises the chemical product from the fermentation tank wherein the culture liquid is split into two separate streams, one stream flowing to a membrane separation filter tank while the other flows to a bypass;
the culture liquid flowing to the membrane separation tank has a portion of the liquid filtered through the membrane while the remaining portion of the liquid is unfiltered;
the filtered liquid with the chemical product is collected;
the unfiltered liquid is refluxed and recycled upstream of the membrane separation tank; and
the culture liquid which flows to the bypass is recycled upstream of the bypass,
wherein the chemical product is an alcohol, an organic acid, amino acid, or a diamine produced through fermentation.

2. The method according to claim 1, wherein a flowing quantity of the culture liquid to be allowed to bypass the membrane separation tank is controlled so that the pressure at the culture liquid flow-in side of the membrane separation tank is 1 MPa or less.

3. The method according to claim 1, wherein one portion of the unfiltered culture liquid is refluxed to be joined to the culture liquid in the fermentation tank, while a remaining portion of the unfiltered culture liquid is refluxed to be joined to a culture liquid located between the fermentation tank and the membrane separation tank.

4. The method according to claim 3, wherein a flowing quantity of the unfiltered culture liquid to be refluxed to be joined to the culture liquid located between the fermentation tank and the membrane separation tank and a flowing quantity of the unfiltered culture liquid to be refluxed to be joined to the culture liquid in the fermentation tank are each independently controlled.

5. The method according to claim 3, wherein a ratio of a flowing quantity of the unfiltered culture liquid to be refluxed to be joined to the culture liquid in the fermentation tank to a flowing quantity of the unfiltered culture liquid to be refluxed to be joined to the culture liquid located between the fermentation tank and the membrane separation tank is 1 or less.

6. The method according to claim 1, wherein each of a linear speed of the culture liquid to be transported from the fermentation tank to the membrane separation tank, a linear speed of the unfiltered culture liquid refluxed from the membrane separation tank to be joined to the culture liquid on the upstream side of the membrane separation tank and a linear speed of the culture liquid allowed to bypass the membrane separation tank is 2.5 cm/sec or more.

7. The method according to claim 1, wherein a quantity of culture liquid to flow into the membrane separation tank and/or a quantity of filtration liquid from the separation membrane are adjusted so that the recovery percentage of the quantity of filtration liquid from the separation membrane to the quantity of culture liquid to flow into the membrane separation tank is 10.0% or less.

8. The method according to claim 1, wherein a ratio of the culture liquid volume in the fermentation tank to a culture liquid volume in the membrane separation tank is 4 to 100.

* * * * *

UNITED STATES PATENT AND TRADEMARK OFFICE
CERTIFICATE OF CORRECTION

PATENT NO. : 10,428,358 B2
APPLICATION NO. : 15/051710
DATED : October 1, 2019
INVENTOR(S) : Mimitsuka et al.

Page 1 of 1

It is certified that error appears in the above-identified patent and that said Letters Patent is hereby corrected as shown below:

In the Specification

<u>In Column 13</u>
At Line 20, after "line 15)", please change "a" to -- α --.

Signed and Sealed this
Eighteenth Day of August, 2020

Andrei Iancu
*Director of the United States Patent and Trademark Office*

SEQUENCE LISTING

<160> NUMBER OF SEQ ID NOS: 9

<210> SEQ ID NO 1
<211> LENGTH: 26
<212> TYPE: DNA
<213> ORGANISM: Artificial

```
<220> FEATURE:
<223> OTHER INFORMATION: Description of Artificial Sequence: primer

<400> SEQUENCE: 1
ctcgagatgg caactctaaa ggatca                                            26

<210> SEQ ID NO 2
<211> LENGTH: 28
<212> TYPE: DNA
<213> ORGANISM: Artificial
<220> FEATURE:
<223> OTHER INFORMATION: Description of Artificial Sequence: primer

<400> SEQUENCE: 2
gcggccgctt aaaattgcag ctcctttt                                          28

<210> SEQ ID NO 3
<211> LENGTH: 999
<212> TYPE: DNA
<213> ORGANISM: Homo sapiens

<400> SEQUENCE: 3
atggcaactc taaaggatca gctgatttat aatcttctaa aggaagaaca gaccccccag        60
aataagatta cagttgttgg ggttggtgct gttggcatgg cctgtgccat cagtatctta       120
atgaaggact tggcagatga acttgctctt gttgatgtca tcgaagacaa attgaaggga       180
gagatgatgg atctccaaca tggcagcctt ttccttagaa caccaaagat tgtctctggc       240
aaagactata atgtaactgc aaactccaag ctggtcatta tcacggctgg ggcacgtcag       300
caagagggag aaagccgtct taatttggtc agcgtaacg tgaacatatt taaattcatc        360
attcctaatg ttgtaaaata cagcccgaac tgcaagttgc ttattgtttc aaatccagtg       420
gatatcttga cctacgtggc ttggaagata agtggttttc ccaaaaaccg tgttattgga       480
agtggttgca atctggattc agcccgattc cgttacctga tggggaaaag gctgggagtt       540
cacccattaa gctgtcatgg gtgggtcctt ggggaacatg gagattccag tgtgcctgta       600
tggagtggaa tgaatgttgc tggtgtctct ctgaagactc tgcacccaga tttagggact       660
gataaagata aggaacagtg gaaagaggtt cacaagcagg tggttgagag tgcttatgag       720
gtgatcaaac tcaaaggcta cacatcctgg gctattggac tctctgtagc agatttggca       780
gagagtataa tgaagaatct taggcgggtg cacccagttt ccaccatgat taagggtctt       840
tacggaataa aggatgatgt cttccttagt gttccttgca ttttgggaca gaatggaatc       900
tcagaccttg tgaaggtgac tctgacttct gaggaagagg cccgtttgaa gaagagtgca       960
gatacacttt gggggatcca aaaggagctg caatttttaa                            999

<210> SEQ ID NO 4
<211> LENGTH: 80
<212> TYPE: DNA
<213> ORGANISM: Artificial
<220> FEATURE:
<223> OTHER INFORMATION: Description of Artificial Sequence: primer

<400> SEQUENCE: 4
tctcaattat tattttctac tcataacctc acgcaaaata acacagtcaa atcaatcaaa        60
atggcaactc taaaggatca                                                   80

<210> SEQ ID NO 5
<211> LENGTH: 20
<212> TYPE: DNA
```

```
<213> ORGANISM: Artificial
<220> FEATURE:
<223> OTHER INFORMATION: Description of Artificial Sequence: primer

<400> SEQUENCE: 5
aggcgtatca cgaggccctt                                                      20

<210> SEQ ID NO 6
<211> LENGTH: 60
<212> TYPE: DNA
<213> ORGANISM: Artificial
<220> FEATURE:
<223> OTHER INFORMATION: Description of Artificial Sequence: primer

<400> SEQUENCE: 6
gaattaattc ttgaagacga aagggcctcg tgatacgcct agattgtact gagagtgcac         60

<210> SEQ ID NO 7
<211> LENGTH: 80
<212> TYPE: DNA
<213> ORGANISM: Artificial
<220> FEATURE:
<223> OTHER INFORMATION: Description of Artificial Sequence: primer

<400> SEQUENCE: 7
tatttttcgt tacataaaaa tgcttataaa actttaacta ataattagag attaaatcgc         60
ctgtgcggta tttcacaccg                                                      80

<210> SEQ ID NO 8
<211> LENGTH: 25
<212> TYPE: DNA
<213> ORGANISM: Artificial
<220> FEATURE:
<223> OTHER INFORMATION: Description of Artificial Sequence: primer

<400> SEQUENCE: 8
caaatatcgt ttgaatattt ttccg                                                25

<210> SEQ ID NO 9
<211> LENGTH: 20
<212> TYPE: DNA
<213> ORGANISM: Artificial
<220> FEATURE:
<223> OTHER INFORMATION: Description of Artificial Sequence: primer

<400> SEQUENCE: 9
aatccagatt gcaaccactt                                                      20
```